United States Patent
Baeuerle et al.

(10) Patent No.: US 10,844,134 B2
(45) Date of Patent: *Nov. 24, 2020

(54) PSMA TARGETING TRISPECIFIC PROTEINS AND METHODS OF USE

(71) Applicant: Harpoon Therapeutics, Inc., South San Francisco, CA (US)

(72) Inventors: Patrick Baeuerle, Gauting (DE); Jeanmarie Guenot, San Francisco, CA (US); Holger Wesche, San Francisco, CA (US); Robert B. Dubridge, Belmont, CA (US); Bryan D. Lemon, Mountain View, CA (US); Richard J. Austin, San Francisco, CA (US); Pui Seto, San Carlos, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,530

(22) Filed: Nov. 22, 2017

(65) Prior Publication Data

US 2018/0162949 A1   Jun. 14, 2018

Related U.S. Application Data

(60) Provisional application No. 62/426,077, filed on Nov. 23, 2016, provisional application No. 62/426,069, filed on Nov. 23, 2016.

(51) Int. Cl.
| | |
|---|---|
| *A61K 39/00* | (2006.01) |
| *C07K 16/30* | (2006.01) |
| *C07K 16/28* | (2006.01) |
| *A61P 35/00* | (2006.01) |
| *C07K 16/18* | (2006.01) |
| *A61K 39/395* | (2006.01) |

(52) U.S. Cl.
CPC .......... *C07K 16/3069* (2013.01); *A61P 35/00* (2018.01); *C07K 16/18* (2013.01); *C07K 16/2809* (2013.01); *C07K 16/2863* (2013.01); *A61K 39/39558* (2013.01); *A61K 2039/505* (2013.01); *C07K 2317/31* (2013.01); *C07K 2317/33* (2013.01); *C07K 2317/569* (2013.01); *C07K 2317/622* (2013.01); *C07K 2317/73* (2013.01); *C07K 2317/92* (2013.01); *C07K 2317/94* (2013.01)

(58) Field of Classification Search
CPC .................... A61K 2039/505; A61K 39/39558
See application file for complete search history.

(56) References Cited

U.S. PATENT DOCUMENTS

| | | |
|---|---|---|
| 4,816,567 A | 3/1989 | Cabilly et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,840,526 A | 11/1998 | Casterman et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 6,005,079 A | 12/1999 | Casterman et al. |
| 6,015,695 A | 1/2000 | Casterman et al. |
| 6,107,090 A | 8/2000 | Bander |
| 6,120,766 A | 9/2000 | Hale et al. |
| 6,136,311 A | 10/2000 | Bander |
| 6,326,193 B1 | 12/2001 | Liu et al. |
| 6,331,415 B1 | 12/2001 | Cabilly et al. |

(Continued)

FOREIGN PATENT DOCUMENTS

| | | |
|---|---|---|
| CN | 1563092 A | 1/2005 |
| CN | 101646689 A | 2/2010 |

(Continued)

OTHER PUBLICATIONS

Schmittgen et al. (Int. J. Cancer. Nov. 1, 2003; 107 (2): 323-9).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*

(Continued)

*Primary Examiner* — Stephen L Rawlings
(74) *Attorney, Agent, or Firm* — Wilson Sonsini Goodrich & Rosati

(57) ABSTRACT

Provided herein are prostate specific membrane antigen (PSMA) targeting trispecific proteins comprising a domain binding to CD3, a half-life extension domain, and a domain binding to PSMA. Also provided are pharmaceutical compositions thereof, as well as nucleic acids, recombinant expression vectors and host cells for making such PSMA targeting trispecific proteins. Also disclosed are methods of using the disclosed PSMA targeting trispecific proteins in the prevention, and/or treatment diseases, conditions and disorders.

11 Claims, 16 Drawing Sheets

Specification includes a Sequence Listing.

(56) References Cited

U.S. PATENT DOCUMENTS

| | | |
|---|---|---|
| 6,352,694 B1 | 3/2002 | June et al. |
| 6,407,213 B1 | 6/2002 | Carter et al. |
| 6,534,055 B1 | 3/2003 | June et al. |
| 6,548,640 B1 | 4/2003 | Winter |
| 6,670,453 B2 | 12/2003 | Frenken et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,232,566 B2 | 6/2007 | June et al. |
| 7,262,276 B2 | 8/2007 | Huang et al. |
| 7,666,414 B2 | 2/2010 | Bander |
| 7,807,162 B2 | 10/2010 | Silence |
| 7,850,971 B2 | 12/2010 | Maddon et al. |
| 8,114,965 B2 | 2/2012 | Maddon et al. |
| 8,188,223 B2 | 5/2012 | Beirnaert et al. |
| 8,236,308 B2 | 8/2012 | Kischel et al. |
| 8,470,330 B2 | 6/2013 | Schuelke et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,784,821 B1 | 7/2014 | Kufer et al. |
| 8,846,042 B2 | 9/2014 | Zhou |
| 8,907,071 B2 | 12/2014 | Sullivan et al. |
| 8,937,164 B2 | 1/2015 | Descamps et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,340,621 B2 | 5/2016 | Kufer et al. |
| 9,708,412 B2 * | 7/2017 | Baeuerle ............... A61P 37/02 |
| 10,428,120 B2 * | 10/2019 | Kontermann ...... C07K 16/3007 |
| 2005/0042664 A1 | 2/2005 | Wu et al. |
| 2005/0048617 A1 | 3/2005 | Wu et al. |
| 2005/0100543 A1 | 5/2005 | Hansen et al. |
| 2005/0175606 A1 | 8/2005 | Huang et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0259026 A1 | 10/2009 | Tomlinson et al. |
| 2010/0122358 A1 | 5/2010 | Brueggemann et al. |
| 2010/0150918 A1 | 6/2010 | Kufer et al. |
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2011/0129458 A1 | 6/2011 | Dolk et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0231024 A1 | 9/2012 | Elsasser-Beile et al. |
| 2012/0328619 A1 | 12/2012 | Fey et al. |
| 2013/0017200 A1 | 1/2013 | Scheer et al. |
| 2013/0136744 A1 | 5/2013 | Bouche et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0330335 A1 | 12/2013 | Bremel et al. |
| 2014/0004121 A1 | 1/2014 | Fanslow, III et al. |
| 2014/0023664 A1 | 1/2014 | Lowman et al. |
| 2014/0045195 A1 | 2/2014 | Daugherty et al. |
| 2014/0073767 A1 | 3/2014 | Lee et al. |
| 2014/0088295 A1 | 3/2014 | Smith et al. |
| 2014/0205601 A1 | 7/2014 | Beirnaert et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0024174 A1 | 1/2016 | Odunsi et al. |
| 2016/0032019 A1 | 2/2016 | Xiao et al. |
| 2016/0039942 A1 | 2/2016 | Cobbold et al. |
| 2016/0068605 A1 | 3/2016 | Nemeth et al. |
| 2016/0130331 A1 | 5/2016 | Stull et al. |
| 2016/0215063 A1 | 7/2016 | Bernett et al. |
| 2016/0251440 A1 | 9/2016 | Roobrouck et al. |
| 2016/0257721 A1 | 9/2016 | Lieber et al. |
| 2016/0319040 A1 | 11/2016 | Dreier et al. |
| 2016/0340444 A1 * | 11/2016 | Baeuerle ............... A61P 37/02 |
| 2016/0355842 A1 | 12/2016 | Parks et al. |
| 2017/0029502 A1 | 2/2017 | Raum et al. |
| 2017/0152316 A1 | 6/2017 | Cobbold et al. |
| 2017/0204164 A1 | 7/2017 | Himmler et al. |
| 2017/0275373 A1 | 9/2017 | Kufer et al. |
| 2017/0298149 A1 | 10/2017 | Baeuerle et al. |
| 2017/0334979 A1 | 11/2017 | Dubridge et al. |
| 2017/0334997 A1 * | 11/2017 | Dubridge ............... A61P 31/00 |
| 2017/0369563 A1 * | 12/2017 | Dubridge ............... A61P 37/06 |
| 2017/0369575 A1 | 12/2017 | Dubridge et al. |
| 2018/0016323 A1 | 1/2018 | Brandenburg et al. |
| 2018/0134789 A1 | 5/2018 | Baeuerle et al. |
| 2018/0148508 A1 | 5/2018 | Wang et al. |
| 2019/0031749 A1 | 1/2019 | Dubridge et al. |
| 2019/0092862 A1 | 3/2019 | Cui et al. |
| 2019/0225702 A1 | 7/2019 | Baeuerle et al. |
| 2020/0095340 A1 | 3/2020 | Wesche et al. |
| 2020/0115461 A1 | 4/2020 | Evnin et al. |
| 2020/0148771 A1 | 5/2020 | Paeuerle et al. |

FOREIGN PATENT DOCUMENTS

| | | |
|---|---|---|
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| FR | 901228 A | 7/1945 |
| JP | 2005501517 A | 1/2005 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0190190 A2 | 11/2001 |
| WO | WO-0196584 A2 | 12/2001 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004041867 A2 | 5/2004 |
| WO | WO-2004042404 A1 | 5/2004 |
| WO | WO-2004049794 A2 | 6/2004 |
| WO | WO-2006020258 A2 | 2/2006 |
| WO | WO-2006122787 A1 | 11/2006 |
| WO | WO-2007024715 A2 | 3/2007 |

(56) References Cited

FOREIGN PATENT DOCUMENTS

| | | |
|---|---|---|
| WO | WO-2007042261 A2 | 4/2007 |
| WO | WO-2007062466 A1 | 6/2007 |
| WO | WO-2007115230 A2 | 10/2007 |
| WO | WO-2008028977 A2 | 3/2008 |
| WO | WO-2009025846 A2 | 2/2009 |
| WO | WO-2009030285 A1 | 3/2009 |
| WO | WO-2009147248 A2 | 12/2009 |
| WO | WO-2010003118 A1 | 1/2010 |
| WO | WO-2010037836 A2 | 4/2010 |
| WO | WO-2010037837 A2 | 4/2010 |
| WO | WO-2011039368 A2 | 4/2011 |
| WO | WO-2011051327 A2 | 5/2011 |
| WO | WO-2012131053 A1 | 10/2012 |
| WO | WO-2012138475 A1 | 10/2012 |
| WO | WO-2012158818 A2 | 11/2012 |
| WO | WO-2013036130 A1 | 3/2013 |
| WO | WO-2013104804 A2 | 7/2013 |
| WO | WO-2013110531 A1 | 8/2013 |
| WO | WO-2013128027 A1 | 9/2013 |
| WO | WO-2014033304 A2 | 3/2014 |
| WO | WO-2014138306 A1 | 9/2014 |
| WO | WO-2014140358 A1 | 9/2014 |
| WO | WO-2014151910 A1 | 9/2014 |
| WO | WO-2015103072 A1 | 7/2015 |
| WO | WO-2015150447 A1 | 10/2015 |
| WO | WO-2015184207 A1 | 12/2015 |
| WO | WO-2016009029 A1 | 1/2016 |
| WO | WO-2016034044 A1 | 3/2016 |
| WO | WO-2016046778 A2 | 3/2016 |
| WO | WO-2016055551 A1 | 4/2016 |
| WO | WO-2016105450 A2 | 6/2016 |
| WO | WO-2016130819 A2 | 8/2016 |
| WO | WO-2016171999 A2 | 10/2016 |
| WO | WO-2016179003 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017025698 A1 | 2/2017 |
| WO | WO-2017027392 A1 | 2/2017 |
| WO | WO-2017041749 A1 | 3/2017 |
| WO | WO-2017079528 A1 | 5/2017 |
| WO | WO-2017136549 A1 | 8/2017 |
| WO | WO-2017156178 A1 | 9/2017 |
| WO | WO-2017201488 A1 | 11/2017 |
| WO | WO-2017201493 A1 | 11/2017 |
| WO | WO-2018017863 A1 | 1/2018 |
| WO | WO-2018071777 A1 | 4/2018 |
| WO | WO-2018098354 A1 | 5/2018 |
| WO | WO-2018098356 A1 | 5/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018204717 A1 | 11/2018 |
| WO | WO-2018209298 A1 | 11/2018 |
| WO | WO-2018209304 A1 | 11/2018 |
| WO | WO-2019075359 A1 | 4/2019 |
| WO | WO-2019075378 A1 | 4/2019 |
| WO | WO-2019222278 A1 | 11/2019 |
| WO | WO-2019222282 A1 | 11/2019 |
| WO | WO-2019222283 A1 | 11/2019 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |

OTHER PUBLICATIONS

Winkler et al. (J. Immunol. Oct. 15, 2000; 165 (8): 4505-4514).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Vincke et al. (J. Biol. Chem. Jan. 30, 2009; 284 (5): 3273-84).*
Tiller et al. (Front. Immunol. 2017; 8: 986; pp. 1-16).*
Chang et al. (Structure. Jan. 7, 2014; 22 (1): 9-21).*
Saeren et al. (J. Mol. Biol. Sep. 23, 2005; 352 (3): 597-607).*
Baum et al. (Immunotherapy. Jan. 5, 2013; 5 (1): 27-38).*
Zare et al. (Int. J. Biol. Markers. Jun. 25, 2014; 29 (2): e169-79; pp. 1-11).*
Almagro et al. Humanization of antibodies. Front Biosci 13:1619-1633 (2008).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Bedouelle et al. Diversity and junction residues as hotspots of binding energy in an antibody neutralizing the dengue virus. FEBS J 273(1):34-46 (2006).
Brown et al. Tolerance of single, but not multiple, amino acid replacements in antibody VH CDR 2: a means of minimizing B cell wastage from somatic hypermutation? J Immunol 156(9):3285-3291 (1996).
Carter et al. Humanization of an anti-p185HER2 antibody for human cancer therapy. PNAS USA 89(10):4285-4289 (1992).
Casset et al. A peptide mimetic of an anti-CD4 monoclonal antibody by rational design. Biochemical and Biophysical Research Communication 307:198-205 (2003).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Selection and analysis of an optimized anti-VEGF antibody: Crystal structure of an affinity-matured Fab in complex with antigen. J Mol Bio 293:865-881 (1999).
Chothia et al. Canonical structures for the hypervariable regions of immunoglobulins. J Mol Biol 196(4):901-917 (1987).
Co-pending U.S. Appl. No. 15/821,498, filed Nov. 22, 2017.
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Frankel et al. Targeting T cells to tumor cells using bispecific antibodies. Curr Opin Chem Biol 17(3):385-392 (2013).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Harding et al. The immunogenicity of humanized and fully human antibodies: residual immunogenicity resides in the CDR regions. MAbs 2(3):256-265 (2010).
Hutchinson et al. Mutagenesis at a specific position in a DNA sequence. J Biol Chem 253:6551-6560 (1978).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Le Gall et al. Immunosuppressive properties of anti-CD3 single-chain Fv and diabody. J Immunol Methods 285(1):111-127 (2004).
Lutterbuese et al. T cell-engaging BiTE antibodies specific for EGFR potently eliminate KRAS- and BRAF-mutated colorectal cancer cells. PNAS 107:12605-12610 (2007).
Maccallum et al. Antibody-antigen interactions: contact analysis and binding site topography. J Mol Biol. 262(5):732-745 (1996).
Muller et al. Improving the pharmacokinetic properties of biologics by fusion to an anti-HSA shark VNAR domain. MAbs 4(6):673-685 (2012).
Nazarian et al. Characterization of bispecific T-cell Engager (BiTE) antibodies with a high-capacity T-cell dependent cellular cytotoxicity (TDCC) assay. J Biomol Screen 20:519-527 (2015).

(56) References Cited

OTHER PUBLICATIONS

Ohiro et al. A homogeneous and noncompetitive immunoassay based on the enhanced fluorescence resonance energy transfer by leucine zipper interaction. Anal Chem 74(22):5786-5792 (2002).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Padlan. Anatomy of the Antibody Molecule. Mol Immunol 31(3):169-217 (1994).
Padlan et al. Structure of an antibody-antigen complex: Crystal structure of the HyHEL-10 Fab-lysozyme complex. PNAS USA 86:5938-5942 (1989).
PCT/US2016/033644 International Preliminary Report on Patentability dated Nov. 30, 2017.
PCT/US2016/33644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
Presta et al. Humanization of an antibody directed against IgE. J Immunol 151:2623-2632 (1993).
Riechmann et al. Single domain antibodies: comparison of camel VH and camelised human VH domains. J Immunol Methods 231(1-2):25-38 (1999).
Rosok et al. A Combinatorial Library Strategy for the Rapid Humanization of Anticarcinoma BR96 Fab. J Biol Chem 271:22611-22618 (1996).
Rudikoff et al. Single amino acid substitution altering antigen-binding Specificity. PNAS USA 79:1979-1983 (1982).
Sims et al. A humanized CD18 antibody can block function without cell destruction. J Immunol 151:2296-2308 (1993).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Oct. 3, 2017.
U.S. Appl. No. 15/600,582 Office Action dated Nov. 16, 2017.
U.S. Appl. No. 15/704,620 Office Action dated Oct. 26, 2017.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol Biol 310:591-601 (2001).
Vaughan et al. Human antibodies by design. Nature Biotech 16:535-539 (1998).
Wu et al. Humanization of a murine monoclonal antibody by simultaneous optimization of framework and CDR residues. J. Mol. Biol. 294:151-162 (1999).
Holt et al. Anti-serum albumin domain antibodies for extending the half-lives of short lived drugs. Protien Eng Des Sel 21(5):283-288 (2008).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Nelson et al. Antibody fragments Hope and Hype. mAbs 2(1):77-83 (2010).
PCT/US2017/063121 International Search Report and Written Opinion dated Mar. 26, 2018.
PCT/US2017/063126 International Search Report and Written Opinion dated Apr. 5, 2018.
PCT/US2017056530 International Search Report and Written Opinion dated Jan. 23, 2018.
PCT/US2017/063121 Invitation to Pay Additional Fees dated Feb. 1, 2018.
PCT/US2017/063126 Invitation to Pay Additional Fees dated Feb. 1, 2018.
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Caldas et al. Humanization of the anti-CD18 antibody 6.7: an unexpected effect of a framework residue in binding to antigen. Mol Immunol. 39(15):941-952 (2003).
Chang et al. Loop-sequence features and stability determinants in antibody variable domains by high-throughput experiments. Structure 22(1):9-21 (2014).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Co-pending U.S. Appl. No. 16/159,545, filed Oct. 12, 2018.
Co-pending U.S. Appl. No. 16/159,554, filed Oct. 12, 2018.
Foote et al. Antibody Framework Residues Affecting the Conformation of the Hypervariable Loops. J. Mol. Biol. 224(2):487-99 (1992).
Giusti et al. Somatic diversification of S107 from an antiphosphocholine to an anti-DNA autoantibody is due to a single base change in its heavy chain variable region. PNAS USA 84(9):2926-30 (1987).
Goldman et al. Enhancing Stability of Camelid and Shark Single Domain Antibodies: An Overview. Front. Immunol. 8:865 (2017).
Gussow et al. Chapter 5: Humanization of Monoclonal Antibodies. Methods in Enzymology 203:99-121 (1991).
Holm et al. Functional mapping and single chain construction of the anti-cytokeratin 8 monoclonal antibody TS1. Mol Immunol 44(6):1075-1084 (2007).
Liu et al. A New Format of Single Chain Tri-specific Antibody with Diminished Molecular Size Efficiently Induces Ovarian Tumor Cell Killing. Biotechnology Letters 27(22):1821-1827 (2005).
Lu et al. In vitro and in vivo antitumor effect of a trivalent bispecific antibody targeting ErbB2 and CD16. Cancer Biol Ther. 7(11):1744-1750 (2008).
Mariuzza et al. The structural basis of antigen-antibody recognition. Annu Rev Biophys Biophys Chem 16:139-159 (1987).
Mueller et al. Improved pharmacokinetics of recombinant bispecific antibody molecules by fusion to human serum albumin. J Bio Chem 282(17):12650-12660 (2007).
Nunez-Prado et al. The coming of age of engineered multivalent antibodies. Drug Discovery Today 20(5):588-594 (2015).
PCT/US2018/014396 International Search Report and Written Opinion dated Jun. 14, 2018.
PCT/US2018/030983 International Search Report and Written Opinion dated Sep. 25, 2018.
PCT/US2018/032418 International Search Report and Written Opinion dated Sep. 24, 2018.
PCT/US2018/055659 International Search Report and Written Opinion dated Feb. 21, 2019.
PCT/US2018/055659 Invitation to Pay Additional Fees dated Dec. 19, 2018.
PCT/US2018/055682 International Search Report and Written Opinion dated Mar. 1, 2019.
PCT/US2018/055682 Invitation to Pay Additional Fees dated Jan. 8, 2019.
Running Deer et al. High-level expression of proteins in mammalian cells using transcription regulatory sequences from the Chinese hamster EF-1alpha gene. Biotechnol Prog. 20:880-889 (2004).
Saerens et al. Identification of a universal VHH framework to graft non-canonical antigen-binding loops of camel single-domain antibodies. J. Mol. Biol. 352(3):597-607 (2005).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Su et al. PSMA specific single chain antibody-mediated targeted knockdown of Notch1 inhibits human prostate cancer cell proliferation and tumor growth. Cancer Lett. 338 (2): 282-291 (2013).
Tiller et al. Facile Affinity Maturation of Antibody Variable Domains Using Natural Diversity Mutagenesis. Front. Immunol. 8:986 (2017).

(56) References Cited

OTHER PUBLICATIONS

Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
U.S. Appl. No. 15/600,264 Office Action dated Nov. 27, 2018.
U.S. Appl. No. 15/821,498 Office Action dated Oct. 26, 2018.
U.S. Appl. No. 15/977,968 Office Action dated Feb. 21, 2019.
U.S. Appl. No. 15/977,988 Preinterview First Office Action dated Jan. 25, 2019.
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).
Winkler et al. Changing the antigen binding specificity by single point mutations of an anti-p24 (HIV-1) antibody. J Immunol. 165(8):4505-4514 (2000).
Yu et al. Rationalization and design of the complementarity determining region sequences in an antibody-antigen recognition interface. PLoS One 7(3):e33340 (2012).
Zare et al. Production of nanobodies against prostate-specific membrane antigen (PSMA) recognizing LnCaP cells. Int. J. Biol. Markers 29(2):e169-e179 (2014).
Zhu et al. COMBODY: one-domain antibody multimer with improved avidity. Immunology and Cell Biology 88(6):667-675 (2010).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Chang et al. Molecular cloning of mesothelin, a differentiation antigen present on mesothelium, mesotheliomas, and ovarian cancers. PNAS USA 93:136-140 (1996).
Co-pending U.S. Appl. No. 15/977,968, filed May 11, 2018.
Co-pending U.S. Appl. No. 15/977,988, filed May 11, 2018.
Corso et al. Real-time detection of mesothelin in pancreatic cancer cell line supernatant using an acoustic wave immunosensor. Cancer Detect Prev 30:180-187 (2006).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).

Gross et al. Endowing T cells with antibody specificity using chimeric T cell receptors. FASEB J. 6(15):3370-3378 (1992).
Gubbels et al. Mesothelin-MUC16 binding is a high affinity, N-glycan dependent interaction that facilitates peritoneal metastasis of ovarian tumors. Mol Cancer 5:50 (2006).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prev 15:1014-1020 (2006).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Janssen letter—Submission under Rule 116 EPC. Submitted by Janssen Biotech to the European Patent Register on Mar. 18, 2016 in connection with their opposition to the EP2155783 patent (6 pages) (2016).
Kojima et al. Molecular cloning and expression of megakaryocyte potentiating factor cDNA. J Biol Chem 270:21984-21990 (1995).
Li et al. Development of novel tetravalent anti-CD20 antibodies with potent antitumor activity. Cancer Res 68:2400-2408 (2008).
Mirsky et al. Antibody-Specific Model of Amino Acid Substitution for Immunological Inferences from Alignments of Antibody Sequences. Mol. Biol. Evol. 32(3):806-819 (2014).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muul et al. Persistence and expression of the adenosine deaminase gene for 12 years and immune reaction to gene transfer components: long-term results of the first clinical gene therapy trial. Blood 101(7):2563-2569 (2003).
Ordonez. Application of mesothelin immunostaining in tumor diagnosis. Am J Surg Pathol 27:1418-1428 (2003).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2018/020185 International Search Report and Written Opinion dated Jun. 15, 2018.
PCT/US2018/020307 International Search Report and Written Opinion dated Aug. 24, 2018.
PCT/US2018/030983 Invitation to Pay Additional Fees dated Jul. 31, 2018.
PCT/US2018/032427 International Search Report and Written Opinion dated Sep. 13, 2018.
PCT/US2018/32418 Invitation to Pay Additional Fees dated Jul. 23, 2018.
PCT/US2018/32427 Invitation to Pay Additional Fees dated Jul. 24, 2018.
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Rump et al. Binding of ovarian cancer antigen CA125/MUC16 to mesothelin mediates cell adhesion. J Biol Chem 279:9190-9198 (2004).

(56) References Cited

OTHER PUBLICATIONS

Sadelain et al. Targeting tumours with genetically enhanced T lymphocytes. Nat Rev Cancer 3(1):35-45 (2003).
Tang et al. A human single-domain antibody elicits potent antitumor activity by targeting an epitope in mesothelin close to the cancer cell surface. Mol. Cancer Thera 12(4):416-426 (2013).
Thomas et al. Mesothelin-specific CD8(+) T cell responses provide evidence of in vivo cross-priming by antigen-presenting cells in vaccinated pancreatic cancer patients. J Exp Med 200:297-306 (2004).
U.S. Appl. No. 15/600,264 Office Action dated Apr. 26, 2018.
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Caldas et al. Design and synthesis of germline-based hemi-humanized single-chain Fv against the CD18 surface antigen. Protein Eng 13(5):353-360 (2000).
Carter et al. PD-1: PD-L inhibitory pathway affects both CD4(+) and CD8(+) T cells and is overcome by IL-2. Eur J Immunol 32:634-643 (2002).
Choi et al. Engineering of Immunoglobulin Fc heterodimers using yeast surface-displayed combinatorial Fc library screening. PLOS One 10(12):e0145349 (2015).
Chothia, et al. Conformations of immunoglobulin hypervariable regions. Nature 342(6252):877-83 (1989).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Dao et al. Targeting the intracellular WT1 oncogene with a therapeutic human antibody. Sci Transl Med 5(176):176ra33 (2013).
De Genst et al. Antibody repertoire development in camelids. Dev Comp Immunol 30(1-2):187-198 (2006).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).

Grupp et al. Chimeric antigen receptor-modified T cells for acute lymphoid leukemia. NEJM 368:1509-1518 (2013).
Haanen et al. Selective expansion of cross-reactive CD8(+) memory T cells by viral variants. J Exp Med 190(9):1319-1328 (1999).
Ho et al. Mesothelin is shed from tumor cells. Cancer Epidemiol Biomarkers Prev 15:1751 (2006).
Hollinger et al. "Diabodies": Small bivalent and bispecific antibody fragments. PNAS USA 90:6444 6448 (1993).
Huston et al. Protein engineering of antibody binding sites: recovery of specific activity in an anti-digoxin single-chain Fv analogue produced in *Escherichia coli*. PNAS USA 85(16):5879-5883 (1988).
Izumoto et al. Phase II clinical trial of Wilms tumor 1 peptide vaccination for patients with recurrent glioblastoma multiforme. J Neurosurg 108:963-971 (2008).
Jones et al. Replacing the complementarity-determining regions in a human antibody with those from a mouse. Nature 321:522-525 (1986).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Konishi et al. B7-H1 expression on non-small cell lung cancer cells and its relationship with tumor-infiltrating lymphocytes and their PD-1 expression. Clin Cancer Res 10:5094-5100 (2004).
Latchman et al. PD-L2 is a second ligand for PD-1 and inhibits T cell activation. Nat Immunol 2:261-268 (2001).
Lowman et al. Monovalent phage display: A method for selecting variant proteins from random libraries. Methods 3:205-216 (1991).
Milone et al. Chimeric receptors containing CD137 signal transduction domains mediate enhanced survival of T cells and increased antileukemic efficacy in vivo. Mol Ther 17(8):1453-1464 (2009).
Mumtaz et al. Design of liposomes for circumventing the reticuloendothelial cells. Glycobiology 5:505-10 (1991).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Padlan. A possible procedure for reducing the immunogenicity of antibody variable domains while preserving their ligand-binding properties. Mol Immunol 28(4-5):489-498 (1991).
PCT/US2019/052206 International Search Report and Written Opinion dated Feb. 14, 2020.
PCT/US2019/052206 Invitation to Pay Additional Fees dated Dec. 23, 2019.
PCT/US2019/052270 Invitation to Pay Additional Fees dated Jan. 9, 2020.
PCT/US2019/053017 International Search Report and Written Opinion dated Jan. 31, 2020.
PCT/US2019/053017 Invitation to Pay Additional Fees dated Nov. 27, 2019.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).

(56) References Cited

OTHER PUBLICATIONS

Presta. Antibody Engineering. Curr Op Struct Biol 2:593-596 (1992).
Riechmann et al. Reshaping human antibodies for therapy. Nature, 332.6162:323-7 (1988).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Sadelain et al. The basic principles of chimeric antigen receptor design. Cancer Discov. 3(4):388-98 (2013).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Tan et al. "Superhumanized" antibodies: reduction of immunogenic potential by complementarity-determining region grafting with human germline sequences: application to an anti-CD28. J Immunol 169:1119-1125 (2002).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/630,259 Office Action dated Dec. 30, 2019.
U.S. Appl. No. 16/159,545 Office Action dated Dec. 2, 2019.
U.S. Appl. No. 16/159,554 Office Action dated Oct. 1, 2019.
Van Der Linden et al. Induction of immune responses and molecular cloning of the heavy chain antibody repertoire of Lama glama. J Immunol Methods 240:185-195 (2000).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).

Willemsen et al. A phage display selected fab fragment with MHC class I-restricted specificity for MAGE-A1 allows for retargeting of primary human T lymphocytes. Gene Ther 8(21):1601-1608 (2001).
Yan et al. Engineering upper hinge improves stability and effector function of a human IgG1. J. Biol. Chem. 287:5891 (2012).
Yoshinaga et al. Ig L-chain shuffling for affinity maturation of phage library-derived human anti-human MCP-1 antibody blocking its chemotactic activity. J Biochem 143(5):593-601 (2008).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Schmidt et al. Cloning and Characterization of Canine Prostate-Specific Membrane Antigen. The Prostate 73:642-650 (2013).
U.S. Appl. No. 15/600,264 Office Action dated Apr. 25, 2019.
U.S. Appl. No. 15/821,498 Office Action dated May 3, 2019.
U.S. Appl. No. 15/977,988 Office Action dated Mar. 26, 2019.
Chen, Xiaoying et al. Fusion protein linkers: Property, design and functionality. Advanced Drug Delivery Reviews 65:1357-1369 (2013).
Dennis et al. Imaging Tumors with an Albumin-Binding Fab, a Novel Tumor-Targeting Agent. Cancer Res 67(1):254-61 (2007).
Hipp et al. A novel BCMA/CD3 bispecific T-cell engager for the treatment of multiple myeloma induces selective lysis in vitro and in vivo. Leukemia 31(8):1743-1751 (2017).
Hopp et al. The effects of affinity and valency of an albumin-binding domain (ABD) on the half-life of a single-chain diabody-ABD fusion protein. Protein Eng. Des. Sel. 23(11):827-34 (2010).
Laabi et al. The BCMA gene, preferentially expressed during B lymphoid maturation, is bidirectionally transcribed. Nucleic Acids Res 22(7):1147-1154 (1994).
Müller et al. Improved Pharmacokinetics of Recombinant Bispecific Antibody Molecules by Fusion to Human Serum Albumin. J. Biol. Chem. 282(17):12650-60 (2007).
Ramadoss et al. An Anti-B Cell Maturation Antigen bispecific Antibody for Multiple Myeloma. J. Ann. Chem. Soc. 137(16):5288-91 (2015).
Smirnova et al. Identification of new splice variants of the genes BAFF and BCMA. Mol. Immunol. 45 (4):1179-83 (2008).
Spiess et al. Alternative molecular formats and therapeutic applications for bispecific antibodies. Mol. Immunol. 67(2 Pt A):95-106 (2015).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Tijink et al. Improved tumor targeting of anti-epidermal growth factor receptor nanobodies through albumin binding: taking advantage of modular Nanobody technology. Mol. Cancer Ther. 7(8):2288-97 (2008).
U.S. Appl. No. 16/159,554 Office Action dated Jun. 7, 2019.
Muyldermans. Nanobodies: natural single-domain antibodies. Annu Rev Biochem, 82:775-797, 2013.
PCT/US2018/014396 International Preliminary Report on Patentability dated Aug. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
U.S. Appl. No. 15/977,988 Office Action dated Aug. 20, 2019.
U.S. Appl. No. 16/159,545 Office Action dated Aug. 6, 2019.
Co-pending U.S. Appl. No. 16/773,806, filed Jan. 27, 2020.
Co-pending U.S. Appl. No. 16/773,843, filed Jan. 27, 2020.
Co-pending U.S. Appl. No. 16/802,007, filed Feb. 26, 2020.
Harmsen et al. Properties, production, and applications of camelid single-domain antibody fragments. Appl. Microbiol. Biotechnol. 77:13-22 (2007).
U.S. Appl. No. 15/821,498 Office Action dated Apr. 21, 2020.
U.S. Appl. No. 16/583,070 Office Action dated Mar. 3, 2020.

(56) References Cited

OTHER PUBLICATIONS

Zabetakis et al. Contributions of the complementarity determining regions to the thermal stability of a single-domain antibody. PLoS One 8(10):e77678 (2013).

Zhang et al. New High Affinity Monoclonal Antibodies Recognize Non-Overlapping Epitopes on Mesothelin for Monitoring and Treating Mesothelioma. Sci Rep 5:9928 (2015).

* cited by examiner

| EC50 [pM] | LNCaP | 22Rv1 |
|---|---|---|
| TriTAC CD3 high aff. – C324 | 10 | 35 |
| TriTAC CD3 med. aff. – C339 | 87 | 561 |
| TriTAC CD3 low aff. – C325 | 1,389 | 7,460 |

| Dose Level | Animal ID | No points (lambda_z) | Terminal t1/2 (hr) | Cmax (ng/mL) | C0 (ng/mL) | AUC, 0-last (hr*ng/mL) | AUC, 0-inf (hr*ng/mL) | AUC %Extrapolated (%) | Clearance (mL/hr/kg) | Vss (L/kg) |
|---|---|---|---|---|---|---|---|---|---|---|
| 0.1 mg/kg | 63 | 6 | 91.6 | 245 | 253 | 10100 | 10300 | 1.8 | 9.68 | 1.15 |
| | 64 | 6 | 93.7 | 287 | 298 | 17500 | 17800 | 1.7 | 5.61 | 0.71 |
| | Mean | 6 | 92.6 | 266 | 276 | 13800 | 14100 | 1.8 | 7.64 | 0.93 |

| EC50 [pM] | LNCaP | LNCaP with HSA | HSA shift |
|---|---|---|---|
| PSMA p8 TriTAC C362 | 20 | 43 | 2x |
| PSMA HDS TriTAC C363 | 10 | 21 | 2x |
| PSMA HTS TriTAC C364 | 1.3 | 1.3 | 1x |
| PSMA BiTE | 20 | 9 | 0.5x |

- 22Rv1 human prostate cancer xenograft study in NOD/SCID/gamma mice reconstituted with resting, primary human T cells mixed at 1:1 ratio with cancer cells

| Cell line | EGFR expression | PSMA expression |
|---|---|---|
| LNCaP | Positive | Positive |
| KMS12BM | Negative | Negative |
| OVCAR8 | Positive | Negative |

TDCC assay with PSMA positive LNCaP tumor cells

SEQUENCE LISTING

<160> NUMBER OF SEQ ID NOS: 168

<210> SEQ ID NO 1
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Ile Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
                100                 105                 110

Ala Tyr Trp Gly Gln Gly Thr Leu Val Thr Val Ser Ser Gly Gly Gly

```
            115                 120                 125
Gly Ser Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Val Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
        210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
                245
```

<210> SEQ ID NO 2
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Glu Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Lys Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Leu Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
        210                 215                 220
```

Glu Ala Glu Tyr Tyr Cys Val Leu Trp Tyr Asp Asn Arg Trp Val Phe
225                 230                 235                 240

Gly Gly Gly Thr Lys Leu Thr Val Leu
                245

<210> SEQ ID NO 3
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser His Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Thr Gly Tyr Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Ser Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Ile Phe
225                 230                 235                 240

Gly Gly Gly Thr Lys Leu Thr Val Leu
                245

<210> SEQ ID NO 4
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

```
Ser Leu Lys Leu Ser Cys Ala Ala Ser Gly Phe Met Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Thr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Leu Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Ser Trp Val Phe
225                 230                 235                 240

Gly Gly Gly Thr Lys Leu Thr Val Leu
                245

<210> SEQ ID NO 5
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Lys Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125
```

Gly Ser Gly Gly Gly Ser Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Glu Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 6
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Tyr Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Gly Ser Ser Lys Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Glu Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Thr Leu Trp Tyr Ser Asn Arg Trp Val Phe

```
                    225                 230                 235                 240

Gly Gly Gly Thr Lys Leu Thr Val Leu
                245

<210> SEQ ID NO 7
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Thr Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly Gly
            180                 185                 190

Thr Tyr Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 8
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
```

```
                 20                  25                  30
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ala Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Gln Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Asp Gly Asn Tyr Pro Asn
                165                 170                 175

Trp Val Gln Gln Lys Pro Gly Gln Ala Pro Arg Gly Leu Ile Gly Gly
            180                 185                 190

Ile Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 9
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Val Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125
```

```
Gly Ser Gly Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Glu Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Ile Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245
```

<210> SEQ ID NO 10
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Pro Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Asn Glu Asp Thr Ala Val Tyr
                85                  90                  95

Tyr Cys Val Arg His Gly Asn Phe Asn Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Lys Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Met Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Ala Leu Trp Tyr Ser Asn Arg Trp Val Phe
225                 230                 235                 240
```

```
Gly Gly Gly Thr Lys Leu Thr Val Leu
            245

<210> SEQ ID NO 11
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Glu Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 12
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30
```

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asp Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr His Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Val Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 13
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Asn Tyr
                20                  25                  30

Ala Met Asn Trp Val Arg Gln Ala Pro Gly Lys Gly Leu Glu Trp Val
            35                  40                  45

Ala Arg Ile Arg Ser Gly Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Gln Thr Val Val

```
            130                 135                 140
Thr Gln Glu Pro Ser Leu Thr Val Ser Pro Gly Gly Thr Val Thr Leu
145                 150                 155                 160

Thr Cys Gly Ser Tyr Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Asn Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
                210                 215                 220

Glu Ala Glu Tyr Tyr Cys Val Leu Trp Tyr Ala Asn Arg Trp Val Phe
225                 230                 235                 240

Gly Gly Gly Thr Lys Leu Thr Val Leu
                245

<210> SEQ ID NO 14
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Glu Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Glu Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Leu Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Ser Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Gly Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
                210                 215                 220

Glu Ala Glu Tyr Tyr Cys Val Leu Trp Tyr Ser Asn Arg Trp Val Phe
225                 230                 235                 240
```

Gly Gly Gly Thr Lys Leu Thr Val Leu
            245

<210> SEQ ID NO 15
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Thr Phe Asn Lys Tyr Ala Met Asn
1               5                   10

<210> SEQ ID NO 17
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ile Arg Ser Lys Tyr Asn Asn Tyr Ala Thr Tyr Tyr Ala Asp Ser
1               5                   10                  15

Val Lys

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Gly Asn Phe Gly Asn Ser Tyr Ile Ser Tyr Trp Ala Tyr
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ser Ser Thr Gly Ala Val Thr Ser Gly Asn Tyr Pro Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Thr Lys Phe Leu Ala Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Trp Tyr Ser Asn Arg Trp Val
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

Gly Asn Thr Phe Asn Lys Tyr Ala Met Asn
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Phe Glu Phe Asn Lys Tyr Ala Met Asn
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Met Phe Asn Lys Tyr Ala Met Asn
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Phe Thr Tyr Asn Lys Tyr Ala Met Asn
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Asn Asn Tyr Ala Met Asn
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Phe Thr Phe Asn Gly Tyr Ala Met Asn
1               5                   10

<210> SEQ ID NO 28
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 28

Gly Phe Thr Phe Asn Thr Tyr Ala Met Asn
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Thr Phe Asn Glu Tyr Ala Met Asn
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Phe Thr Phe Asn Lys Tyr Pro Met Asn
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Thr Phe Asn Lys Tyr Ala Val Asn
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Phe Thr Phe Asn Lys Tyr Ala Ile Asn
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Phe Thr Phe Asn Lys Tyr Ala Leu Asn
1               5                   10
```

```
<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ile Arg Ser Gly Tyr Asn Asn Tyr Ala Thr Tyr Tyr Ala Asp Ser
1               5                   10                  15

Val Lys

<210> SEQ ID NO 35
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ile Arg Ser Lys Ser Asn Asn Tyr Ala Thr Tyr Tyr Ala Asp Ser
1               5                   10                  15

Val Lys

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ile Arg Ser Lys Tyr Asn Lys Tyr Ala Thr Tyr Tyr Ala Asp Ser
1               5                   10                  15

Val Lys

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ile Arg Ser Lys Tyr Asn Asn Tyr Glu Thr Tyr Tyr Ala Asp Ser
1               5                   10                  15

Val Lys

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ile Arg Ser Lys Tyr Asn Asn Tyr Ala Thr Glu Tyr Ala Asp Ser
1               5                   10                  15

Val Lys
```

```
<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ile Arg Ser Lys Tyr Asn Asn Tyr Ala Thr Tyr Tyr Lys Asp Ser
1               5                   10                  15

Val Lys

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg Ile Arg Ser Lys Tyr Asn Asn Tyr Ala Thr Tyr Tyr Ala Asp Glu
1               5                   10                  15

Val Lys

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ile Arg Ser Lys Tyr Asn Asn Tyr Ala Thr Tyr Tyr Ala Asp Ala
1               5                   10                  15

Val Lys

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ile Arg Ser Lys Tyr Asn Asn Tyr Ala Thr Tyr Tyr Ala Asp Gln
1               5                   10                  15

Val Lys

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ile Arg Ser Lys Tyr Asn Asn Tyr Ala Thr Tyr Tyr Ala Asp Asp
1               5                   10                  15
```

Val Lys

```
<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Ala Asn Phe Gly Asn Ser Tyr Ile Ser Tyr Trp Ala Tyr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

His Thr Asn Phe Gly Asn Ser Tyr Ile Ser Tyr Trp Ala Tyr
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

His Gly Asn Phe Asn Asn Ser Tyr Ile Ser Tyr Trp Ala Tyr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Gly Asn Phe Gly Asp Ser Tyr Ile Ser Tyr Trp Ala Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Gly Asn Phe Gly Asn Ser His Ile Ser Tyr Trp Ala Tyr
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 49

His Gly Asn Phe Gly Asn Ser Pro Ile Ser Tyr Trp Ala Tyr
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Gly Asn Phe Gly Asn Ser Gln Ile Ser Tyr Trp Ala Tyr
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Gly Asn Phe Gly Asn Ser Leu Ile Ser Tyr Trp Ala Tyr
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Gly Asn Phe Gly Asn Ser Gly Ile Ser Tyr Trp Ala Tyr
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Gly Asn Phe Gly Asn Ser Tyr Ile Ser Tyr Trp Ala Thr
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Ser Ser Thr Gly Ala Val Thr Ser Gly Asn Tyr Pro Asn
1               5                   10

<210> SEQ ID NO 55
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Glu Ser Thr Gly Ala Val Thr Ser Gly Asn Tyr Pro Asn
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ser Tyr Thr Gly Ala Val Thr Ser Gly Asn Tyr Pro Asn
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Ser Ser Phe Gly Ala Val Thr Ser Gly Asn Tyr Pro Asn
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser Ser Lys Gly Ala Val Thr Ser Gly Asn Tyr Pro Asn
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Ser Ser Ser Gly Ala Val Thr Ser Gly Asn Tyr Pro Asn
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Gly Ser Ser Thr Gly Tyr Val Thr Ser Gly Asn Tyr Pro Asn
1               5                   10
```

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Gly Ser Ser Thr Gly Ala Val Val Ser Gly Asn Tyr Pro Asn
1               5                   10
```

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Gly Ser Ser Thr Gly Ala Val Thr Asp Gly Asn Tyr Pro Asn
1               5                   10
```

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Gly Ser Ser Thr Gly Ala Val Thr Lys Gly Asn Tyr Pro Asn
1               5                   10
```

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gly Ser Ser Thr Gly Ala Val Thr His Gly Asn Tyr Pro Asn
1               5                   10
```

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Ser Ser Thr Gly Ala Val Thr Val Gly Asn Tyr Pro Asn
1               5                   10
```

<210> SEQ ID NO 66
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 66

Gly Ser Ser Thr Gly Ala Val Thr Ser Gly Tyr Tyr Pro Asn
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ile Lys Phe Leu Ala Pro
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Thr Glu Phe Leu Ala Pro
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Thr Tyr Phe Leu Ala Pro
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Thr Ser Phe Leu Ala Pro
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Thr Asn Phe Leu Ala Pro
1               5

```
<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Thr Lys Leu Leu Ala Pro
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Thr Lys Glu Leu Ala Pro
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Thr Lys Ile Leu Ala Pro
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Thr Lys Met Leu Ala Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Thr Lys Val Leu Ala Pro
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

```
Gly Thr Lys Phe Asn Ala Pro
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Thr Lys Phe Gly Ala Pro
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Thr Lys Phe Leu Val Pro
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Leu Trp Tyr Ser Asn Arg Trp Val
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Leu Trp Tyr Ser Asn Arg Trp Val
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Leu Trp Tyr Asp Asn Arg Trp Val
1               5

<210> SEQ ID NO 83
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 83

Val Leu Trp Tyr Ala Asn Arg Trp Val
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Leu Trp Tyr Ser Asn Ser Trp Val
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Leu Trp Tyr Ser Asn Arg Trp Ile
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Leu Trp Tyr Ser Asn Arg Trp Ala
1               5

<210> SEQ ID NO 87
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Leu Asn Trp Val Arg Gln Ala Pro Gly Lys Gly Leu Glu Trp Val
        35                  40                  45

Ala Arg Ile Arg Ser Lys Tyr Asn Asn Tyr Ala Thr Glu Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95
```

```
Tyr Cys Val Arg His Gly Asn Phe Gly Asn Ser Pro Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Asn Phe Leu Ala Pro Gly Thr Pro Glu Arg Phe Ser Gly Ser Leu
            195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Ala Phe
225                 230                 235                 240

Gly Gly Gly Thr Lys Leu Thr Val Leu
                245

<210> SEQ ID NO 88
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Glu Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Asp Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Gly Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Val Gly Asn Tyr Pro Asn
                165                 170                 175

Trp Val Gln Gln Lys Pro Gly Gln Ala Pro Arg Gly Leu Ile Gly Gly
                180                 185                 190

Thr Glu Phe Leu Ala Pro Gly Thr Pro Ala Arg Phe Ser Gly Ser Leu
```

```
                195                 200                 205
Leu Gly Gly Lys Ala Ala Leu Thr Leu Ser Gly Val Gln Pro Glu Asp
            210                 215                 220
Glu Ala Glu Tyr Tyr Cys Val Leu Trp Tyr Ser Asn Arg Trp Val Phe
225                 230                 235                 240
Gly Gly Gly Thr Lys Leu Thr Val Leu
                245
```

<210> SEQ ID NO 89
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Arg Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser
        115
```

<210> SEQ ID NO 90
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Lys Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ala Asp Thr Leu Tyr Ala Asp Ser Leu
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Lys Ser Ser Gln Gly Thr Leu Val Thr
            100                 105                 110
Val Ser Ser
```

<210> SEQ ID NO 91
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Tyr Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115

<210> SEQ ID NO 92
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 93
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115

<210> SEQ ID NO 94
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

```
Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Phe Thr Phe Ser Ser Phe Gly Met Ser
1               5                   10

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Ile Ser Gly Ser Gly Ser Asp Thr Leu Tyr Ala Asp Ser Val Lys
1               5                   10                  15

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Ser Leu Ser Arg
1               5

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Phe Thr Phe Ser Arg Phe Gly Met Ser
1               5                   10

<210> SEQ ID NO 100
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 100

Gly Phe Thr Phe Ser Lys Phe Gly Met Ser
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Thr Tyr Ser Ser Phe Gly Met Ser
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Ile Ser Gly Ser Gly Ala Asp Thr Leu Tyr Ala Asp Ser Leu Lys
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Ile Ser Gly Ser Gly Thr Asp Thr Leu Tyr Ala Asp Ser Val Lys
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ile Ser Gly Ser Gly Arg Asp Thr Leu Tyr Ala Asp Ser Val Lys
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ile Ser Gly Ser Gly Ser Asp Thr Leu Tyr Ala Glu Ser Val Lys
1               5                   10                  15
```

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ile Ser Gly Ser Gly Thr Asp Thr Leu Tyr Ala Glu Ser Val Lys
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Ile Ser Gly Ser Gly Arg Asp Thr Leu Tyr Ala Glu Ser Val Lys
1               5                   10                  15

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Ser Leu Ser Lys
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Ser Leu Ser Val
1               5

<210> SEQ ID NO 110
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 111
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 112
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
      115

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser
            100                 105                 110

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Phe Met Ile Ser Glu Tyr His Met His
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Phe Met Ile Ser Pro Tyr Ser Met His
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Phe Met Ile Ser Pro Tyr His Met His
1               5                   10

-continued

```
<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Ile Asn Pro Ala Gly Thr Thr Asp Tyr Ala Glu Ser Val Lys Gly
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Ile Asn Pro Ala Lys Thr Thr Asp Tyr Ala Glu Ser Val Lys Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Ile Asn Pro Ala Gly Gln Thr Asp Tyr Ala Glu Ser Val Lys Gly
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Ile Asn Pro Ala Gly Thr Thr Asp Tyr Ala Glu Tyr Val Lys Gly
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Ile Asn Pro Ala Lys Thr Thr Asp Tyr Ala Glu Ser Val Lys Gly
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122
```

Asp Ile Asn Pro Ala Gly Gln Thr Asp Tyr Ala Glu Ser Val Lys Gly
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Ile Asn Pro Ala Gly Thr Thr Asp Tyr Ala Glu Tyr Val Lys Gly
1               5                   10                  15

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Ser Tyr Gly Tyr
1               5

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Phe Met Ile Ser Glu Tyr Ser Met His
1               5                   10

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Ile Asn Pro Ala Gly Thr Thr Asp Tyr Ala Glu Ser Val Lys Gly
1               5                   10                  15

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Gly Tyr Gly Tyr
1               5

<210> SEQ ID NO 128
<211> LENGTH: 111
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Gly Tyr Gly Tyr Arg Gly Gln Gly Thr Leu Val Thr Val Ser Ser
            100                 105                 110

<210> SEQ ID NO 129
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45
```

```
Ser Thr Ile Asn Pro Ala Gly Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Ser Tyr Gly Tyr Arg Gly Gln Gly Thr Leu Val Thr Val Ser Ser
                100                 105                 110
```

<210> SEQ ID NO 131
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Glu Val Gln Leu Val Glu Ser Gly Gly Gly Leu Val Gln Pro Gly Gly
 1                5                  10                  15

Ser Leu Arg Leu Ser Cys Ala Ala Ser Arg Phe Met Ile Ser Glu Tyr
                 20                  25                  30

Ser Met His Trp Val Arg Gln Ala Pro Gly Lys Gly Leu Glu Trp Val
             35                  40                  45

Ser Thr Ile Asn Pro Ala Lys Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Ser Tyr Gly Tyr Arg Gly Gln Gly Thr Leu Val Thr Val Ser Ser
                100                 105                 110
```

<210> SEQ ID NO 132
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Glu Val Gln Leu Val Glu Ser Gly Gly Gly Leu Val Gln Pro Gly Gly
 1                5                  10                  15

Ser Leu Arg Leu Ser Cys Ala Ala Ser Arg Phe Met Ile Ser Pro Tyr
                 20                  25                  30

Ser Met His Trp Val Arg Gln Ala Pro Gly Lys Gly Leu Glu Trp Val
             35                  40                  45

Ser Thr Ile Asn Pro Ala Gly Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Gly Tyr Gly Tyr Arg Gly Gln Gly Thr Leu Val Thr Val Ser Ser
                100                 105                 110
```

<210> SEQ ID NO 133
<211> LENGTH: 111

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Gln Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Gly Tyr Gly Tyr Arg Gly Gln Gly Thr Leu Val Thr Val Ser Ser
            100                 105                 110

<210> SEQ ID NO 134
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Tyr Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Gly Tyr Gly Tyr Arg Gly Gln Gly Thr Leu Val Thr Val Ser Ser
            100                 105                 110

<210> SEQ ID NO 135
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
```

```
                35                  40                  45

Ser Asp Ile Asn Pro Ala Lys Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Ser Tyr Gly Tyr Arg Gly Gln Gly Thr Leu Val Thr Val Ser Ser
                100                 105                 110

<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Val Gln Pro Gly Gly
 1               5                  10                  15

Ser Leu Arg Leu Ser Cys Ala Ala Ser Arg Phe Met Ile Ser Pro Tyr
                 20                  25                  30

His Met His Trp Val Arg Gln Ala Pro Gly Lys Gly Leu Glu Trp Val
                 35                  40                  45

Ser Asp Ile Asn Pro Ala Gly Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Ser Tyr Gly Tyr Arg Gly Gln Gly Thr Leu Val Thr Val Ser Ser
                100                 105                 110

<210> SEQ ID NO 137
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Val Gln Leu Val Glu Ser Gly Gly Gly Leu Val Gln Pro Gly Gly
 1               5                  10                  15

Ser Leu Arg Leu Ser Cys Ala Ala Ser Arg Phe Met Ile Ser Glu Tyr
                 20                  25                  30

His Met His Trp Val Arg Gln Ala Pro Gly Lys Gly Leu Glu Trp Val
                 35                  40                  45

Ser Asp Ile Asn Pro Ala Gly Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Asp
                 85                  90                  95

Ser Tyr Gly Tyr Arg Gly Gln Gly Thr Leu Val Thr Val Ser Ser
                100                 105                 110
```

```
<210> SEQ ID NO 138
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Tyr Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser
            100                 105                 110

<210> SEQ ID NO 139
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Ser Val Lys
50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser
            100                 105                 110

<210> SEQ ID NO 140
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30
```

His Met His Trp Val Arg Gln Ala Pro Gly Lys Gly Leu Glu Trp Val
            35                  40                  45

Ser Thr Ile Asn Pro Ala Gly Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Asp
            85                  90                  95

Ser Tyr Gly Tyr Arg Gly Gln Gly Thr Gln Val Thr Val Ser Ser
            100                 105                 110

<210> SEQ ID NO 141
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Gln Pro Gly Gly
 1               5                  10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
            35                  40                  45

Ser Thr Ile Asn Pro Ala Gly Thr Thr Asp Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Val Tyr Tyr Cys Asp
            85                  90                  95

Gly Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
            115                 120                 125

Gly Gly Leu Val Gln Pro Gly Asn Ser Leu Arg Leu Ser Cys Ala Ala
 130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
            165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
 195                 200                 205

Glu Asp Thr Ala Val Tyr Tyr Cys Thr Ile Gly Gly Ser Leu Ser Val
            210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
            245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly

```
                275                 280                 285
Leu Glu Trp Val Ala Arg Ile Arg Ser Lys Tyr Asn Asn Tyr Ala Thr
        290                 295                 300
Tyr Tyr Ala Asp Gln Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
                325                 330                 335
Thr Ala Val Tyr Tyr Cys Val Arg His Ala Asn Phe Gly Asn Ser Tyr
            340                 345                 350
Ile Ser Tyr Trp Ala Tyr Trp Gly Gln Gly Thr Leu Val Thr Val Ser
                355                 360                 365
Ser Gly Gly Gly Gly Ser Gly Gly Gly Ser Gly Gly Gly Gly Ser
        370                 375                 380
Gln Thr Val Val Thr Gln Glu Pro Ser Leu Thr Val Ser Pro Gly Gly
385                 390                 395                 400
Thr Val Thr Leu Thr Cys Ala Ser Ser Thr Gly Ala Val Thr Ser Gly
                405                 410                 415
Asn Tyr Pro Asn Trp Val Gln Gln Lys Pro Gly Gln Ala Pro Arg Gly
            420                 425                 430
Leu Ile Gly Gly Thr Lys Phe Leu Val Pro Gly Thr Pro Ala Arg Phe
        435                 440                 445
Ser Gly Ser Leu Leu Gly Gly Lys Ala Ala Leu Thr Leu Ser Gly Val
        450                 455                 460
Gln Pro Glu Asp Glu Ala Glu Tyr Tyr Cys Thr Leu Trp Tyr Ser Asn
465                 470                 475                 480
Arg Trp Val Phe Gly Gly Gly Thr Lys Leu Thr Val Leu His His His
                485                 490                 495
His His His
```

<210> SEQ ID NO 142
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Glu Val Gln Leu Val Glu Ser Gly Gly Gly Leu Val Gln Pro Gly Gly
1               5                   10                  15
Ser Leu Thr Leu Ser Cys Ala Ala Ser Arg Phe Met Ile Ser Glu Tyr
            20                  25                  30
Ser Met His Trp Val Arg Gln Ala Pro Gly Lys Gly Leu Glu Trp Val
        35                  40                  45
Ser Thr Ile Asn Pro Ala Gly Thr Thr Asp Tyr Ala Glu Ser Val Lys
    50                  55                  60
Gly Arg Phe Thr Ile Ser Arg Asp Asn Ala Lys Asn Thr Leu Tyr Leu
65                  70                  75                  80
Gln Met Asn Ser Leu Lys Pro Glu Asp Thr Ala Val Tyr Tyr Cys Asp
                85                  90                  95
Gly Tyr Gly Tyr Arg Gly Gln Gly Thr Gln Val Thr Val Ser Ser Gly
            100                 105                 110
Gly Gly Gly Ser Gly Gly Gly Ser Glu Val Gln Leu Val Glu Ser Gly
        115                 120                 125
Gly Gly Leu Val Gln Pro Gly Asn Ser Leu Arg Leu Ser Cys Ala Ala
```

```
                130              135              140
Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Asn Tyr Ala Met Asn Trp Val Arg Gln Ala Pro Gly Lys Gly
        275                 280                 285

Leu Glu Trp Val Ala Arg Ile Arg Ser Gly Tyr Asn Asn Tyr Ala Thr
290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Gly Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
370                 375                 380

Gln Thr Val Val Thr Gln Glu Pro Ser Leu Thr Val Ser Pro Gly Gly
385                 390                 395                 400

Thr Val Thr Leu Thr Cys Gly Ser Tyr Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Asn Ala Pro Gly Thr Pro Ala Arg Phe
        435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Val Leu Trp Tyr Ala Asn
465                 470                 475                 480

Arg Trp Val Phe Gly Gly Gly Thr Lys Leu Thr Val Leu His His His
                485                 490                 495

His His His

<210> SEQ ID NO 143
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 143

Glu Val Gln Leu Val Glu Ser Gly Gly Gly Leu Val Gln Pro Gly Gly
1               5                   10                  15
Ser Leu Thr Leu Ser Cys Ala Ala Ser Arg Phe Met Ile Ser Glu Tyr
            20                  25                  30
Ser Met His Trp Val Arg Gln Ala Pro Gly Lys Gly Leu Glu Trp Val
        35                  40                  45
Ser Thr Ile Asn Pro Ala Gly Thr Thr Asp Tyr Ala Glu Ser Val Lys
    50                  55                  60
Gly Arg Phe Thr Ile Ser Arg Asp Asn Ala Lys Asn Thr Leu Tyr Leu
65                  70                  75                  80
Gln Met Asn Ser Leu Lys Pro Glu Asp Thr Ala Val Tyr Tyr Cys Asp
                85                  90                  95
Gly Tyr Gly Tyr Arg Gly Gln Gly Thr Gln Val Thr Val Ser Ser Gly
            100                 105                 110
Gly Gly Gly Ser Gly Gly Gly Ser Glu Val Gln Leu Val Glu Ser Gly
        115                 120                 125
Gly Gly Leu Val Gln Pro Gly Asn Ser Leu Arg Leu Ser Cys Ala Ala
    130                 135                 140
Ser Gly Phe Thr Phe Ser Lys Phe Gly Met Ser Trp Val Arg Gln Ala
145                 150                 155                 160
Pro Gly Lys Gly Leu Glu Trp Val Ser Ser Ile Ser Gly Ser Gly Arg
                165                 170                 175
Asp Thr Leu Tyr Ala Asp Ser Val Lys Gly Arg Phe Thr Ile Ser Arg
            180                 185                 190
Asp Asn Ala Lys Thr Thr Leu Tyr Leu Gln Met Asn Ser Leu Arg Pro
        195                 200                 205
Glu Asp Thr Ala Val Tyr Tyr Cys Thr Ile Gly Gly Ser Leu Ser Val
    210                 215                 220
Ser Ser Gln Gly Thr Leu Val Thr Val Ser Ser Gly Gly Gly Gly Ser
225                 230                 235                 240
Gly Gly Gly Ser Glu Val Gln Leu Val Glu Ser Gly Gly Gly Leu Val
                245                 250                 255
Gln Pro Gly Gly Ser Leu Lys Leu Ser Cys Ala Ala Ser Gly Phe Glu
            260                 265                 270
Phe Asn Lys Tyr Ala Met Asn Trp Val Arg Gln Ala Pro Gly Lys Gly
        275                 280                 285
Leu Glu Trp Val Ala Arg Ile Arg Ser Lys Tyr Asn Asn Tyr Glu Thr
    290                 295                 300
Tyr Tyr Ala Asp Ser Val Lys Asp Arg Phe Thr Ile Ser Arg Asp Asp
305                 310                 315                 320
Ser Lys Asn Thr Ala Tyr Leu Gln Met Asn Asn Leu Lys Thr Glu Asp
                325                 330                 335
Thr Ala Val Tyr Tyr Cys Val Arg His Gly Asn Phe Gly Asn Ser Leu
            340                 345                 350
Ile Ser Tyr Trp Ala Tyr Trp Gly Gln Gly Thr Leu Val Thr Val Ser
        355                 360                 365
Ser Gly Gly Gly Gly Ser Gly Gly Gly Ser Gly Gly Gly Gly Ser
    370                 375                 380
Gln Thr Val Val Thr Gln Glu Pro Ser Leu Thr Val Ser Pro Gly Gly
385                 390                 395                 400
Thr Val Thr Leu Thr Cys Gly Ser Ser Gly Ala Val Thr Ser Gly
                405                 410                 415

```
Asn Tyr Pro Asn Trp Val Gln Gln Lys Pro Gly Gln Ala Pro Arg Gly
            420                 425                 430

Leu Ile Gly Gly Thr Lys Phe Gly Ala Pro Gly Thr Pro Ala Arg Phe
            435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Val Leu Trp Tyr Ser Asn
465                 470                 475                 480

Arg Trp Val Phe Gly Gly Thr Lys Leu Thr Val Leu His His His
                485                 490                 495

His His His

<210> SEQ ID NO 144
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Gly Tyr Gly Tyr Arg Gly Gln Gly Thr Gln Val Thr Val Ser Ser Gly
            100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Ser Phe Gly Met Ser Trp Val Arg Gln Ala
145                 150                 155                 160

Pro Gly Lys Gly Leu Glu Trp Val Ser Ser Ile Ser Gly Ser Gly Ser
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Arg
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270
```

```
Phe Asn Lys Tyr Ala Met Asn Trp Val Arg Gln Ala Pro Gly Lys Gly
            275                 280                 285

Leu Glu Trp Val Ala Arg Ile Arg Ser Lys Tyr Asn Asn Tyr Ala Thr
290                 295                 300

Tyr Tyr Ala Asp Ser Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
            325                 330                 335

Thr Ala Val Tyr Tyr Cys Val Arg His Gly Asn Phe Gly Asn Ser Tyr
            340                 345                 350

Ile Ser Tyr Trp Ala Tyr Trp Gly Gln Gly Thr Leu Val Thr Val Ser
            355                 360                 365

Ser Gly Gly Gly Gly Ser Gly Gly Gly Gly Ser Gly Gly Gly Gly Ser
            370                 375                 380

Gln Thr Val Val Thr Gln Glu Pro Ser Leu Thr Val Ser Pro Gly Gly
385                 390                 395                 400

Thr Val Thr Leu Thr Cys Gly Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Ala Pro Gly Thr Pro Ala Arg Phe
            435                 440                 445

Ser Gly Ser Leu Leu Gly Gly Lys Ala Ala Leu Thr Leu Ser Gly Val
450                 455                 460

Gln Pro Glu Asp Glu Ala Glu Tyr Tyr Cys Val Leu Trp Tyr Ser Asn
465                 470                 475                 480

Arg Trp Val Phe Gly Gly Gly Thr Lys Leu Thr Val Leu His His His
            485                 490                 495

His His His
```

<210> SEQ ID NO 145
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 145

```
Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Met Ile Ser Glu Tyr
            20                  25                  30

Ser Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
            85                  90                  95

Gly Tyr Gly Tyr Arg Gly Gln Gly Thr Leu Val Thr Val Ser Ser Gly
            100                 105                 110

Gly Gly Gly Ser Gly Gly Gly Gly Ser Glu Val Gln Leu Val Glu Ser Gly
        115                 120                 125
```

Gly Gly Leu Val Gln Pro Gly Asn Ser Leu Arg Leu Ser Cys Ala Ala
        130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 146
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Glu Val Gln Leu Val Glu Ser Gly Gly Gly Leu Val Gln Pro Gly Gly
 1               5                  10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Asp Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser Gly
            100                 105                 110

Gly Gly Gly Ser Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400
```

```
Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
            435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His
```

<210> SEQ ID NO 147
<211> LENGTH: 499
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asp
                85                  90                  95

Ser Tyr Gly Tyr Arg Gly Gln Gly Thr Gln Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255
```

Gln Pro Gly Gly Ser Leu Lys Leu Ser Cys Ala Ala Ser Gly Phe Thr
                260                 265                 270

Phe Asn Lys Tyr Ala Ile Asn Trp Val Arg Gln Ala Pro Gly Lys Gly
            275                 280                 285

Leu Glu Trp Val Ala Arg Ile Arg Ser Lys Tyr Asn Asn Tyr Ala Thr
        290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
        355                 360                 365

Ser Gly Gly Gly Gly Ser Gly Gly Gly Gly Ser Gly Gly Gly Gly Ser
    370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
            405                 410                 415

Asn Tyr Pro Asn Trp Val Gln Gln Lys Pro Gly Gln Ala Pro Arg Gly
        420                 425                 430

Leu Ile Gly Gly Thr Lys Phe Leu Val Pro Gly Thr Pro Ala Arg Phe
    435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
            485                 490                 495

His His His

<210> SEQ ID NO 148
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Gly Phe Pro Leu Leu Arg His Gly Ala Met Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Lys
145                 150                 155                 160

Ala Ser Gln Asn Val Asp Thr Asn Val Ala Trp Tyr Gln Lys Pro
                165                 170                 175

Gly Gln Ala Pro Lys Ser Leu Ile Tyr Ser Ala Ser Tyr Arg Tyr Ser
            180                 185                 190

Asp Val Pro Ser Arg Phe Ser Gly Ser Ala Ser Gly Thr Asp Phe Thr
        195                 200                 205

Leu Thr Ile Ser Ser Val Gln Ser Glu Asp Phe Ala Thr Tyr Tyr Cys
    210                 215                 220

Gln Gln Tyr Asp Ser Tyr Pro Tyr Thr Phe Gly Gly Thr Lys Leu
225                 230                 235                 240

Glu Ile Lys Ser Gly Gly Gly Gly Ser Glu Val Gln Leu Val Glu Ser
            245                 250                 255

Gly Gly Gly Leu Val Gln Pro Gly Gly Ser Leu Lys Leu Ser Cys Ala
        260                 265                 270

Ala Ser Gly Phe Thr Phe Asn Lys Tyr Ala Met Asn Trp Val Arg Gln
    275                 280                 285

Ala Pro Gly Lys Gly Leu Glu Trp Val Ala Arg Ile Arg Ser Lys Tyr
290                 295                 300

Asn Asn Tyr Ala Thr Tyr Tyr Ala Asp Ser Val Lys Asp Arg Phe Thr
305                 310                 315                 320

Ile Ser Arg Asp Asp Ser Lys Asn Thr Ala Tyr Leu Gln Met Asn Asn
                325                 330                 335

Leu Lys Thr Glu Asp Thr Ala Val Tyr Tyr Cys Val Arg His Gly Asn
            340                 345                 350

Phe Gly Asn Ser Tyr Ile Ser Tyr Trp Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Gln Thr Val Val Thr Gln Glu Pro Ser Leu Thr
385                 390                 395                 400

Val Ser Pro Gly Gly Thr Val Thr Leu Thr Cys Gly Ser Ser Thr Gly
                405                 410                 415

Ala Val Thr Ser Gly Asn Tyr Pro Asn Trp Val Gln Gln Lys Pro Gly
            420                 425                 430

Gln Ala Pro Arg Gly Leu Ile Gly Gly Thr Lys Phe Leu Ala Pro Gly
        435                 440                 445

Thr Pro Ala Arg Phe Ser Gly Ser Leu Leu Gly Gly Lys Ala Ala Leu
    450                 455                 460

Thr Leu Ser Gly Val Gln Pro Glu Asp Glu Ala Glu Tyr Tyr Cys Val
465                 470                 475                 480

Leu Trp Tyr Ser Asn Arg Trp Val Phe Gly Gly Gly Thr Lys Leu Thr
                485                 490                 495

Val Leu His His His His His His
            500

<210> SEQ ID NO 149
<211> LENGTH: 512
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 149

Gln Val Lys Leu Glu Glu Ser Gly Gly Ser Val Gln Thr Gly Gly
1               5                   10                  15

Ser Leu Arg Leu Thr Cys Ala Ala Ser Gly Arg Thr Ser Arg Ser Tyr
            20                  25                  30

Gly Met Gly Trp Phe Arg Gln Ala Pro Gly Lys Glu Arg Glu Phe Val
            35                  40                  45

Ser Gly Ile Ser Trp Arg Gly Asp Ser Thr Gly Tyr Ala Asp Ser Val
        50                  55                  60

Lys Gly Arg Phe Thr Ile Ser Arg Asp Asn Ala Lys Asn Thr Val Asp
65                  70                  75                  80

Leu Gln Met Asn Ser Leu Lys Pro Glu Asp Thr Ala Ile Tyr Tyr Cys
                85                  90                  95

Ala Ala Ala Ala Gly Ser Ala Trp Tyr Gly Thr Leu Tyr Glu Tyr Asp
            100                 105                 110

Tyr Trp Gly Gln Gly Thr Gln Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Gly Gly Gly Gly Ser Gly Gly Gly
                245                 250                 255

Ser Glu Val Gln Leu Val Glu Ser Gly Gly Gly Leu Val Gln Pro Gly
            260                 265                 270

Gly Ser Leu Lys Leu Ser Cys Ala Ala Ser Gly Phe Thr Phe Asn Lys
        275                 280                 285

Tyr Ala Met Asn Trp Val Arg Gln Ala Pro Gly Lys Gly Leu Glu Trp
    290                 295                 300

Val Ala Arg Ile Arg Ser Lys Tyr Asn Asn Tyr Ala Thr Tyr Tyr Ala
305                 310                 315                 320

Asp Ser Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Gly Asn Phe Gly Asn Ser Tyr Ile Ser Tyr
        355                 360                 365

Trp Ala Tyr Trp Gly Gln Gly Thr Leu Val Thr Val Ser Ser Gly Gly
    370                 375                 380

```
Gly Gly Ser Gly Gly Gly Ser Gly Gly Gly Ser Gln Thr Val
385                 390                 395                 400

Val Thr Gln Glu Pro Ser Leu Thr Val Ser Pro Gly Gly Thr Val Thr
                405                 410                 415

Leu Thr Cys Gly Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
        435                 440                 445

Gly Thr Lys Phe Leu Ala Pro Gly Thr Pro Ala Arg Phe Ser Gly Ser
450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Val Leu Trp Tyr Ser Asn Arg Trp Val
                485                 490                 495

Phe Gly Gly Gly Thr Lys Leu Thr Val Leu His His His His His His
            500                 505                 510
```

<210> SEQ ID NO 150
<211> LENGTH: 508
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Gln Val Gln Leu Val Glu Ser Gly Gly Val Val Gln Ala Gly Arg
1               5                   10                  15

Ser Leu Thr Leu Ser Cys Ala Tyr Ser Gly Val Thr Val Asn Val Tyr
                20                  25                  30

Arg Met Gly Trp Phe Arg Gln Ala Pro Gly Lys Glu Arg Glu Phe Val
            35                  40                  45

Ala Asn Ile Asn Trp Ser Gly Asn Asn Arg Asp Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Glu Lys Pro Gly Arg Leu Gly Glu Tyr Asp Tyr Gly Ser Gln
            100                 105                 110

Gly Thr Leu Val Thr Val Ser Ser Gly Gly Gly Ser Gly Gly Gly
        115                 120                 125

Ser Glu Val Gln Leu Val Glu Ser Gly Gly Gly Leu Val Gln Pro Gly
130                 135                 140

Asn Ser Leu Arg Leu Ser Cys Ala Ala Ser Gly Phe Thr Phe Ser Lys
145                 150                 155                 160

Phe Gly Met Ser Trp Val Arg Gln Ala Pro Gly Lys Gly Leu Glu Trp
                165                 170                 175

Val Ser Ser Ile Ser Gly Ser Gly Arg Asp Thr Leu Tyr Ala Asp Ser
            180                 185                 190

Val Lys Gly Arg Phe Thr Ile Ser Arg Asp Asn Ala Lys Thr Thr Leu
        195                 200                 205

Tyr Leu Gln Met Asn Ser Leu Arg Pro Glu Asp Thr Ala Val Tyr Tyr
210                 215                 220

Cys Thr Ile Gly Gly Ser Leu Ser Val Ser Ser Gln Gly Thr Leu Val
225                 230                 235                 240
```

Thr Val Ser Ser Gly Gly Gly Ser Gly Gly Ser Glu Val Gln
            245                 250                 255

Leu Val Glu Ser Gly Gly Leu Val Gln Pro Gly Ser Leu Lys
            260                 265                 270

Leu Ser Cys Ala Ala Ser Gly Phe Thr Phe Asn Lys Tyr Ala Ile Asn
            275                 280                 285

Trp Val Arg Gln Ala Pro Gly Lys Gly Leu Glu Trp Val Ala Arg Ile
            290                 295                 300

Arg Ser Lys Tyr Asn Asn Tyr Ala Thr Tyr Tyr Ala Asp Gln Val Lys
305                 310                 315                 320

Asp Arg Phe Thr Ile Ser Arg Asp Asp Ser Lys Asn Thr Ala Tyr Leu
            325                 330                 335

Gln Met Asn Asn Leu Lys Thr Glu Asp Thr Ala Val Tyr Tyr Cys Val
            340                 345                 350

Arg His Ala Asn Phe Gly Asn Ser Tyr Ile Ser Tyr Trp Ala Tyr Trp
            355                 360                 365

Gly Gln Gly Thr Leu Val Thr Val Ser Ser Gly Gly Gly Ser Gly
            370                 375                 380

Gly Gly Ser Gly Gly Gly Ser Gln Thr Val Thr Gln Glu
385                 390                 395                 400

Pro Ser Leu Thr Val Ser Pro Gly Gly Thr Val Thr Leu Thr Cys Ala
            405                 410                 415

Ser Ser Thr Gly Ala Val Thr Ser Gly Asn Tyr Pro Asn Trp Val Gln
            420                 425                 430

Gln Lys Pro Gly Gln Ala Pro Arg Gly Leu Ile Gly Gly Thr Lys Phe
            435                 440                 445

Leu Val Pro Gly Thr Pro Ala Arg Phe Ser Gly Ser Leu Leu Gly Gly
            450                 455                 460

Lys Ala Ala Leu Thr Leu Ser Gly Val Gln Pro Glu Asp Glu Ala Glu
465                 470                 475                 480

Tyr Tyr Cys Thr Leu Trp Tyr Ser Asn Arg Trp Val Phe Gly Gly Gly
            485                 490                 495

Thr Lys Leu Thr Val Leu His His His His His His
            500                 505

<210> SEQ ID NO 151
<211> LENGTH: 508
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Glu Ser Gly Gly Gly Val Val Gln Ala Gly Arg
1               5                   10                  15

Ser Leu Arg Leu Ser Cys Ala Tyr Ser Gly Val Thr Val Asn Val Tyr
            20                  25                  30

Arg Met Gly Trp Phe Arg Gln Ala Pro Gly Lys Glu Arg Glu Phe Val
            35                  40                  45

Ala Asn Ile Asn Trp Ser Gly Asn Asn Arg Asp Tyr Ala Asp Ser Val
            50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                    85                  90                  95
Ala Ser Glu Lys Pro Gly Arg Leu Gly Glu Tyr Asp Tyr Gly Ser Gln
            100                 105                 110

Gly Thr Leu Val Thr Val Ser Ser Gly Gly Gly Ser Gly Gly Gly
            115                 120                 125

Ser Glu Val Gln Leu Val Glu Ser Gly Gly Gly Leu Val Gln Pro Gly
130                 135                 140

Asn Ser Leu Arg Leu Ser Cys Ala Ala Ser Gly Phe Thr Phe Ser Lys
145                 150                 155                 160

Phe Gly Met Ser Trp Val Arg Gln Ala Pro Gly Lys Gly Leu Glu Trp
                165                 170                 175

Val Ser Ser Ile Ser Gly Ser Gly Arg Asp Thr Leu Tyr Ala Asp Ser
                180                 185                 190

Val Lys Gly Arg Phe Thr Ile Ser Arg Asp Asn Ala Lys Thr Thr Leu
            195                 200                 205

Tyr Leu Gln Met Asn Ser Leu Arg Pro Glu Asp Thr Ala Val Tyr Tyr
            210                 215                 220

Cys Thr Ile Gly Gly Ser Leu Ser Val Ser Ser Gln Gly Thr Leu Val
225                 230                 235                 240

Thr Val Ser Ser Gly Gly Gly Gly Ser Gly Gly Gly Ser Glu Val Gln
                245                 250                 255

Leu Val Glu Ser Gly Gly Gly Leu Val Gln Pro Gly Gly Ser Leu Lys
            260                 265                 270

Leu Ser Cys Ala Ala Ser Gly Phe Thr Phe Asn Lys Tyr Ala Ile Asn
            275                 280                 285

Trp Val Arg Gln Ala Pro Gly Lys Gly Leu Glu Trp Val Ala Arg Ile
            290                 295                 300

Arg Ser Lys Tyr Asn Asn Tyr Ala Thr Tyr Tyr Ala Asp Gln Val Lys
305                 310                 315                 320

Asp Arg Phe Thr Ile Ser Arg Asp Asp Ser Lys Asn Thr Ala Tyr Leu
                325                 330                 335

Gln Met Asn Asn Leu Lys Thr Glu Asp Thr Ala Val Tyr Tyr Cys Val
            340                 345                 350

Arg His Ala Asn Phe Gly Asn Ser Tyr Ile Ser Tyr Trp Ala Tyr Trp
            355                 360                 365

Gly Gln Gly Thr Leu Val Thr Val Ser Ser Gly Gly Gly Gly Ser Gly
            370                 375                 380

Gly Gly Ser Gly Gly Gly Ser Gln Thr Val Val Thr Gln Glu
385                 390                 395                 400

Pro Ser Leu Thr Val Ser Pro Gly Gly Thr Val Thr Leu Thr Cys Ala
            405                 410                 415

Ser Ser Thr Gly Ala Val Thr Ser Gly Asn Tyr Pro Asn Trp Val Gln
            420                 425                 430

Gln Lys Pro Gly Gln Ala Pro Arg Gly Leu Ile Gly Gly Thr Lys Phe
            435                 440                 445

Leu Val Pro Gly Thr Pro Ala Arg Phe Ser Gly Ser Leu Leu Gly Gly
            450                 455                 460

Lys Ala Ala Leu Thr Leu Ser Gly Val Gln Pro Glu Asp Glu Ala Glu
465                 470                 475                 480

Tyr Tyr Cys Thr Leu Trp Tyr Ser Asn Arg Trp Val Phe Gly Gly Gly
                485                 490                 495

Thr Lys Leu Thr Val Leu His His His His His
            500                 505
```

<210> SEQ ID NO 152
<211> LENGTH: 499
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

```
Glu Val Gln Leu Val Glu Ser Gly Gly Gly Leu Val Gln Pro Gly Gly
1               5                   10                  15

Ser Leu Thr Leu Ser Cys Ala Ala Ser Arg Phe Met Ile Ser Glu Tyr
            20                  25                  30

His Met His Trp Val Arg Gln Ala Pro Gly Lys Gly Leu Glu Trp Val
        35                  40                  45

Ser Thr Ile Asn Pro Ala Gly Thr Thr Asp Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Asp
                85                  90                  95

Ser Tyr Gly Tyr Arg Gly Gln Gly Thr Leu Val Thr Val Ser Ser Gly
            100                 105                 110

Gly Gly Gly Ser Gly Gly Gly Ser Glu Val Gln Leu Val Glu Ser Gly
        115                 120                 125

Gly Gly Leu Val Gln Pro Gly Asn Ser Leu Arg Leu Ser Cys Ala Ala
    130                 135                 140

Ser Gly Phe Thr Phe Ser Lys Phe Gly Met Ser Trp Val Arg Gln Ala
145                 150                 155                 160

Pro Gly Lys Gly Leu Glu Trp Val Ser Ser Ile Ser Gly Ser Gly Arg
                165                 170                 175

Asp Thr Leu Tyr Ala Asp Ser Val Lys Gly Arg Phe Thr Ile Ser Arg
            180                 185                 190

Asp Asn Ala Lys Thr Thr Leu Tyr Leu Gln Met Asn Ser Leu Arg Pro
        195                 200                 205

Glu Asp Thr Ala Val Tyr Tyr Cys Thr Ile Gly Gly Ser Leu Ser Val
    210                 215                 220

Ser Ser Gln Gly Thr Leu Val Thr Val Ser Ser Gly Gly Gly Gly Ser
225                 230                 235                 240

Gly Gly Gly Ser Glu Val Gln Leu Val Glu Ser Gly Gly Gly Leu Val
                245                 250                 255

Gln Pro Gly Gly Ser Leu Lys Leu Ser Cys Ala Ala Ser Gly Phe Thr
            260                 265                 270

Phe Asn Lys Tyr Ala Ile Asn Trp Val Arg Gln Ala Pro Gly Lys Gly
        275                 280                 285

Leu Glu Trp Val Ala Arg Ile Arg Ser Lys Tyr Asn Asn Tyr Ala Thr
    290                 295                 300

Tyr Tyr Ala Asp Gln Val Lys Asp Arg Phe Thr Ile Ser Arg Asp Asp
305                 310                 315                 320

Ser Lys Asn Thr Ala Tyr Leu Gln Met Asn Asn Leu Lys Thr Glu Asp
                325                 330                 335

Thr Ala Val Tyr Tyr Cys Val Arg His Ala Asn Phe Gly Asn Ser Tyr
            340                 345                 350

Ile Ser Tyr Trp Ala Tyr Trp Gly Gln Gly Thr Leu Val Thr Val Ser
```

```
                355                 360                 365
Ser Gly Gly Gly Ser Gly Gly Gly Ser Gly Gly Gly Ser
        370                 375                 380

Gln Thr Val Val Thr Gln Glu Pro Ser Leu Thr Val Ser Pro Gly Gly
385                 390                 395                 400

Thr Val Thr Leu Thr Cys Ala Ser Ser Thr Gly Ala Val Thr Ser Gly
                405                 410                 415

Asn Tyr Pro Asn Trp Val Gln Gln Lys Pro Gly Gln Ala Pro Arg Gly
            420                 425                 430

Leu Ile Gly Gly Thr Lys Phe Leu Val Pro Gly Thr Pro Ala Arg Phe
        435                 440                 445

Ser Gly Ser Leu Leu Gly Gly Lys Ala Ala Leu Thr Leu Ser Gly Val
    450                 455                 460

Gln Pro Glu Asp Glu Ala Glu Tyr Tyr Cys Thr Leu Trp Tyr Ser Asn
465                 470                 475                 480

Arg Trp Val Phe Gly Gly Gly Thr Lys Leu Thr Val Leu His His His
                485                 490                 495

His His His

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 "Gly Ser"
      repeating units

<400> SEQUENCE: 153

Gly Ser Gly Ser Gly Ser Gly Ser Gly Ser Gly Ser Gly Ser Gly Ser
1               5                   10                  15

Gly Ser Gly Ser
            20

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser"
      repeating units

<400> SEQUENCE: 154

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 155
<211> LENGTH: 40
<212> TYPE: PRT
<213> ORGANISM: Artificial Sequence
<220> FEATURE:
<223> OTHER INFORMATION: Description of Artificial Sequence: Synthetic
```

```
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 155

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 156
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units

<400> SEQUENCE: 156

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 157
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units

<400> SEQUENCE: 157

Gly Gly Ser Gly Gly Gly Gly Ser Gly Gly Gly Ser Gly Gly Gly
1               5                   10                  15

Gly Ser Gly Gly Gly Ser Gly Gly Gly Ser Gly Gly Gly Gly
            20                  25                  30

Ser Gly Gly Gly Gly Ser Gly Gly Gly Gly Ser Gly Gly Gly Ser
        35                  40                  45

Gly Gly
    50

<210> SEQ ID NO 158
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 158

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 159
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Gly Gly Gly Ser Gly Gly Gly Gly Ser Gly Gly Gly Gly Ser Gly
1               5                   10                  15

Gly Gly Gly Ser
            20

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gly Gly Gly Ser Gly Gly Gly Gly Ser Gly Gly Gly Gly Ser
1               5                   10                  15

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 161

His His His His His His
1               5

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Glu, Pro, Ser, His, Thr, Asp, Gly, Lys, Gln or
      Tyr
<220> FEATURE:
```

```
<221> NAME/KEY: MOD_RES
<222> LOCATION: (8)..(8)
<223> OTHER INFORMATION: Glu, Pro, Ser, His, Thr, Asp, Gly, Lys, Gln or
      Tyr

<400> SEQUENCE: 162

Arg Phe Met Ile Ser Xaa Tyr Xaa Met His
1               5                   10

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Pro, Ser, His, Thr, Asp, Gly, Lys, Gln or
      Tyr
<220> FEATURE:
<221> NAME/KEY: MOD_RES
<222> LOCATION: (6)..(7)
<223> OTHER INFORMATION: Glu, Pro, Ser, His, Thr, Asp, Gly, Lys, Gln or
      Tyr
<220> FEATURE:
<221> NAME/KEY: MOD_RES
<222> LOCATION: (13)..(13)
<223> OTHER INFORMATION: Glu, Pro, Ser, His, Thr, Asp, Gly, Lys, Gln or
      Tyr

<400> SEQUENCE: 163

Xaa Ile Asn Pro Ala Xaa Xaa Thr Asp Tyr Ala Glu Xaa Val Lys Gly
1               5                   10                  15

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu, Pro, Ser, His, Thr, Asp, Gly, Lys, Gln or
      Tyr

<400> SEQUENCE: 164

Asp Xaa Tyr Gly Tyr
1               5

<210> SEQ ID NO 165
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Val Gln Leu Val Glu Ser Gly Gly Gly Leu Val Gln Pro Gly Gly
1               5                   10                  15

Ser Leu Thr Leu Ser Cys Ala Ala Ser
            20                  25

<210> SEQ ID NO 166
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 166

Trp Val Arg Gln Ala Pro Gly Lys Gly Leu Glu Trp Val Ser
1               5                   10

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Asp Gly Tyr Gly Tyr Arg Gly Gln Gly Thr Leu Val Thr Val Ser Ser
1               5                   10                  15
```

PSMA TARGETING TRISPECIFIC PROTEINS AND METHODS OF USE

CROSS-REFERENCE

This application claims the benefit of U.S. Provisional Application Nos. 62/426,069 filed Nov. 23, 2016, and 62/426,077 filed Nov. 23, 2016, which are incorporated by reference herein in their entirety.

SEQUENCE LISTING

The instant application contains a Sequence Listing which has been submitted electronically in ASCII format and is hereby incorporated by reference in its entirety. Said ASCII copy, created on Nov. 22, 2017, is named 47517-708_201_SL.txt and is 150,911 bytes in size.

BACKGROUND OF THE INVENTION

The selective destruction of an individual cell or a specific cell type is often desirable in a variety of clinical settings. For example, it is a primary goal of cancer therapy to specifically destroy tumor cells, while leaving healthy cells and tissues intact and undamaged. One such method is by inducing an immune response against the tumor, to make immune effector cells such as natural killer (NK) cells or cytotoxic T lymphocytes (CTLs) attack and destroy tumor cells.

SUMMARY OF THE INVENTION

Provided herein are trispecific antigen-binding protein, pharmaceutical compositions thereof, as nucleic acids, recombinant expression vectors and host cells for making such trispecific antigen-binding proteins, and methods of use for the treatment of diseases, disorders, or conditions. In one aspect, described herein are prostate specific membrane antigen (PSMA) targeting trispecific proteins, wherein said proteins comprise (a) a first domain (A) which specifically binds to human CD3; (b) a second domain (B) which is a half-life extension domain; and (c) a third domain (C) which specifically binds to PSMA, wherein the domains are linked in the order H2N-(A)-(C)-(B)-COOH, H2N-(B)-(A)-(C)-COOH, H2N-(C)-(B)-(A)-COOH, or by linkers L1 and L2. In some embodiments, the first domain comprises a variable light chain and variable heavy chain each of which is capable of specifically binding to human CD3. In some embodiments, the first domain comprises one or more sequences selected from the group consisting of SEQ ID NO: 1-88. In some embodiments, the first domain is humanized or human. In some embodiments, the first domain has a KD binding of 150 nM or less to CD3 on CD3 expressing cells. In some embodiments, the second domain binds human serum albumin. In some embodiments, the second domain comprises a scFv, a variable heavy domain (VH), a variable light domain (VL), a peptide, a ligand, or a small molecule. In some embodiments, the second domain comprises one or more sequences selected from the group consisting of SEQ ID NOs: 89-112. In some embodiments, the third domain comprises a scFv, a VH domain, a VL domain, a non-Ig domain, a ligand, a knottin, or a small molecule entity that specifically binds to PSMA. In some embodiments, the third domain comprises one or more sequences selected from the group consisting of SEQ ID NOs: 113-140.

In some embodiments, linkers L1 and L2 are each independently selected from (GS)n (SEQ ID NO: 153), (GGS)n (SEQ ID NO: 154), (GGGS)n (SEQ ID NO: 155), (GGSG)n (SEQ ID NO: 156), (GGSGG)n (SEQ ID NO: 157), or (GGGGS)n (SEQ ID NO: 158), wherein n is 1, 2, 3, 4, 5, 6, 7, 8, 9, or 10. In some embodiments, linkers L1 and L2 are each independently (GGGGS)4 (SEQ ID NO: 159) or (GGGGS)3 (SEQ ID NO: 160). In some embodiments, the domains are linked in the order H2N-(A)-(C)-(B)-COOH. In some embodiments, the domains are linked in the order H2N-(B)-(C)-(A)-COOH.

In some embodiments, the protein is less than about 80 kDa. In some embodiments, the protein is about 50 to about 75 kDa. In some embodiments, the protein is less than about 60 kDa. In some embodiments, the protein has an elimination half-time of at least about 50 hours. In some embodiments, the protein has an elimination half-time of at least about 100 hours. In some embodiments, the protein has increased tissue penetration as compared to an IgG to the same PSMA.

In some embodiments, the protein comprises a sequence selected from the group consisting of SEQ ID NO: 140-152.

In another aspect, provided herein are pharmaceutical composition comprising (i) the PSMA targeting trispecific protein according to any one of the above embodiments and (ii) a pharmaceutically acceptable carrier.

Also provided herein are methods of treating an individual in need of treatment of cancer, the method comprising administration of an effective amount of the pharmaceutical composition or PSMA targeting trispecific proteins according to any of the above embodiments. In some embodiments, the cancer is prostate cancer or renal cancer.

One embodiment provides a PSMA targeting trispecific protein, wherein said protein comprises (a) a first domain (A) which specifically binds to human CD3; (b) a second domain (B) which is a half-life extension domain; and (c) a third domain (C) which specifically binds to PSMA, wherein the second domain comprises one or more sequences selected from the group consisting of SEQ ID NOs: 113-140. In some embodiments, domains are linked in the order H2N-(A)-(C)-(B)-COOH, H2N-(B)-(A)-(C)-COOH, H2N-(C)-(B)-(A)-COOH, or by linkers L1 and L2. In some embodiments, the first domain comprises one or more sequences selected from the group consisting of SEQ ID NO: 1-88. In some embodiments, the second domain comprises one or more sequences selected from the group consisting of SEQ ID NO: 89-112.

One embodiment provides a PSMA targeting trispecific protein, wherein said protein comprises a sequence selected from the group consisting of SEQ ID NO: 140-152. In some embodiments, said protein comprises a sequence selected from the group consisting of SEQ ID NO: 150-152.

One embodiment provides a prostate specific membrane antigen (PSMA) targeting trispecific protein, wherein said protein comprises (a) a first domain (A) which specifically binds to human CD3; (b) a second domain (B) which is a half-life extension domain; and (c) a third domain (C) which specifically binds to PSMA, wherein the domains are linked in the order $H_2N$-(C)-(B)-(A)-COOH, or by linkers L1 and L2, and wherein the third domain comprises one or more sequences selected from the group consisting of SEQ ID NO: 113-140.

One embodiment provides a PSMA targeting trispecific protein, wherein said protein comprises (a) a first domain (A) which specifically binds to human CD3; (b) a second domain (B) which is a half-life extension domain; and (c) a third domain (C) which specifically binds to PSMA, wherein the domains are linked in the order H₂N-(C)-(B)-(A)-COOH, or by linkers L1 and L2, and wherein the first domain comprises one or more sequences selected from the group consisting of SEQ ID NO: 1-88.

One embodiment provides a method of treating prostate cancer, the method comprising administration of an effective amount of a PSMA targeting trispecific protein, wherein said protein comprises (a) a first domain (A) which specifically binds to human CD3; (b) a second domain (B) which is a half-life extension domain; and (c) a third domain (C) which specifically binds to PSMA, wherein the domains are linked in the order H₂N-(C)-(B)-(A)-COOH, or by linkers L1 and L2, and wherein the third domain comprises one or more sequences selected from the group consisting of SEQ ID NO: 113-140.

One embodiment provides a method of treating prostate cancer, the method comprising administration of an effective amount of a PSMA targeting trispecific protein, wherein said protein comprises (a) a first domain (A) which specifically binds to human CD3; (b) a second domain (B) which is a half-life extension domain; and (c) a third domain (C) which specifically binds to PSMA, wherein the domains are linked in the order H₂N-(C)-(B)-(A)-COOH, or by linkers L1 and L2, and wherein the first domain comprises one or more sequences selected from the group consisting of SEQ ID NO: 1-88.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows killing by different PSMA targeting TRITAC™ molecules in prostate cancer model LNCaP. FIG. 2B shows killing by different PSMA targeting TRITAC™ molecules in prostate cancer model 22Rv1.

FIG. 5A shows the experiment performed in the absence of human serum albumin with a PSMA targeting BiTE as positive control. FIG. 5B shows the experiment performed in the presence of human serum albumin with a PSMA targeting BiTE as positive control. FIG. 5C shows EC50 values for PSMA targeting TRITAC™ in the presence or absence of HSA with a PSMA targeting BiTE as a positive control in LNCaP prostate cancer models.

FIG. 7A shows EGFR and PSMA expression in LNCaP, KMS12BM, and OVCAR8 cell lines. FIG. 7B shows killing of LNCaP tumor cells by PSMA, EGFR, and negative control TRITAC™ molecules. FIG. 7C shows killing of KMS12BM tumor cells by PSMA, EGFR, and negative control TRITAC™ molecules. FIG. 7D shows killing of OVCAR8 cells by PSMA, EGFR, and negative control TRITAC™ molecules.

FIG. 8A shows PSMA TRITAC™ C235 activity after pre-incubation at 37° C. or freeze/thaw cycles. FIG. 8B shows PSMA TRITAC™ C359 activity after pre-incubation at 37° C. or freeze/thaw cycles. FIG. 8C shows PSMA TRITAC™ C360 activity after pre-incubation at 37° C. or freeze/thaw cycles. FIG. 8D shows PSMA TRITAC™ C361 activity after pre-incubation at 37° C. or freeze/thaw cycles.

FIG. 9A shows the impact of the PSMA targeting TRITAC™ molecule in redirecting cynomolgus peripheral blood mononuclear cells (PBMCs), from cynomolgus monkey donor G322, in killing LNCaP cells. FIG. 9B shows the impact of the PSMA targeting TRITAC™ molecule in redirecting cynomolgus PBMCs, from cynomolgus monkey donor D173, to kill MDAPCa2b cells.

FIG. 12A shows redirected T cell killing of LnCaP cells by PSMA PH1T TRITAC™ (SEQ ID No: 150) and PSMA PH1 TRITAC™ (SEQ ID NO: 151) molecules. FIG. 12B shows redirected T cell killing of LnCaP cells by PSMA Z2 TRITAC™ (SEQ ID NO: 152).

DETAILED DESCRIPTION OF THE INVENTION

Figure 1:
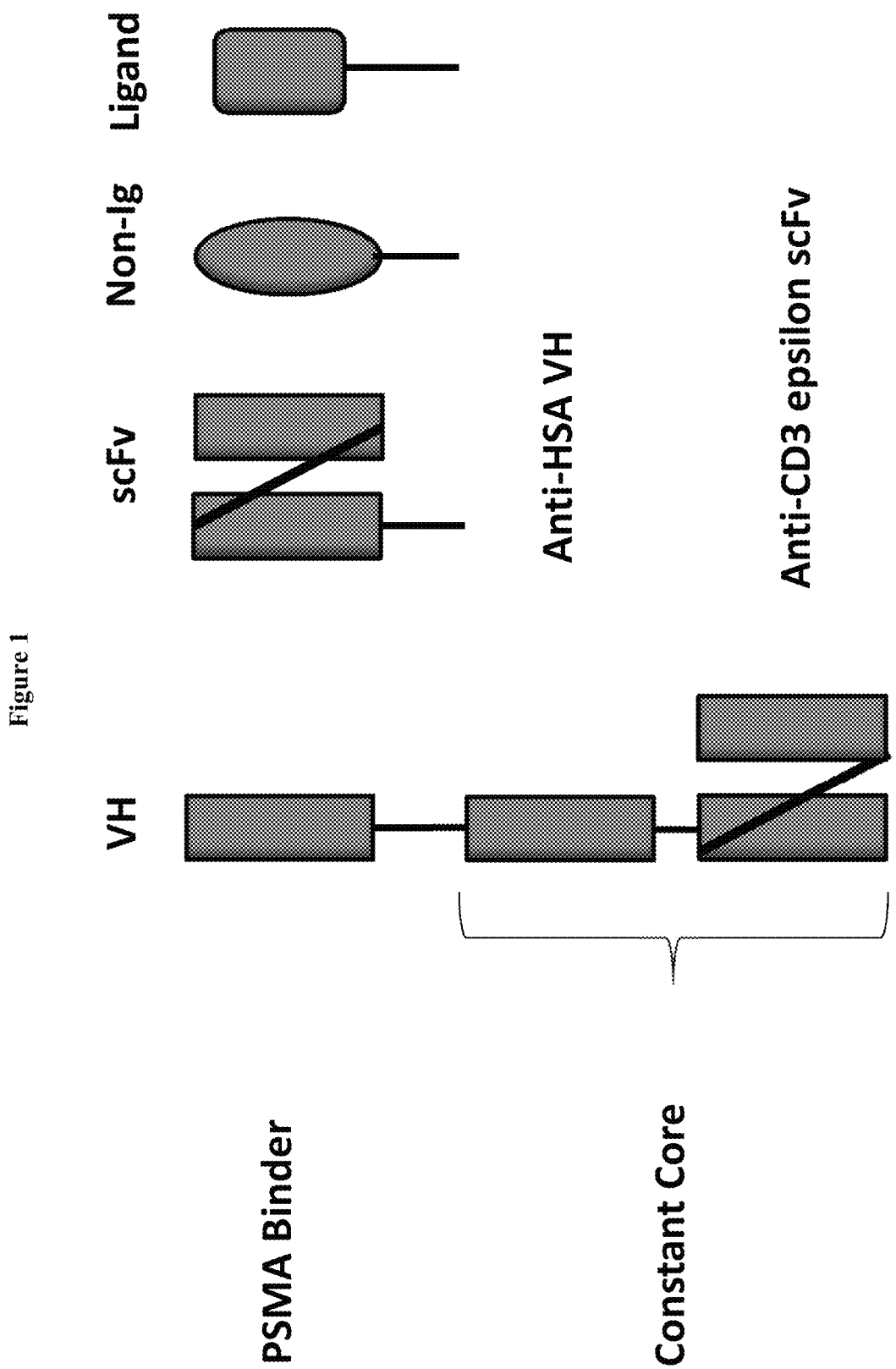
FIG. 1 is schematic representation of an exemplary PSMA targeting trispecific antigen-binding protein where the protein has an constant core element comprising an anti-CDR single chain variable fragment (scFv) and an anti-HSA variable heavy chain region; and a PSMA binding domain that can be a VH, scFv, a non-Ig binder, or ligand.

Described herein are trispecific proteins that target prostate specific membrane antigen (PSMA), pharmaceutical compositions thereof, as well as nucleic acids, recombinant expression vectors and host cells for making such proteins thereof. Also provided are methods of using the disclosed PSMA targeting trispecific proteins in the prevention, and/or treatment of diseases, conditions and disorders. The PSMA targeting trispecific proteins are capable of specifically binding to PSMA as well as CD3 and have a half-life extension domain, such as a domain binding to human serum albumin (HSA). FIG. 1 depicts one non-limiting example of a trispecific antigen-binding protein.

In one aspect, the PSMA targeting trispecific proteins comprise a domain (A) which specifically binds to CD3, a domain (B) which specifically binds to human serum albumin (HSA), and a domain (C) which specifically binds to PSMA. The three domains in PSMA targeting trispecific proteins are arranged in any order. Thus, it is contemplated that the domain order of the PSMA targeting trispecific proteins are:

$H_2N$-(A)-(B)-(C)-COOH, $H_2N$-(A)-(C)-(B)-COOH, $H_2N$-(B)-(A)-(C)-COOH, $H_2N$-(B)-(C)-(A)-COOH, $H_2N$-(C)-(B)-(A)-COOH, or $H_2N$-(C)-(A)-(B)-COOH.

In some embodiments, the PSMA targeting trispecific proteins have a domain order of $H_2N$-(A)-(B)-(C)-COOH. In some embodiments, the PSMA targeting trispecific proteins have a domain order of $H_2N$-(A)-(C)-(B)-COOH. In some embodiments, the PSMA targeting trispecific proteins have a domain order of $H_2N$-(B)-(A)-(C)-COOH. In some embodiments, the PSMA targeting trispecific proteins have a domain order of $H_2N$-(B)-(C)-(A)-COOH. In some embodiments, the PSMA targeting trispecific proteins have a domain order of $H_2N$-(C)-(B)-(A)-COOH. In some embodiments, the PSMA targeting trispecific proteins have a domain order of $H_2N$-(C)-(A)-(B)-COOH.

In some embodiments, the PSMA targeting trispecific proteins have the HSA binding domain as the middle domain, such that the domain order is $H_2N$-(A)-(B)-(C)-COOH or $H_2N$-(C)-(B)-(A)-COOH. It is contemplated that in such embodiments where the HSA binding domain as the middle domain, the CD3 and PSMA binding domains are afforded additional flexibility to bind to their respective targets.

In some embodiments, the PSMA targeting trispecific proteins described herein comprise a polypeptide having a sequence described in Table 10 (SEQ ID NO: 140-152) and subsequences thereof. In some embodiments, the trispecific antigen binding protein comprises a polypeptide having at least 70%-95% or more homology to a sequence described in Table 10 (SEQ ID NO: 140-152). In some embodiments, the trispecific antigen binding protein comprises a polypeptide having at least 70%, 75%, 80%, 85%, 90%, 95%, or more homology to a sequence described in Table 10 (SEQ ID NO: 140-152). In some embodiments, the trispecific antigen binding protein has a sequence comprising at least a portion of a sequence described in Table 10 (SEQ ID NO: 140-152). In some embodiments, the PSMA trispecific antigen-binding protein comprises a polypeptide comprising one or more of the sequences described in Table 10 (SEQ ID NO: 140-152). In further embodiments, the PSMA trispecific antigen-binding protein comprises one or more CDRs as described in the sequences in Table 10 (SEQ ID NO: 140-152).

The PSMA targeting trispecific proteins described herein are designed to allow specific targeting of cells expressing PSMA by recruiting cytotoxic T cells. This improves efficacy compared to ADCC (antibody dependent cell-mediated cytotoxicity), which is using full length antibodies directed to a sole antigen and is not capable of directly recruiting cytotoxic T cells. In contrast, by engaging CD3 molecules expressed specifically on these cells, the PSMA targeting trispecific proteins can crosslink cytotoxic T cells with cells expressing PSMA in a highly specific fashion, thereby directing the cytotoxic potential of the T cell towards the target cell. The PSMA targeting trispecific proteins described herein engage cytotoxic T cells via binding to the surface-expressed CD3 proteins, which form part of the TCR. Simultaneous binding of several PSMA trispecific antigen-binding protein to CD3 and to PSMA expressed on the surface of particular cells causes T cell activation and mediates the subsequent lysis of the particular PSMA expressing cell. Thus, PSMA targeting trispecific proteins are contemplated to display strong, specific and efficient target cell killing. In some embodiments, the PSMA targeting trispecific proteins described herein stimulate target cell killing by cytotoxic T cells to eliminate pathogenic cells (e.g., tumor cells expressing PSMA). In some of such embodiments, cells are eliminated selectively, thereby reducing the potential for toxic side effects.

The PSMA targeting trispecific proteins described herein confer further therapeutic advantages over traditional monoclonal antibodies and other smaller bispecific molecules. Generally, the effectiveness of recombinant protein pharmaceuticals depends heavily on the intrinsic pharmacokinetics of the protein itself. One such benefit here is that the PSMA targeting trispecific proteins described herein have extended pharmacokinetic elimination half-time due to having a half-life extension domain such as a domain specific to HSA. In this respect, the PSMA targeting trispecific proteins described herein have an extended serum elimination half-time of about two, three, about five, about seven, about 10, about 12, or about 14 days in some embodiments. This contrasts to other binding proteins such as BiTE or DART molecules which have relatively much shorter elimination half-times. For example, the BiTE CD19×CD3 bispecific scFv-scFv fusion molecule requires continuous intravenous infusion (i.v.) drug delivery due to its short elimination half-time. The longer intrinsic half-times of the PSMA targeting trispecific proteins solve this issue thereby allowing for increased therapeutic potential such as low-dose pharmaceutical formulations, decreased periodic administration and/or novel pharmaceutical compositions.

The PSMA targeting trispecific proteins described herein also have an optimal size for enhanced tissue penetration and tissue distribution. Larger sizes limit or prevent penetration or distribution of the protein in the target tissues. The PSMA targeting trispecific proteins described herein avoid this by having a small size that allows enhanced tissue penetration and distribution. Accordingly, the PSMA targeting trispecific proteins described herein, in some embodiments have a size of about 50 kD to about 80 kD, about 50 kD to about 75 kD, about 50 kD to about 70 kD, or about 50 kD to about 65 kD. Thus, the size of the PSMA targeting trispecific proteins is advantageous over IgG antibodies which are about 150 kD and the BiTE and DART diabody molecules which are about 55 kD but are not half-life extended and therefore cleared quickly through the kidney.

In further embodiments, the PSMA targeting trispecific proteins described herein have an optimal size for enhanced tissue penetration and distribution. In these embodiments, the PSMA targeting trispecific proteins are constructed to be as small as possible, while retaining specificity toward its targets. Accordingly, in these embodiments, the PSMA targeting trispecific proteins described herein have a size of about 20 kD to about 40 kD or about 25 kD to about 35 kD to about 40 kD, to about 45 kD, to about 50 kD, to about 55 kD, to about 60 kD, to about 65 kD. In some embodiments, the PSMA targeting trispecific proteins described herein have a size of about 50 kD, 49, kD, 48 kD, 47 kD, 46 kD, 45 kD, 44 kD, 43 kD, 42 kD, 41 kD, 40 kD, about 39 kD, about 38 kD, about 37 kD, about 36 kD, about 35 kD, about 34 kD, about 33 kD, about 32 kD, about 31 kD, about 30 kD, about 29 kD, about 28 kD, about 27 kD, about 26 kD, about 25 kD, about 24 kD, about 23 kD, about 22 kD, about 21 kD, or about 20 kD. An exemplary approach to the small size is through the use of single domain antibody (sdAb) fragments for each of the domains. For example, a particular PSMA trispecific antigen-binding protein has an anti-CD3 sdAb, anti-HSA sdAb and an sdAb for PSMA. This reduces the size of the exemplary PSMA trispecific antigen-binding protein to under 40 kD. Thus in some embodiments, the domains of the PSMA targeting trispecific proteins are all single domain antibody (sdAb) fragments. In other embodiments, the PSMA targeting trispecific proteins described herein comprise small molecule entity (SME) binders for HSA and/or the PSMA. SME binders are small molecules averaging about 500 to 2000 Da in size and are attached to the PSMA targeting trispecific proteins by known methods, such as sortase ligation or conjugation. In these instances, one of the domains of PSMA trispecific antigen-binding protein is a sortase recognition sequence, e.g., LPETG (SEQ ID NO: 57). To attach a SME binder to PSMA trispecific antigen-binding protein with a sortase recognition sequence, the protein is incubated with a sortase and a SME binder whereby the sortase attaches the SME binder to the recognition sequence. Known SME binders include MIP-1072 and MIP-1095 which bind to prostate-specific membrane antigen (PSMA). In yet other embodiments, the domain which binds to PSMA of PSMA targeting trispecific proteins described herein comprise a knottin peptide for binding PSMA. Knottins are disulfide-stabilized peptides with a cysteine knot scaffold and have average sizes about 3.5 kD. Knottins have been contemplated for binding to certain tumor molecules such as PSMA. In further embodiments, domain which binds to PSMA of PSMA targeting trispecific proteins described herein comprise a natural PSMA ligand.

Another feature of the PSMA targeting trispecific proteins described herein is that they are of a single-polypeptide design with flexible linkage of their domains. This allows for facile production and manufacturing of the PSMA targeting trispecific proteins as they can be encoded by single cDNA molecule to be easily incorporated into a vector. Further, because the PSMA targeting trispecific proteins described herein are a monomeric single polypeptide chain, there are no chain pairing issues or a requirement for dimerization. It is contemplated that the PSMA targeting trispecific proteins described herein have a reduced tendency to aggregate unlike other reported molecules such as bispecific proteins with Fc-gamma immunoglobulin domains.

In the PSMA targeting trispecific proteins described herein, the domains are linked by internal linkers L1 and L2, where L1 links the first and second domain of the PSMA targeting trispecific proteins and L2 links the second and third domains of the PSMA targeting trispecific proteins. Linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 are "short", i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 are "long", i.e., consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the PSMA targeting trispecific proteins, do not interfere with the binding domains as well as resist cleavage from proteases. For example, glycine and serine residues generally provide protease resistance. Examples of internal linkers suitable for linking the domains in the PSMA targeting trispecific proteins include but are not limited to $(GS)_n$ (SEQ ID NO: 153), $(GGS)_n$ (SEQ ID NO: 154), $(GGGS)_n$ (SEQ ID NO: 155), $(GGSG)_n$ (SEQ ID NO: 156), $(GGSGG)_n$ (SEQ ID NO: 157), or $(GGGGS)_n$ (SEQ ID NO: 158), wherein n is 1, 2, 3, 4, 5, 6, 7, 8, 9, or 10. In one embodiment, internal linker L1 and/or L2 is $(GGGGS)_4$ (SEQ ID NO: 159) or $(GGGGS)_3$ (SEQ ID NO: 160).

CD3 Binding Domain

The specificity of the response of T cells is mediated by the recognition of antigen (displayed in context of a major histocompatibility complex, MEW) by the TCR. As part of the TCR, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the TCR as well as CD3ζ (zeta) altogether to comprise the complete TCR. Clustering of CD3 on T cells, such as by immobilized anti-CD3 antibodies leads to T cell activation similar to the engagement of the T cell receptor but independent of its clone-typical specificity.

In one aspect, the PSMA targeting trispecific proteins described herein comprise a domain which specifically binds to CD3. In one aspect, the PSMA targeting trispecific proteins described herein comprise a domain which specifically binds to human CD3. In some embodiments, the PSMA targeting trispecific proteins described herein comprise a domain which specifically binds to CD3γ. In some embodiments, the PSMA targeting trispecific proteins described herein comprise a domain which specifically binds to CD3δ. In some embodiments, the PSMA targeting trispecific proteins described herein comprise a domain which specifically binds to CD3ε.

In further embodiments, the PSMA targeting trispecific proteins described herein comprise a domain which specifically binds to the TCR. In certain instances, the PSMA targeting trispecific proteins described herein comprise a domain which specifically binds the α chain of the TCR. In certain instances, the PSMA targeting trispecific proteins described herein comprise a domain which specifically binds the β chain of the TCR.

In certain embodiments, the CD3 binding domain of the PSMA targeting trispecific proteins described herein exhibit not only potent CD3 binding affinities with human CD3, but show also excellent crossreactivity with the respective cynomolgus monkey CD3 proteins. In some instances, the CD3 binding domain of the PSMA targeting trispecific proteins are cross-reactive with CD3 from cynomolgus monkey. In certain instances, human:cynomolgous $K_D$ ratios for CD3 are between 5 and 0.2.

In some embodiments, the CD3 binding domain of the PSMA trispecific antigen-binding protein can be any domain that binds to CD3 including but not limited to domains from a monoclonal antibody, a polyclonal antibody, a recombinant antibody, a human antibody, a humanized antibody. In some instances, it is beneficial for the CD3 binding domain to be derived from the same species in which the PSMA trispecific antigen-binding protein will ultimately be used in. For example, for use in humans, it may be beneficial for the CD3 binding domain of the PSMA trispecific antigen-binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3 binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3 binding domain described herein, e.g., a humanized or human anti-CD3 binding domain comprising one or more, e.g., all three, LC CDRs and one or more, e.g., all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lamda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In one embodiment, the anti-CD3 binding domain is a single chain variable fragment (scFv) comprising a light chain and a heavy chain of an amino acid sequence provided herein. As used herein, "single chain variable fragment" or "scFv" refers to an antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In an embodiment, the anti-CD3 binding domain comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region.

In some instances, scFvs which bind to CD3 are prepared according to known methods. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the CD3 binding site. In certain embodiments, such scFv linkers are "short", i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 9 or 10 contiguous amino acid residues. Regarding the amino acid composition of the scFv linkers, peptides are selected that confer flexibility, do not interfere with the variable domains as well as allow interchain folding to bring the two variable domains together to form a functional CD3 binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the CD3 binding and production yield of the scFv. Examples of peptide scFv linkers suitable for linking a variable light chain domain and a variable heavy chain domain in a scFv include but are not limited to $(GS)_n$ (SEQ ID NO: 153), $(GGS)_n$ (SEQ ID NO: 154), $(GGGS)_n$ (SEQ ID NO: 155), $(GGSG)_n$ (SEQ ID NO: 156), $(GGSGG)_n$ (SEQ ID NO: 157), or $(GGGGS)_n$ (SEQ ID NO: 158), wherein n is 1, 2, 3, 4, 5, 6, 7, 8, 9, or 10. In one embodiment, the scFv linker can be $(GGGGS)_4$ (SEQ ID NO: 159) or $(GGGGS)_3$ (SEQ ID NO: 160). Variation in the linker length may retain or enhance activity, giving rise to superior efficacy in activity studies.

In some embodiments, CD3 binding domain of PSMA trispecific antigen-binding protein has an affinity to CD3 on CD3 expressing cells with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of PSMA trispecific antigen-binding protein has an affinity to CD3ε, γ, or δ with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of PSMA trispecific antigen-binding protein has low affinity to CD3, i.e., about 100 nM or greater.

The affinity to bind to CD3 can be determined, for example, by the ability of the PSMA trispecific antigen-binding protein itself or its CD3 binding domain to bind to CD3 coated on an assay plate; displayed on a microbial cell surface; in solution; etc. The binding activity of the PSMA trispecific antigen-binding protein itself or its CD3 binding domain of the present disclosure to CD3 can be assayed by immobilizing the ligand (e.g., CD3) or the PSMA trispecific antigen-binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

In some embodiments, CD3 binding domains described herein comprise a polypeptide having a sequence described in Table 7 (SEQ ID NO: 1-88) and subsequences thereof. In some embodiments, the CD3 binding domain comprises a polypeptide having at least 70%-95% or more homology to a sequence described in Table 7 (SEQ ID NO: 1-88). In some embodiments, the CD3 binding domain comprises a polypeptide having at least 70%, 75%, 80%, 85%, 90%, 95%, or more homology to a sequence described in Table 7 (SEQ ID NO: 1-88). In some embodiments, the CD3 binding domain has a sequence comprising at least a portion of a sequence described in Table 7 (SEQ ID NO: 1-88). In some embodiments, the CD3 binding domain comprises a polypeptide comprising one or more of the sequences described in Table 7 (SEQ ID NO: 1-88).

In certain embodiments, CD3 binding domain comprises an scFv with a heavy chain CDR1 comprising SEQ ID NO: 16, and 22-33. In certain embodiments, CD3 binding domain comprises an scFv with a heavy chain CDR2 comprising SEQ ID NO: 17, and 34-43. In certain embodiments, CD3 binding domain comprises an scFv with a heavy chain CDR3 comprising SEQ ID NO: 18, and 44-53. In certain embodiments, CD3 binding domain comprises an scFv with a light chain CDR1 comprising SEQ ID NO: 19, and 54-66. In certain embodiments, CD3 binding domain comprises an scFv with a light chain CDR2 comprising SEQ ID NO: 20, and 67-79. In certain embodiments, CD3 binding domain comprises an scFv with a light chain CDR3 comprising SEQ ID NO: 21, and 80-86.

Half-Life Extension Domain

Contemplated herein are domains which extend the half-life of an antigen-binding domain. Such domains are contemplated to include but are not limited to HSA binding domains, Fc domains, small molecules, and other half-life extension domains known in the art.

Human serum albumin (HSA) (molecular mass ~67 kDa) is the most abundant protein in plasma, present at about 50 mg/ml (600 µM), and has a half-life of around 20 days in humans. HSA serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins. For example, a recombinant fusion of an albumin binding domain to a Fab fragment resulted in an in vivo clearance of 25- and 58-fold and a half-life extension of 26- and 37-fold when administered intravenously to mice and rabbits respectively as compared to the administration of the Fab fragment alone. In another example, when insulin is acylated with fatty acids to promote association with albumin, a protracted effect was observed when injected subcutaneously in rabbits or pigs. Together, these studies demonstrate a linkage between albumin binding and prolonged action.

In one aspect, the PSMA targeting trispecific proteins described herein comprise a half-life extension domain, for example a domain which specifically binds to HSA. In some embodiments, the HSA binding domain of PSMA trispecific antigen-binding protein can be any domain that binds to HSA including but not limited to domains from a monoclonal antibody, a polyclonal antibody, a recombinant antibody, a human antibody, a humanized antibody. In some embodiments, the HSA binding domain is a single chain variable fragments (scFv), single-domain antibody such as a heavy chain variable domain (VH), a light chain variable domain (VL) and a variable domain (VHH) of camelid derived single domain antibody, peptide, ligand or small molecule entity specific for HSA. In certain embodiments, the HSA binding domain is a single-domain antibody. In other embodiments, the HSA binding domain is a peptide. In further embodiments, the HSA binding domain is a small molecule. It is contemplated that the HSA binding domain of PSMA trispecific antigen-binding protein is fairly small and no more than 25 kD, no more than 20 kD, no more than 15 kD, or no more than 10 kD in some embodiments. In certain instances, the HSA binding is 5 kD or less if it is a peptide or small molecule entity.

The half-life extension domain of PSMA trispecific antigen-binding protein provides for altered pharmacodynamics and pharmacokinetics of the PSMA trispecific antigen-binding protein itself. As above, the half-life extension domain extends the elimination half-time. The half-life extension domain also alters pharmacodynamic properties including alteration of tissue distribution, penetration, and diffusion of the trispecific antigen-binding protein. In some embodiments, the half-life extension domain provides for improved tissue (including tumor) targeting, tissue distribution, tissue penetration, diffusion within the tissue, and enhanced efficacy as compared with a protein without an half-life extension domain. In one embodiment, therapeutic methods effectively and efficiently utilize a reduced amount of the trispecific antigen-binding protein, resulting in reduced side effects, such as reduced non-tumor cell cytotoxicity.

Further, the binding affinity of the half-life extension domain can be selected so as to target a specific elimination half-time in a particular trispecific antigen-binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include $K_D$ concentrations at 10 nM or less (high), between 10 nM and 100 nM (medium), and greater than 100 nM (low). As above, binding affinities to HSA are determined by known methods such as Surface Plasmon Resonance (SPR).

In some embodiments, HSA binding domains described herein comprise a polypeptide having a sequence described in Table 8 (SEQ ID NO: 89-112) and subsequences thereof. In some embodiments, the HSA binding domain comprises a polypeptide having at least 70%-95% or more homology to a sequence described in Table 8 (SEQ ID NO: 89-112). In some embodiments, the HSA binding domain comprises a polypeptide having at least 70%, 75%, 80%, 85%, 90%, 95%, or more homology to a sequence described in Table 8 (SEQ ID NO: 89-112). In some embodiments, the HSA binding domain has a sequence comprising at least a portion of a sequence described in Table 8 (SEQ ID NO: 89-112). In some embodiments, the HSA binding domain comprises a polypeptide comprising one or more of the sequences described in Table 8 (SEQ ID NO: 89-112).

In some embodiments, HSA binding domains described herein comprise a single domain antibody with a CDR1 comprising SE ID NO: 96, and 99-101. In some embodiments, HSA binding domains described herein comprise a single domain antibody with a CDR1 comprising SE ID NO: 97, and 102-107. In some embodiments, HSA binding domains described herein comprise a single domain antibody with a CDR1 comprising SE ID NO: 98, 108 and 109.

Prostate Specific Membrane Antigen (PSMA) Binding Domain

Prostate specific membrane antigen (PSMA) is a 100 kD Type II membrane glycoprotein expressed in prostate tissues having sequence identity with the transferrin receptor with NAALADase activity. PSMA is expressed in increased amounts in prostate cancer, and elevated levels of PSMA are also detectable in the sera of these patients. PSMA expression increases with disease progression, becoming highest in metastatic, hormone-refractory disease for which there is no present therapy.

In addition to the described CD3 and half-life extension domains, the PSMA targeting trispecific proteins described herein also comprise a domain that binds to PSMA. The design of the PSMA targeting trispecific proteins described herein allows the binding domain to PSMA to be flexible in that the binding domain to PSMA can be any type of binding domain, including but not limited to, domains from a monoclonal antibody, a polyclonal antibody, a recombinant antibody, a human antibody, a humanized antibody. In some embodiments, the binding domain to PSMA is a single chain variable fragments (scFv), single-domain antibody such as a heavy chain variable domain (VH), a light chain variable domain (VL) and a variable domain (VHH) of camelid derived single domain antibody. In other embodiments, the binding domain to PSMA is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to PSMA is a ligand or peptide that binds to or associates with PSMA. In yet further embodiments, the binding domain to PSMA is a knottin. In yet further embodiments, the binding domain to PSMA is a small molecular entity.

In some embodiments, the PSMA binding domain comprises the following formula: f1-r1-f2-r2-f3-r3-f4, wherein r1, r2, and r3 are complementarity determining regions CDR1, CDR2, and CDR3, respectively, and f1, f2, f3, and f4 are framework residues, and wherein r1 comprises SEQ ID No. 114, SEQ ID No. 115, SEQ ID No. 116, or SEQ ID NOL 125, r2 comprises SEQ ID No. 117, SEQ ID NO. 118, SEQ ID No. 119, SEQ ID No. 120, SEQ ID No. 121, SEQ ID No. 122, SEQ ID No. 123, or SEQ ID NO: 126, and r3 comprises SEQ ID No. 124, or SEQ ID NO: 127.

In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX4X$_5$TDYAEX6VKG), and (c) the amino acid sequence of CDR3 is as set forth in SEQ ID No. 164 (DX$_7$YGY). In some embodiments, the amino acid residues X$_1$, X$_2$, X$_3$, X$_4$, X$_5$, X$_6$, and X$_7$ are independently selected from glutamic acid, proline, serine, histidine, threonine, aspartic acid, glycine, lysine, threonine, glutamine, and tyrosine. In some embodiments, X$_1$ is proline. In some embodiments, X$_2$ is histidine. In some embodiments, X$_3$ is aspartic acid. In some embodiments, X$_4$ is lysine. In some embodiments, X$_5$ is glutamine. In some embodiments, X$_6$ is tyrosine. In some embodiments, X$_7$ is serine. The PSMA binding protein of the present disclosure may in some embodiments comprise CDR1, CDR2, and CDR3 sequences wherein X$_1$ is glutamic acid, X$_2$ is histidine, X$_3$ is aspartic acid, X$_4$ is glycine, X$_5$ is threonine, X$_6$ is serine, and X$_7$ is serine.

In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X1 is proline. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X5 is glutamine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_6$ is tyrosine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_4$ is lysine, and X$_7$ is serine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_2$ is histidine, X$_3$ is aspartic acid, X$_4$ is lysine, and X$_7$ is serine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_1$ is proline, X$_2$ is histidine, X$_3$ is aspartic acid, and X$_7$ is serine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_2$ is histidine, X$_3$ is aspartic acid, X$_5$ is glutamine, and X$_7$ is serine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_2$ is histidine, X$_3$ is aspartic acid, X$_6$ is tyrosine, and X$_7$ is serine. In some embodiments, the PSMA binding domain comprises a CDR1, CDR2, and CDR3, wherein (a) the amino acid sequence of CDR1 is as set forth in SEQ ID No. 162 (RFMISX$_1$YX$_2$MH), (b) the amino acid sequence of CDR2 is as set forth in SEQ ID No. 163 (X$_3$INPAX$_4$X$_5$TDYAEX$_6$VKG), and (c) the amino acid sequence of CDR3 is as set forth in SEQ ID No. 164 (DX$_7$YGY), wherein X$_2$ is histidine, X$_3$ is aspartic acid, and X$_7$ is serine.

The PSMA binding domain of the present disclosure may in some embodiments comprise CDR1, CDR2, and CDR3 sequences wherein X$_1$ is glutamic acid, X$_2$ is histidine, X$_3$ is threonine, X$_4$ is glycine, X$_5$ is threonine, X$_6$ is serine, and X$_7$ is serine. The PSMA binding domain of the present disclosure may in some embodiments comprise CDR1, CDR2, and CDR3 sequences wherein X$_1$ is glutamic acid, X$_2$ is histidine, X$_3$ is threonine, X$_4$ is glycine, X$_5$ is threonine, X$_6$ is serine, and X$_7$ is serine. The PSMA binding domain of the present disclosure may in some embodiments comprise CDR1, CDR2, and CDR3 sequences wherein X$_1$ is glutamic acid, X$_2$ is serine, X$_3$ is threonine, X$_4$ is lysine, X$_5$ is threonine, X$_6$ is serine, and X$_7$ is serine. The PSMA binding domain of the present disclosure may in some embodiments comprise CDR1, CDR2, and CDR3 sequences wherein X$_1$ is proline, X$_2$ is serine, X$_3$ is threonine, X$_4$ is glycine, X$_5$ is threonine, X$_6$ is serine, and X$_7$ is glycine. The PSMA binding domain of the present disclosure may in some embodiments comprise CDR1, CDR2, and CDR3 sequences wherein X$_1$ is glutamic acid, X$_2$ is serine, X$_3$ is threonine, X$_4$ is glycine, X$_5$ is glutamine, X$_6$ is serine, and X$_7$ is glycine. The PSMA binding domain of the present disclosure may in some embodiments comprise CDR1, CDR2, and CDR3 sequences wherein X$_1$ is glutamic acid, X$_2$ is serine, X$_3$ is threonine, X$_4$ is glycine, X$_5$ is threonine, X$_6$ is tyrosine, and X$_7$ is glycine. The PSMA binding domain of the present disclosure may in some embodiments comprise CDR1, CDR2, and CDR3 sequences wherein X$_1$ is glutamic acid, X$_2$ is histidine, X$_3$ is aspartic acid, X$_4$ is lysine, X$_5$ is threonine, X$_6$ is serine, and X$_7$ is serine. The PSMA binding domain of the present disclosure may in some embodiments comprise CDR1, CDR2, and CDR3 sequences wherein X$_1$ is proline, X$_2$ is histidine, X$_3$ is aspartic acid, X$_4$ is glycine, X$_5$ is threonine, X$_6$ is serine, and X$_7$ is serine. The PSMA binding domain of the present disclosure may in some embodiments comprise CDR1, CDR2, and CDR3 sequences wherein X$_1$ is glutamic acid, X$_2$ is histidine, X$_3$ is aspartic acid, X$_4$ is glutamine, X$_5$ is threonine, X$_6$ is serine, and X$_7$ is serine. The PSMA binding domain of the present disclosure may in some embodiments comprise CDR1, CDR2, and CDR3 sequences wherein X$_1$ is glutamic acid, X$_2$ is histidine, X$_3$ is aspartic acid, X$_4$ is glycine, X$_5$ is threonine, X$_6$ is tyrosine, and X$_7$ is serine. The PSMA binding domain of the present disclosure may in some embodiments comprise CDR1, CDR2, and CDR3 sequences wherein X$_2$ is histidine, and X$_7$ is serine. Exemplary framework sequences are disclosed as SEQ ID NO: 165-168.

In some embodiments, PSMA binding domains described herein comprise a polypeptide having a sequence described in Table 9 (SEQ ID NO: 113-140) and subsequences thereof. In some embodiments, the HSA binding domain comprises a polypeptide having at least 70%-95% or more homology to a sequence described in Table 9 (SEQ ID NO: 113-140). In some embodiments, the HSA binding domain comprises a polypeptide having at least 70%, 75%, 80%, 85%, 90%, 95%, or more homology to a sequence described in Table 9 (SEQ ID NO: 113-140). In some embodiments, the HSA binding domain has a sequence comprising at least a portion of a sequence described in Table 9 (SEQ ID NO: 113-140). In some embodiments, the HSA binding domain comprises a polypeptide comprising one or more of the sequences described in Table 9 (SEQ ID NO: 113-140).

In some embodiments, PSMA binding domains described herein comprise a single domain antibody with a CDR1 comprising SE ID NO: 114-116, and 125. In some embodiments, PSMA binding domains described herein comprise a single domain antibody with a CDR1 comprising SEQ ID NO: 117-123, and 126. In some embodiments, PSMA binding domains described herein comprise a single domain antibody with a CDR1 comprising SE ID NO: 124 and 127.

PSMA Trispecific Protein Modifications

The PSMA targeting trispecific proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in PSMA targeting trispecific proteins described herein, including the peptide backbone, the amino acid side-chains, and the amino or carboxyl termini. Certain common peptide modifications that are useful for modification of PSMA targeting trispecific proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding PSMA Targeting Trispecific Proteins

Also provided, in some embodiments, are polynucleotide molecules encoding a PSMA trispecific antigen-binding protein described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. In the embodiments where the PSMA binding domain is a small molecule, the polynucleotides contain genes encoding the CD3 binding domain and the half-life extension domain. In the embodiments where the half-life extension domain is a small molecule, the polynucleotides contain genes encoding the domains that bind to CD3 and PSMA. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described trispecific antigen-binding protein. Examples of expression vectors for expression in *E. coli* are pSKK (Le Gall et al., J Immunol Methods. (2004) 285(1):111-27) or pcDNA5 (Invitrogen) for expression in mammalian cells.

Thus, the PSMA targeting trispecific proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising a PSMA trispecific antigen-binding protein described herein, a vector comprising the polynucleotide encoding the polypeptide of the PSMA targeting trispecific proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the PSMA targeting trispecific proteins described herein are encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the PSMA trispecific antigen-binding protein is attached to liposomes. In some instances, the PSMA trispecific antigen-binding protein are conjugated to the surface of liposomes. In some instances, the PSMA trispecific antigen-binding protein are encapsulated within the shell of a liposome. In some instances, the liposome is a cationic liposome.

The PSMA targeting trispecific proteins described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

Methods of Treatment

Also provided herein, in some embodiments, are methods and uses for stimulating the immune system of an individual in need thereof comprising administration of a PSMA targeting trispecific protein described herein. In some instances, the administration of a PSMA targeting trispecific protein described herein induces and/or sustains cytotoxicity towards a cell expressing PSMA. In some instances, the cell expressing PSMA is a cancer cell.

Also provided herein are methods and uses for a treatment of a disease, disorder or condition associated with PSMA comprising administering to an individual in need thereof a PSMA targeting trispecific protein described herein. Diseases, disorders or conditions associated with PSMA include, but are not limited to, a proliferative disease or a tumorous disease. In one embodiment, the disease, disorder or condition associated with PSMA is prostate cancer. In another embodiment, the disease, disorder, or condition associated with PSMA is renal cancer.

In some embodiments, the prostate cancer is an advanced stage prostate cancer. In some embodiments, the prostate cancer is drug resistant. In some embodiments, the prostate cancer is anti-androgen drug resistant. In some embodiments, the prostate cancer is metastatic. In some embodiments, the prostate cancer is metastatic and drug resistant (e.g., anti-androgen drug resistant). In some embodiments, the prostate cancer is castration resistant. In some embodiments, the prostate cancer is metastatic and castration resistant. In some embodiments, the prostate cancer is enzalutamide resistant. In some embodiments, the prostate cancer is enzalutamide and arbiraterone resistant. In some embodiments, the prostate cancer is enzalutamide, arbiraterone, and bicalutamide resistant. In some embodiments, the prostate cancer is docetaxel resistant. In some of these embodiments, the prostate cancer is enzalutamide, arbiraterone, bicalutamide, and docetaxel resistant.

In some embodiments, administering a PSMA targeting trispecific protein described herein inhibits prostate cancer cell growth; inhibits prostate cancer cell migration; inhibits prostate cancer cell invasion; ameliorates the symptoms of prostate cancer; reduces the size of a prostate cancer tumor; reduces the number of prostate cancer tumors; reduces the number of prostate cancer cells; induces prostate cancer cell necrosis, pyroptosis, oncosis, apoptosis, autophagy, or other cell death; or enhances the therapeutic effects of a compound selected from the group consisting of enzalutamide, abiraterone, docetaxel, bicalutamide, and any combinations thereof.

In some embodiments, the method comprises inhibiting prostate cancer cell growth by administering a PSMA targeting trispecific protein described herein. In some embodiments, the method comprises inhibiting prostate cancer cell migration by administering a PSMA targeting trispecific protein described herein. In some embodiments, the method comprises inhibiting prostate cancer cell invasion by administering a PSMA targeting trispecific protein described herein. In some embodiments, the method comprises ameliorating the symptoms of prostate cancer by administering a PSMA targeting trispecific protein described herein. In some embodiments, the method comprises reducing the size of a prostate cancer tumor by administering a PSMA targeting trispecific protein described herein. In some embodiments, the method comprises reducing the number of prostate cancer tumors by administering a PSMA targeting trispecific protein described herein. In some embodiments, the method comprises reducing the number of prostate cancer cells by administering a PSMA targeting trispecific protein described herein. In some embodiments, the method comprises inducing prostate cancer cell necrosis, pyroptosis, oncosis, apoptosis, autophagy, or other cell death by administering a PSMA targeting trispecific protein described herein.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as prostate cancer).

In some embodiments of the methods described herein, the PSMA targeting trispecific proteins are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, the PSMA targeting trispecific proteins are administered in combination with anti-diarrheal agents, anti-emetic agents, analgesics, opioids and/or non-steroidal anti-inflammatory agents. In some embodiments, the PSMA targeting trispecific proteins are administered before, during, or after surgery.

Certain Definitions

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are $time^{-1}$ and time, respectively. A first-order rate constant and the half-time of the reaction are simply related ($k \times t_{1/2} = 0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the phrase "prostate cancer" or "advanced stage prostate cancer" includes a class of prostate cancers that has progressed beyond early stages of the disease. Typically, advanced stage prostate cancers are associated with a poor prognosis. Types of advanced stage prostate cancers include, but are not limited to, metastatic prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer, and the like), hormone refractory prostate cancer, castration-resistant prostate cancer, metastatic castration-resistant prostate cancer, docetaxel-resistant prostate cancer, androgen receptor splice variant-7 (AR-V7)-induced drug-resistant prostate cancer such as AR-V7-induced anti-androgen-resistant prostate cancer (e.g., AR-V7-induced enzalutamide-resistant prostate cancer), aldo-keto reductase family 1 member C3 (AKR1C3)-induced drug-resistant prostate cancer such as AKR1C3-induced anti-androgen-resistant prostate cancer (e.g., AKR1C3-induced enzalutamide-resistant prostate cancer), and combinations thereof. In some instances, the advanced stage prostate cancers do not generally respond, or are resistant, to treatment with one or more of the following conventional prostate cancer therapies: enzalutamide, abiraterone, bicalutamide, and docetaxel. Compounds, compositions, and methods of the present disclosure are provided for treating prostate cancer, such as advanced stage prostate cancer, including any one or more (e.g., two, three, four, five, six, seven, eight, nine, ten, or more) of the types of advanced stage prostate cancers disclosed herein.

EXAMPLES

Example 1: Methods to Assess Binding and Cytotoxic Activities of Trispecific Antigen Binding Molecules Protein Production Sequences of trispecific molecules were cloned into mammalian expression vector pcDNA 3.4 (Invitrogen) preceded by a leader sequence and followed by a 6× Histidine Tag (SEQ ID NO: 161). Expi293F cells (Life Technologies A14527) were maintained in suspension in Optimum Growth Flasks (Thomson) between 0.2 to 8×1e6 cells/ml in Expi293 media. Purified plasmid DNA was transfected into Expi293 cells in accordance with Expi293 Expression System Kit (Life Technologies, A14635) protocols, and maintained for 4-6 days post transfection. Conditioned media was partially purified by affinity and desalting chromatography. Trispecific proteins were subsequently polished by ion exchange or, alternatively, concentrated with AMICON® Ultra centrifugal filtration units (EMD Millipore), applied to SUPERDEX™ 200 size exclusion media (GE Healthcare) and resolved in a neutral buffer containing excipients. Fraction pooling and final purity were assessed by SDS-PAGE and analytical SEC.

Affinity Measurements

The affinities of the all binding domains molecules were measured by biolayer inferometry using an Octet instrument.

PSMA affinities were measured by loading human PSMA-Fc protein (100 nM) onto anti-human IgG Fc biosensors for 120 seconds, followed by a 60 second baseline, after which associations were measured by incubating the sensor tip in a dilution series of the trispecific molecules for 180 seconds, followed by dissociation for 50 seconds. EGFR and CD3 affinities were measured by loading human EGFR-Fc protein or human CD3-Flag-Fc protein, respectively, (100 nM) onto anti-human IgG Fc biosensors for 120 seconds, followed by a 60 second baseline, after which associations were measured by incubating the sensor tip in a dilution series of the trispecific molecules for 180 seconds, followed by dissociation for 300 seconds. Affinities to human serum albumin (HSA) were measured by loading biotinylated albumin onto streptavidin biosensors, then following the same kinetic parameters as for CD3 affinity measurements. All steps were performed at 30° C. in 0.25% casein in phosphate-buffered saline.

Cytotoxicity Assays

A human T-cell dependent cellular cytotoxicity (TDCC) assay was used to measure the ability of T cell engagers, including trispecific molecules, to direct T cells to kill tumor cells (Nazarian et al. 2015. J Biomol Screen. 20:519-27). In this assay, T cells and target cancer cell line cells are mixed together at a 10:1 ratio in a 384 wells plate, and varying amounts of T cell engager are added. After 48 hours, the T cells are washed away leaving attached to the plate target cells that were not killed by the T cells. To quantitate the remaining viable cells, CELLTITER-GLO® Luminescent Cell Viability Assay (Promega) is used. In some cases, the target cells are engineered to express luciferase. In these cases, viability of the target cells is assessed by performing a luminescent luciferase assay with STEADYGLO® reagent (Promega), where viability is directly proportional to the amount of luciferase activity.

Stability Assays

The stability of the trispecific binding proteins was assessed at low concentrations in the presence of non-human primate serum. TRITAC™ molecules were diluted to 33 µg/ml in Cynomolgus serum (BioReclamationIVT) and either incubated for 2 d at 37° C. or subjected to five freeze/thaw cycles. Following the treatment, the samples were assessed in cytotoxicity (TDCC) assays and their remaining activity was compared to untreated stock solutions.

Xenograft Assays

The in vivo efficacy of trispecific binding proteins was assessed in xenograft experiments (Crown Bioscience, Taicang). NOD/SCID mice deficient in the common gamma chain (NCG, Model Animal Research Center of Nanjing University) were inoculated on day 0 with a mixture of 5e6 22Rv1 human prostate cancer cells and 5e6 resting, human T cells that were isolated from a healthy, human donor. The mice were randomized into three groups, and treated with vehicle, 0.5 mg/kg PSMA TRITAC™ C324 or 0.5 mg/kg PSMA BiTE. Treatments were administered daily for 10 days via i.v. bolus injection. Animals were checked daily for morbidity and mortality. Tumor volumes were determined twice weekly with a caliper. The study was terminated after 30 days.

PK Assays

The purpose of this study was to evaluate the single dose pharmacokinetics of trispecific binding proteins following intravenous injection. 2 experimentally naïve cynomolgus monkeys per group (1 male and 1 female) were given compound via a slow IV bolus injection administered over approximately 1 minute. Following dose administration, cage side observations were performed once daily and body weights were recorded weekly. Blood samples were collected and processed to serum for pharmacokinetic analysis through 21 days post dose administration.

Concentrations of test articles were determined from monkey serum with an electroluminescent readout (Meso Scale Diagnostics, Rockville). 96 well plates with immobilized, recombinant CD3 were used to capture the analyte. Detection was performed with sulfo-tagged, recombinant PSMA on a MSD reader according to the manufacturer's instructions.

Figure 2A:
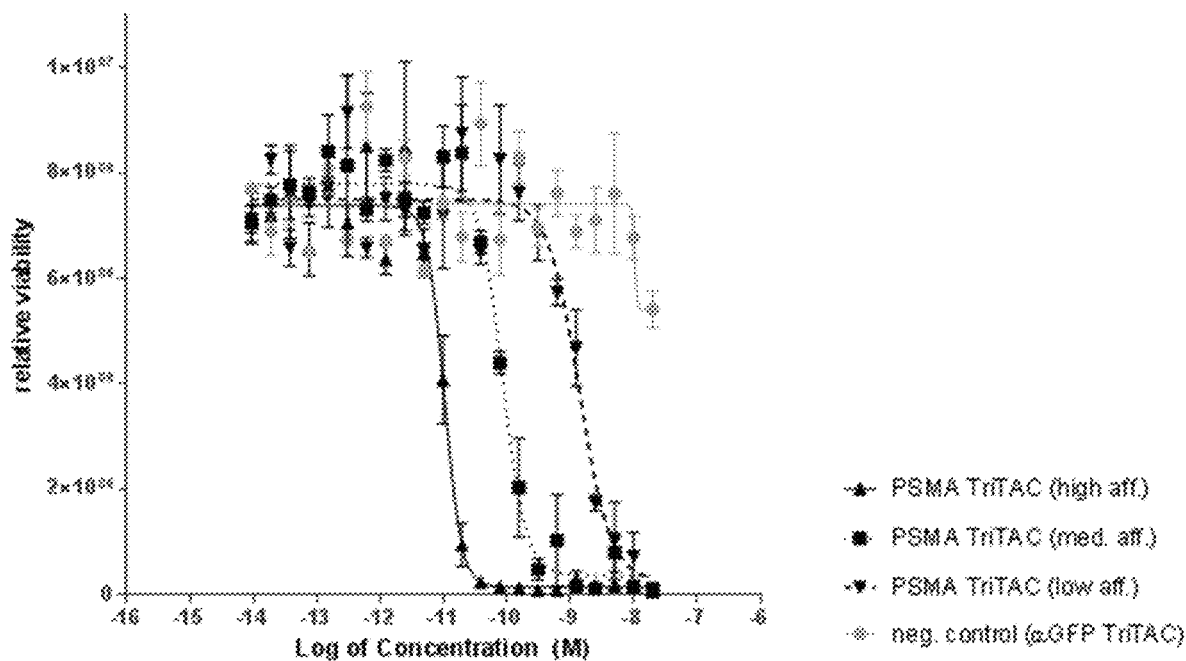
FIGS. 2A-B compare the ability of exemplary PSMA targeting trispecific proteins (PSMA targeting TRITAC™ molecules) with different affinities for CD3 to induce T cells to kill human prostate cancer cells.
Figure 2B:
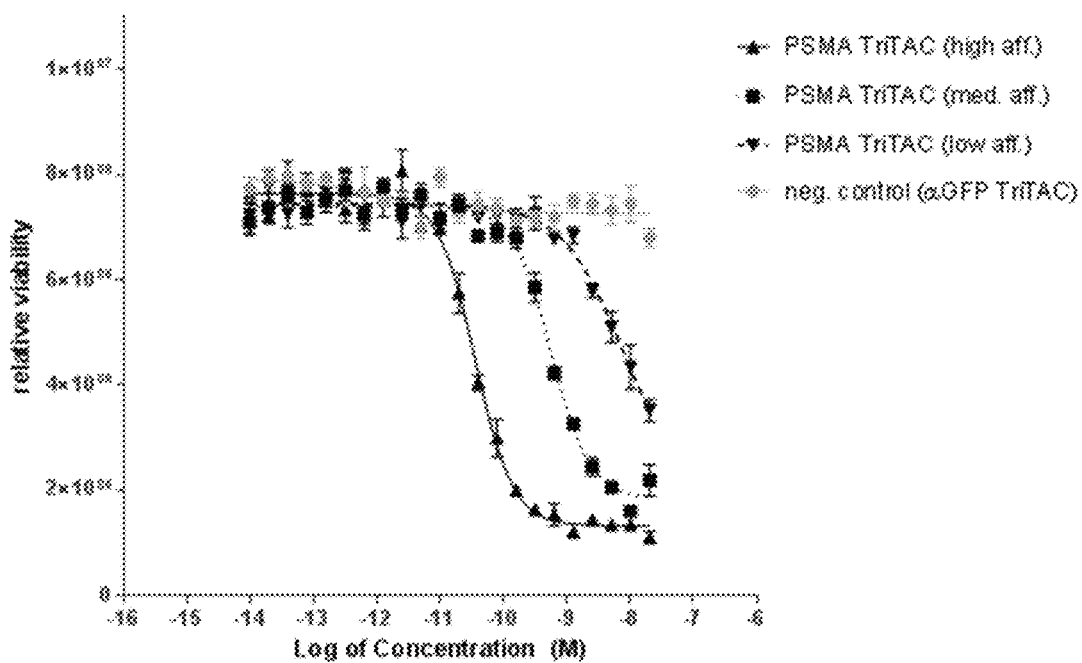
Figures 2C, 3:
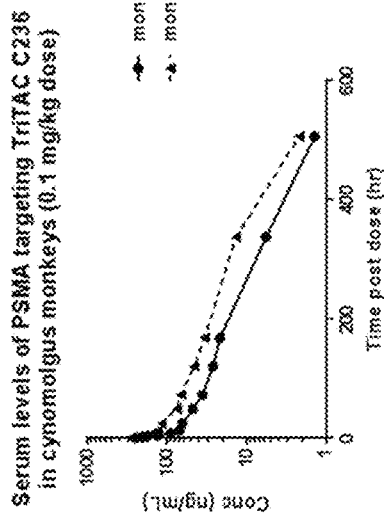
FIG. 2C shows EC50 values for targeting TRITAC™ molecules in LNCaP and 22Rv1 prostate cancer models.
FIG. 3 shows the serum concentration of PSMA targeting TRITAC™ C236 in Cynomolgus monkeys after i.v. administration (100 μg/kg) over three weeks.
Figure 4:
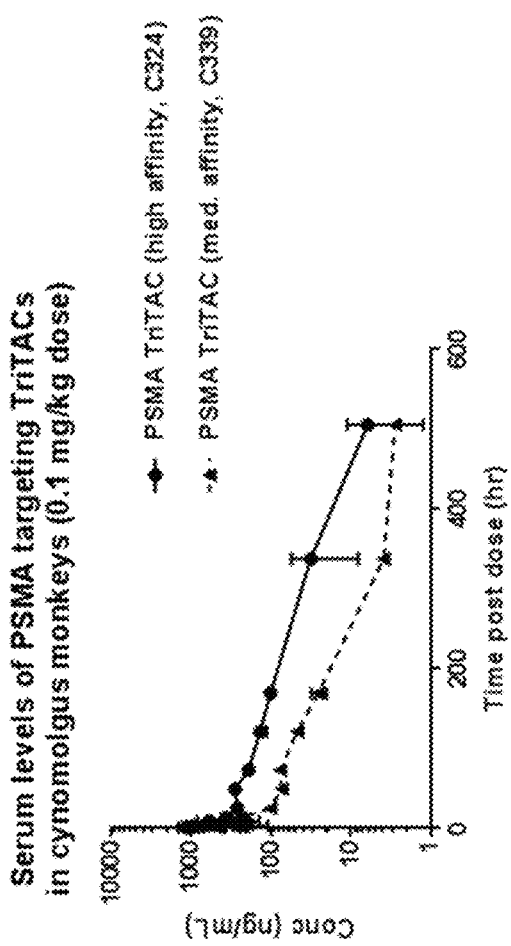
FIG. 4 shows the serum concentration of PSMA targeting TRITAC™ molecules with different CD3 affinities in Cynomolgus monkeys after i.v. administration (100 μg/kg) over three weeks.

Example 2: Assessing the Impact of CD3 Affinity on the Properties of Trispecific Molecules PSMA targeting trispecific molecules with distinct CD3 binding domains were studied to demonstrate the effects of altering CD3 affinity. An exemplary PSMA targeting trispecific molecule is illustrated in FIG. 1. Table 1 lists the affinity of each molecule for the three binding partners (PSMA, CD3, HSA). Affinities were measured by biolayer interferometry using an Octet instrument (Pall Forté Bio). Reduced CD3 affinity leads to a loss in potency in terms of T cell mediated cellular toxicity (FIGS. 2A-C). The pharmacokinetic properties of these trispecific molecules was assessed in cynomolgus monkeys. Molecules with high affinity for CD3 like TRITAC™ C236 have a terminal half-life of approx. 90 h (FIG. 3). Despite the altered ability to bind CD3 on T cells, the terminal half-life of two molecules with different CD3 affinities shown in FIG. 4 is very similar. However, the reduced CD3 affinity appears to lead to a larger volume of distribution, which is consistent with reduced sequestration of trispecific molecule by T cells. There were no adverse clinical observations or body weight changes noted during the study period.

TABLE 1

Binding Affinities for Human and Cynomolgus Antigens

| | anti-PSMA KD value (nM) | | | anti-Albumin KD value (nM) | | | anti-CD3e KD value (nM) | | |
|---|---|---|---|---|---|---|---|---|---|
| | human | cyno | ratio cyno/hum | pHSA | CSA | ratio cyno/hum | human | cyno | ratio cyno/hum |
| Tool TRITAC ™ high aff. - C236 | 16.3 | 0 | 0 | 22.7 | 25.4 | 1.1 | 6.0 | 4.7 | 0.8 |
| TRITAC ™ CD3 high aff. - C324 | 17.9 | 0 | 0 | 9.8 | 9.7 | 1 | 7.4 | 5.8 | 0.8 |
| TRITAC ™ CD3 med aff. - C339 | 13.6 | 0 | 0 | 8.8 | 8.3 | 0.9 | 40.6 | 33.6 | 0.8 |
| TRITAC ™ CD3 low aff - C325 | 15.3 | 0 | 0 | 10.1 | 9.7 | 1 | 217 | 160 | 0.7 |

Figure 5A:
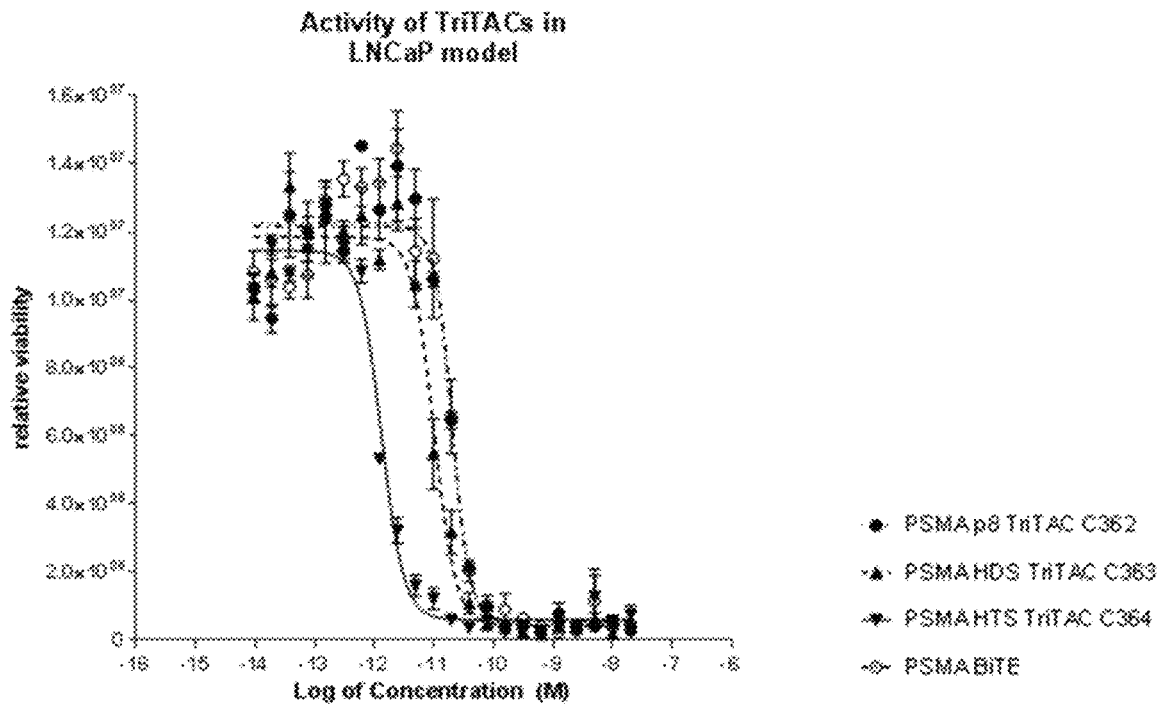
FIGS. 5A-C show the ability of PSMA targeting TRITAC™ molecules with different affinities for PSMA to induce T cells to kill the human prostate cancer cell line LNCaP.
Figure 5B:
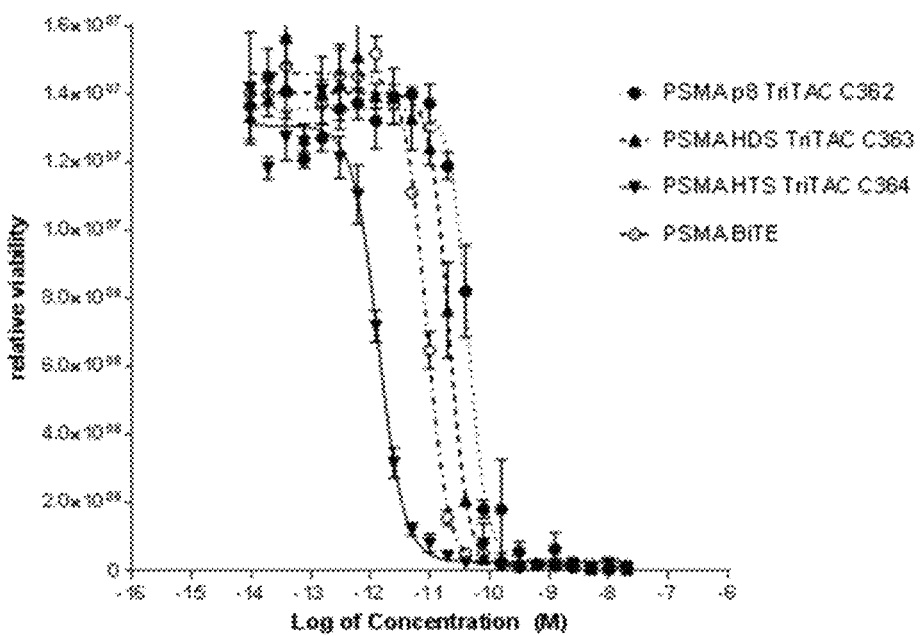
Figures 5C, 6:
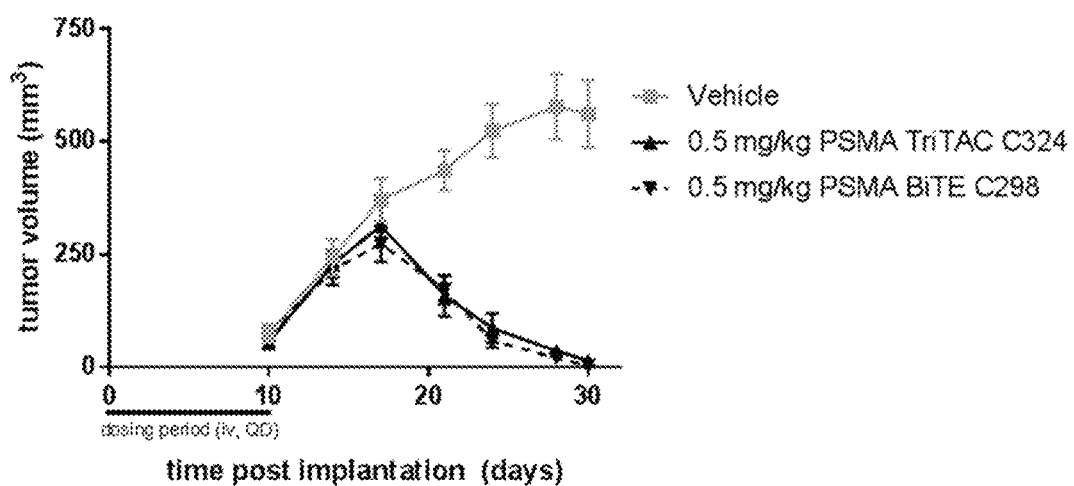
FIG. 6 demonstrates the ability of PSMA targeting TRITAC™ molecules to inhibit tumor growth of human prostate cancer cells in a mouse xenograft experiment.
Figures 7A, 7B:
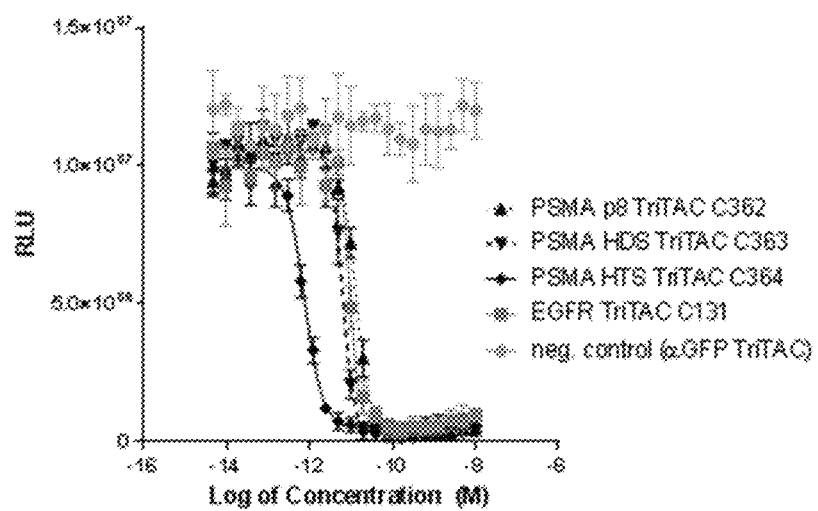
FIGS. 7A-D illustrates the specificity of TRITAC™ molecules in cell killing assays with target cell lines that do or do not express the target protein.
Figure 7C:
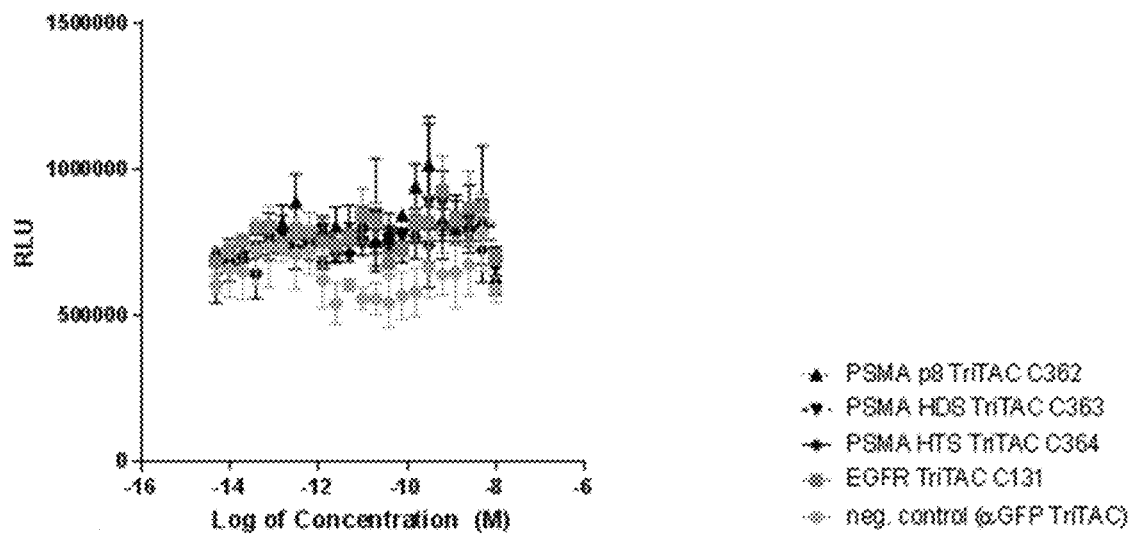
Figure 7D:
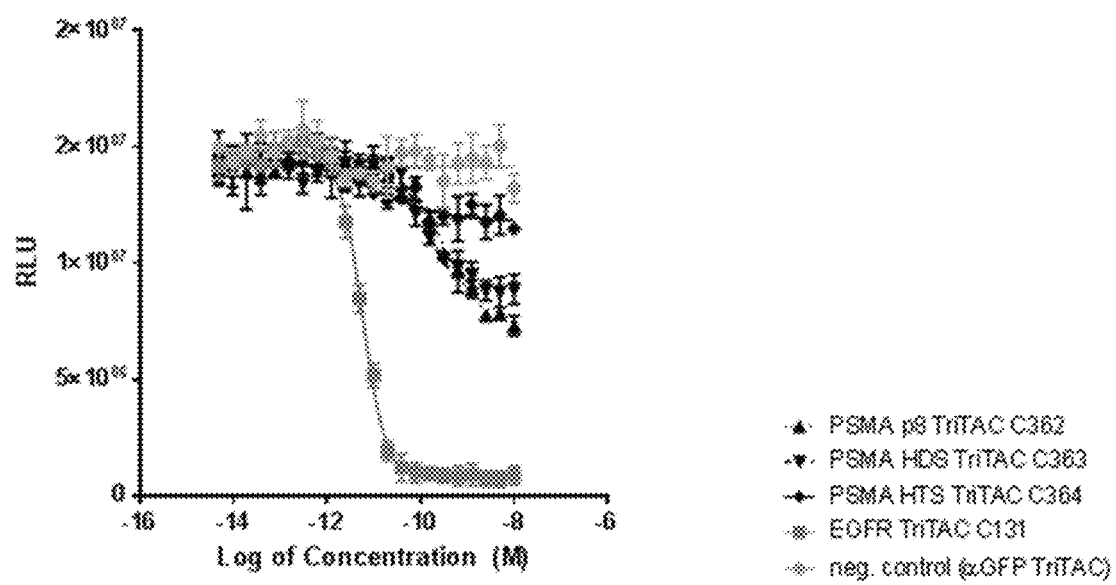
Figure 8A:
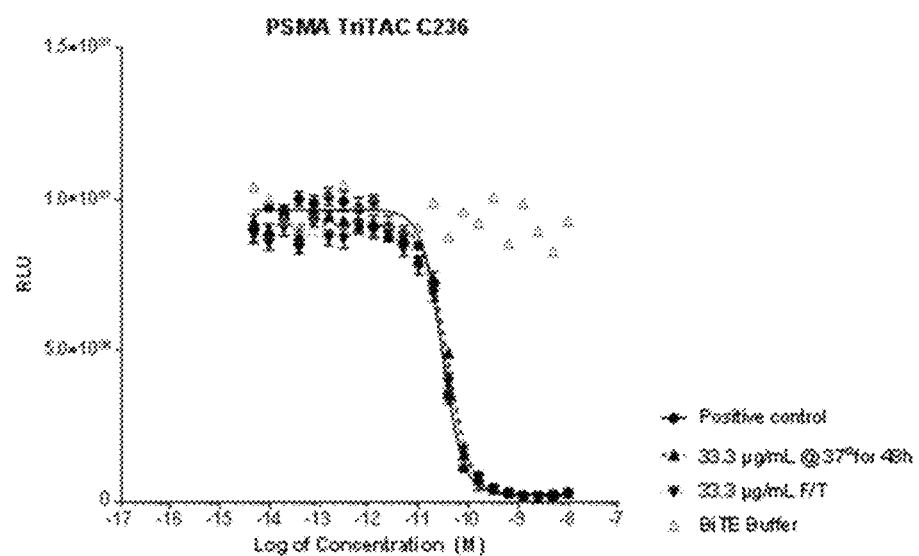
FIGS. 8A-D depict the impact of pre-incubation at 37° C. and freeze/thaw cycles on TRITAC™ activity.
Figure 8B:
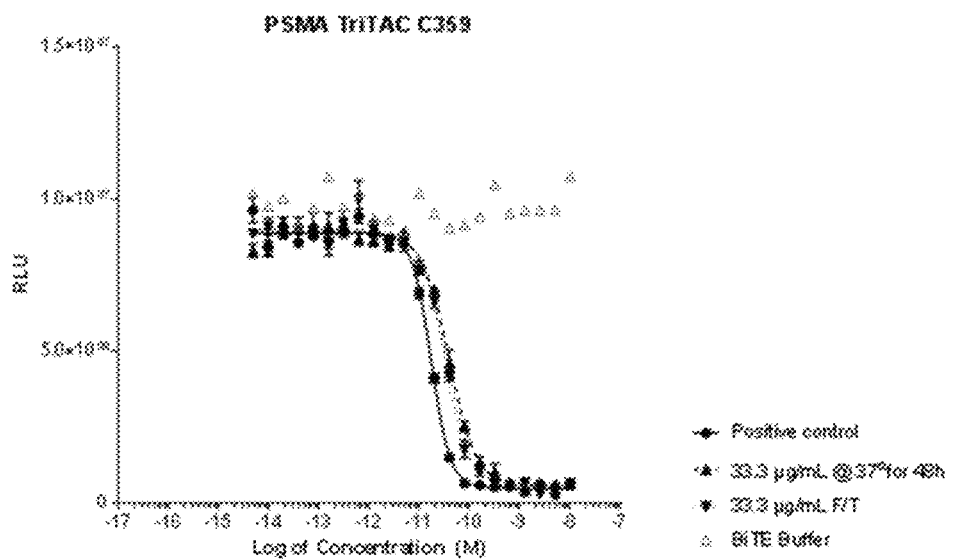
Figure 8C:
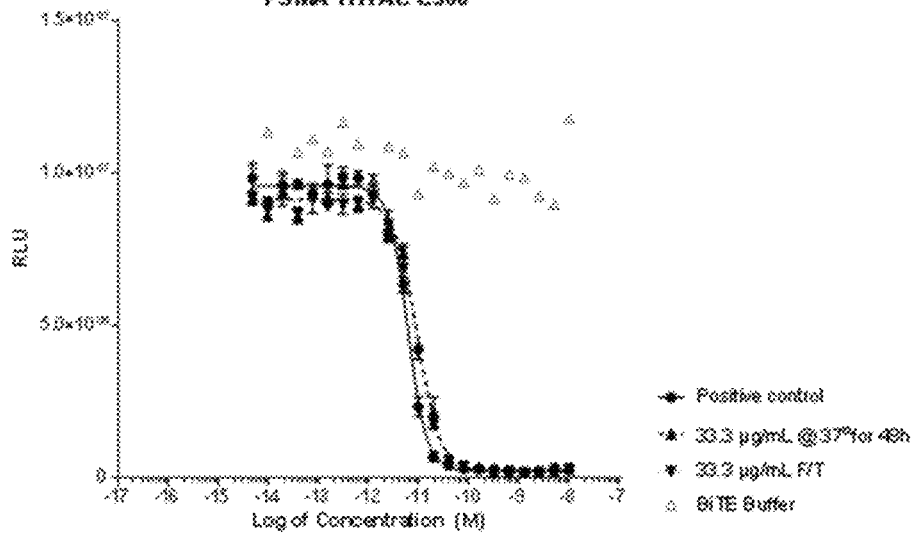
Figure 8D:
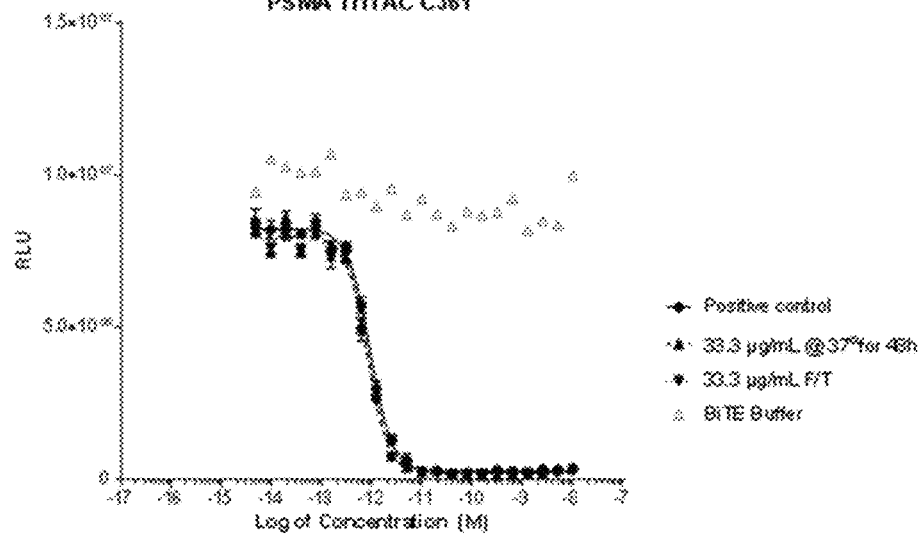

Example 3: Assessing the Impact of PSMA Affinity on the Properties of Trispecific Molecules PSMA targeting trispecific molecules with distinct PSMA binding domains were studied to demonstrate the effects of altering PSMA affinity. Table 2 lists the affinity of each molecule for the three binding partners (PSMA, CD3, HSA). Reduced PSMA affinity leads to a loss in potency in terms of T cell mediated cellular toxicity (FIGS. 5A-C).

expected activity against the PSMA positive cell line LNCaP (FIG. 7B), but did not reach EC50s in the PSMA negative tumor cell lines KMS12BM and OVCAR8 (FIGS. 7C and 7D). The EC50s are summarized in Table 3. At very high TRITAC™ concentrations (>1 nM), some limited off-target cell killing could be observed for TRITAC™ molecules C362 and C363, while C364 did not show significant cell killing under any of the tested conditions.

TABLE 2

Binding Affinities for Human and Cynomolgus Antigens

| | anti-PSMA KD value (nM) | | | anti-Albumin KD value (nM) | | | anti-CD3e KD value (nM) | | |
|---|---|---|---|---|---|---|---|---|---|
| | human | cyno | ratio cyno/hum | pHSA | CSA | ratio cyno/hum | human | cyno | ratio cyno/hum |
| PSMA-TRITAC ™ (p8)-C362 | 22.0 | 0 | n/a | 6.6 | 6.6 | 1.0 | 8.3 | 4.3 | 0.52 |
| PSMA TRITAC ™ (HDS) - C363 | 3.7 | 540 | 146 | 7.6 | 8.4 | 1.1 | 8.0 | 5.2 | 0.65 |
| PSMA TRITAC ™ (HTS)- C364 | 0.15 | 663 | 4423 | 8.4 | 8.6 | 1.0 | 7.7 | 3.8 | 0.49 |

Example 4: In Vivo Efficacy of PSMA Targeting Trispecific Molecules

The PSMA targeting trispecific molecule C324 was assessed for its ability to inhibit the growth of tumors in mice. For this experiment, immunocompromised mice reconstituted with human T cells were subcutaneously inoculated with PSMA expressing human prostate tumor cells (22Rv1) and treated daily for 10 days with 0.5 mg/kg i.v. of either PSMA targeting BiTE or TRITAC™ molecules. Tumor growth was measured for 30. Over the course of the experiment, the trispecific molecule was able to inhibit tumor growth with an efficacy comparable to a BiTE molecule (FIG. 6).

Example 5: Specificity of Trispecific Molecules

In order to assess the specificity of PSMA targeting TRITAC™ molecules, their ability to induce T cells to kill tumor cells was tested with tumor cells that are negative for PSMA (FIG. 7A). An EGFR targeting TRITAC™ molecule served as positive control, a GFP targeting TRITAC™ molecule as negative control. All three TRITAC™ molecules with distinct PSMA binding domains showed the

TABLE 3

Cell killing activity of TRITAC ™ molecules in with antigen positive and negative tumor cell lines (EC50 [pM])

| TRITAC ™ | LNCaP | KMS12BM | OVCAR8 |
|---|---|---|---|
| PSMA p8 TRITAC ™ C362 | 13.0 | >10,000 | >10,000 |
| PSMA HDS TRITAC ™ C363 | 6.2 | >10,000 | >10,000 |
| PSMA HTS TRITAC ™ C364 | 0.8 | >10,000 | >10,000 |
| EGFR TRITAC ™ C131 | 9.4 | >10,000 | 6 |
| GFP TRITAC ™ C | >10,000 | >10,000 | >10,000 |

Example 6: Stress Tests and Protein Stability

Four PSMA targeting trispecific molecules were either incubated for 48 h in Cynomolgus serum at low concentrations (33.3 μg/ml) or subjected to five freeze thaw cycles in Cynomolgus serum. After the treatment, the bio-activity of the TRITAC™ molecules was assessed in cell killing assays and compared to unstressed samples ("positive control", FIG. 8A-D). All molecules maintained the majority of their cell killing activity. TRITAC™ C362 was the most stress resistant and did not appear to lose any activity under the conditions tested here.

Example 7: Xenograft Tumor Model

The PSMA targeting trispecific proteins of the previous examples are evaluated in a xenograft model.

Male immune-deficient NCG mice are subcutaneously inoculated with 5×106 22Rv1 cells into their the right dorsal flank. When tumors reach 100 to 200 mm3, animals are allocated into 3 treatment groups. Groups 2 and 3 (8 animals each) are intraperitoneally injected with 1.5×107 activated human T-cells. Three days later, animals from Group 3 are subsequently treated with a total of 9 intravenous doses of 50 µg PSMA trispecific antigen-binding protein of Example 1 (qd×9d). Groups 1 and 2 are only treated with vehicle. Body weight and tumor volume are determined for 30 days. It is expected that tumor growth in mice treated with the PSMA trispecific antigen-binding protein is significantly reduced in comparison to the tumor growth in respective vehicle-treated control group.

Example 8: Proof-of-Concept Clinical Trial Protocol for Administration of the PSMA Trispecific Antigen-Binding Protein of Example 1 to Prostate Cancer Patients This is a Phase I/II clinical trial for studying the PSMA trispecific antigen-binding protein of Example 1 as a treatment for Prostate Cancer.

Study Outcomes:

Primary: Maximum tolerated dose of PSMA targeting trispecific proteins of the previous examples Secondary: To determine whether in vitro response of PSMA targeting trispecific proteins of is the previous examples are associated with clinical response Phase I The maximum tolerated dose (MTD) will be determined in the phase I section of the trial.

1.1 The maximum tolerated dose (MTD) will be determined in the phase I section of the trial.

1.2 Patients who fulfill eligibility criteria will be entered into the trial to PSMA targeting trispecific proteins of the previous examples.

1.3 The goal is to identify the highest dose of PSMA targeting trispecific proteins of the previous examples that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of PSMA targeting trispecific proteins of the previous examples results in at least a 20% response rate.

Primary Outcome for the Phase II—To determine if therapy of PSMA targeting trispecific proteins of the previous examples results in at least 20% of patients achieving a clinical response (blast response, minor response, partial response, or complete response)

Eligibility:

Histologically confirmed newly diagnosed aggressive prostate cancer according to the current World Health Organisation Classification, from 2001 to 2007

Any stage of disease.

Treatment with docetaxel and prednisone (+/− surgery).

Age≥18 years

Karnofsky performance status≥50% or ECOG performance status 0-2

Life expectancy≥6 weeks

Example 9: Activity of an Exemplary PSMA Antigen-Binding Protein (PSMA Targeting TRITAC™ Molecule) in Redirected T Cell Killing Assays Using a Panel of PSMA Expressing Cell Lines and T Cells from Different Donors This study was carried out to demonstrate that the activity of the exemplary PSMA trispecific antigen-binding protein is not limited to LNCaP cells or a single cell donor.

Redirected T cell killing assays were performed using T cells from four different donors and the human PSMA-expressing prostate cancer cell lines VCaP, LNCaP, MDAPCa2b, and 22Rv1. With one exception, the PSMA trispecific antigen-binding protein was able to direct killing of these cancer cell lines using T cells from all donors with $EC_{50}$ values of 0.2 to 1.5 pM, as shown in Table 4. With the prostate cancer cell line 22 Rv1 and Donor 24, little to no killing was observed (data not shown). Donor 24 also only resulted approximately 50% killing of the MDAPCa2b cell line whereas T cells from the other 3 donors resulted in almost complete killing of this cell line (data not shown). Control assays demonstrated that killing by the PSMA trispecific antigen-binding protein was PSMA specific. No killing was observed when PSMA-expressing cells were treated with a control trispecific protein targeting green fluorescent protein (GFP) instead of PSMA (data not shown). Similarly, the PSMA trispecific antigen-binding protein was inactive with cell lines that lack PSMA expression, NCI-1563 and HCT116, also shown in Table 4.

TABLE 4

$EC_{50}$ Values from TDCC Assays with Six Human Cancer Cell Lines and Four Different T Cell Donors

| Cell Line | TDCC $EC_{50}$ Values (M) | | | |
| --- | --- | --- | --- | --- |
| | Donor 24 | Donor 8144 | Donor 72 | Donor 41 |
| LNCaP | 1.5E−12 | 2.2E−13 | 3.6E−13 | 4.3E−13 |
| MDAPCa2b | 4.8E−12 | 4.1E−13 | 4.9E−13 | 6.5E−13 |
| VCaP | 6.4E−13 | 1.6E−13 | 2.0E−13 | 3.5E−13 |
| 22Rv1 | n/a | 7.2E−13 | 1.4E−12 | 1.3E−12 |
| HCT116 | >1.0E−8 | >1.0E−8 | >1.0E−8 | >1.0E−8 |
| NCI-1563 | >1.0E−8 | >1.0E−8 | >1.0E−8 | >1.0E−8 |

Example 10: Stimulation of Cytokine Expression in by an Exemplary PSMA Trispecific Antigen-Binding Protein (PSMA Targeting TRITAC™ Molecule) in Redirected T Cell Killing Assays This study was carried out to demonstrate activation of T cells by the exemplary PSMA trispecific antigen-binding protein during redirected T cell killing assays by measuring secretion of cytokine into the assay medium by activated T cells.

Conditioned media collected from redirected T cell killing assays, as described above in Example 9, were analyzed for expression of the cytokines TNFα and IFNγ. Cytokines were measured using AlphaLISA assays (Perkin-Elmer). Adding a titration of the PSMA antigen-binding protein to T cells from four different donors and four PSMA-expressing cell lines, LNCaP, VCaP, MDAPCa2b, and 22Rv1 resulted in increased levels of TNFα. The results for TNFα expression and IFN γ expression levels in the conditioned media are shown in Tables 5 and 6, respectively. The $EC_{50}$ values for the PSMA antigen-binding protein induced expression of these cytokines ranged from 3 to 15 pM. Increased cytokine levels were not observed with a control trispecific protein targeting GFP. Similarly, when assays were performed with two cell lines that lack PSMA expression, HCT116 and NCI-H1563, PSMA HTS TRITAC™ also did not increase TNFα or IFNγ expression.

TABLE 5

$EC_{50}$ Values for TNFα Expression in Media from PSMA Trispecific Antigen-Binding Protein TDCC Assays with Six Human Cancer Cell Lines and T Cells from Four Different Donors

| Cell Line | Donor 24 | Donor 8144 | Donor 41 | Donor72 |
|---|---|---|---|---|
| LNCaP | 4.9E-12 | 2.8E-12 | 4.0E-12 | 3.2E-12 |
| VCaP | 3.2E-12 | 2.9E-12 | 2.9E-12 | 2.9E-12 |
| MDAPCa2b | 2.1E-11 | 4.0E-12 | 5.5E-12 | 3.6E-12 |
| 22Rv1 | 8.9E-12 | 2.5E-12 | 4.0E-12 | 3.3E-12 |
| HCT116 | >1E-8 | >1E-8 | >1E-8 | >1E-8 |
| NCI-H1563 | >1E-8 | >1E-8 | >1E-8 | >1E-8 |

TABLE 6

$EC_{50}$ Values for IFNγ Expression in Media from PSMA Trispecific Antigen-Binding Protein TDCC Assays with Six Human Cancer Cell Lines and T Cells from Four Different Donors

| Cell Line | Donor 24 | Donor 8144 | Donor 41 | Donor72 |
|---|---|---|---|---|
| LNCaP | 4.2E-12 | 4.2E-12 | 4.2E-12 | 2.8E-12 |
| VCaP | 5.1E-12 | 1.5E-11 | 3.4E-12 | 4.9E-12 |
| MDAPCa2b | 1.5E-11 | 5.8E-12 | 9.7E-12 | 3.5E-12 |
| 22Rv1 | 7.8E-12 | 3.0E-12 | 9.1E-12 | 3.0E-12 |
| HCT116 | >1E-8 | >1E-8 | >1E-8 | >1E-8 |
| NCI-H1563 | >1E-8 | >1E-8 | >1E-8 | >1E-8 |

Example 11: Activity of an Exemplary PSMA Trispecific Antigen-Binding Protein (PSMA Targeting TRITAC™) in Redirected T Cell Killing Assay (TDCC) Using T Cells from Cynomolgus Monkeys This study was carried out to test the ability of the exemplary PSMA trispecific antigen-binding protein to direct T cells from cynomolgus monkeys to kill PSMA-expressing cell lines.

Figure 9A:
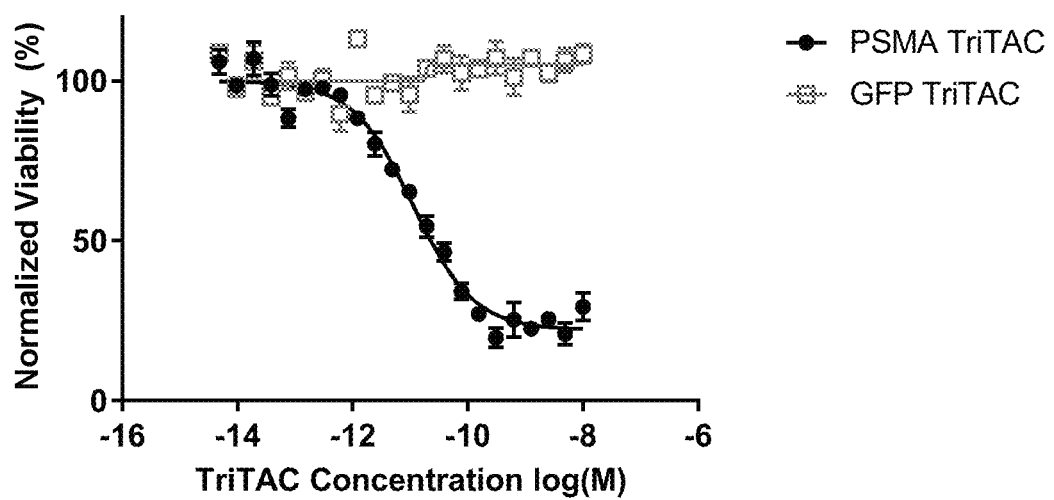
FIGS. 9A-B depict the activity of a PSMA targeting TRITAC™ molecule of this disclosure in redirected T cell killing in T cell dependent cellular cytotoxicity assays (TDCC).
Figure 9B:
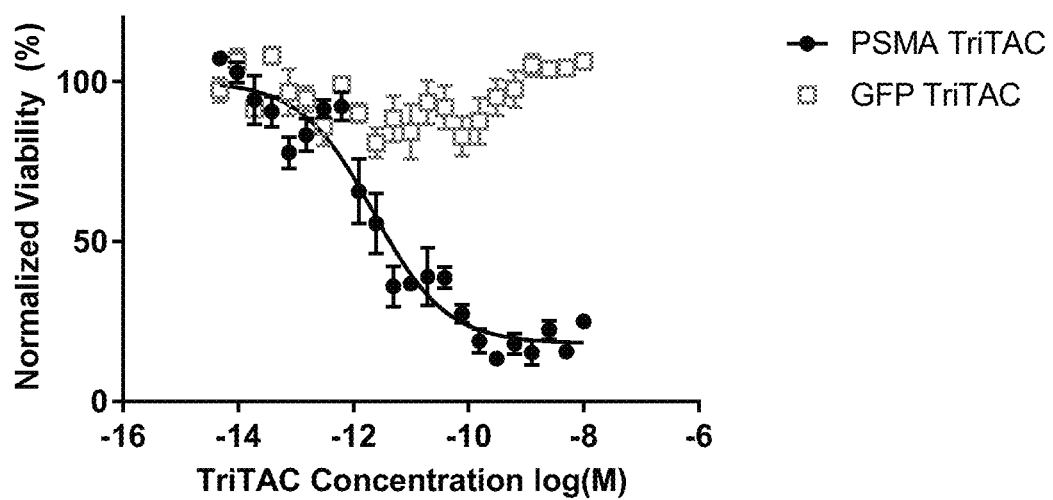

TDCC assays were set up using peripheral blood mononuclear cells (PBMCs) from cynomolgus monkeys. Cyno PBMCs were added to LNCaP cells at a 10:1 ratio. It was observed that the PSMA trispecific antigen-binding protein redirected killing of LNCaP by the cyno PBMCs with an $EC_{50}$ value of 11 pM. The result is shown in FIG. 9A. To confirm these results, a second cell line was used, MDAPCa2b, and PBMCs from a second cynomolgus monkey donor were tested. Redirected killing of the target cells was observed with an $EC_{50}$ value of 2.2 pM. The result is shown in FIG. 9B. Killing was specific to the anti PSMA arm of the PSMA trispecific antigen-binding protein as killing was not observed with a negative control trispecific protein targeting GFP. These data demonstrate that the PSMA antigen-binding trispecific protein can direct cynomolgus T cells to kill target cells expressing human PSMA.

Example 12: Expression of Markers of T Cell Activation in Redirect T Cell Killing Assays with an Exemplary PSMA Trispecific Antigen-Binding Protein (PSMA Targeting TRITAC™ Molecule)

This study was performed to assess whether T cells were activated when the exemplary PSMA trispecific antigen-binding protein directed the T cells to kill target cells.

Figure 10:
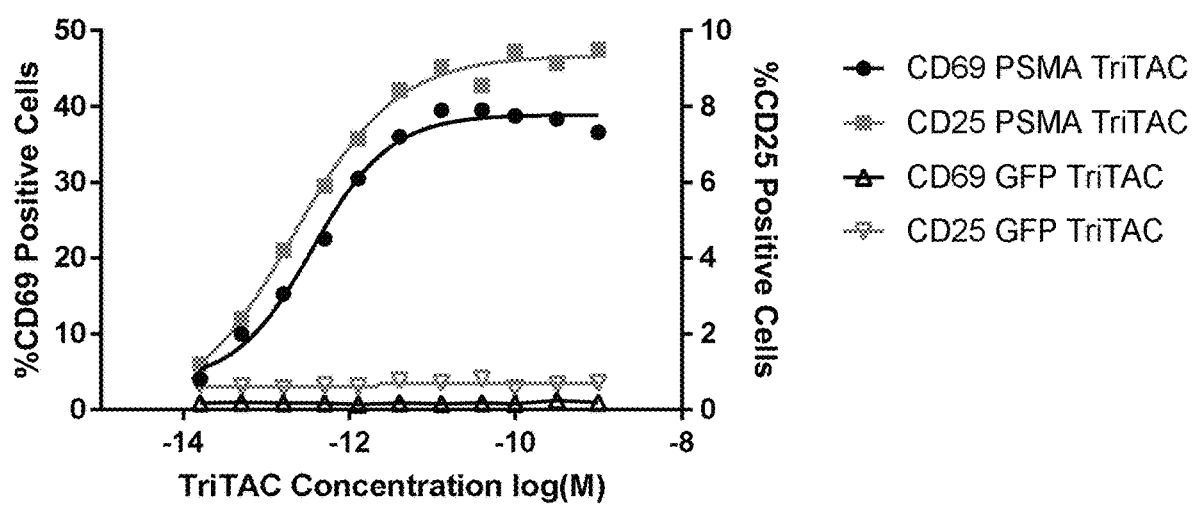
FIG. 10 depicts the impact of a PSMA targeting TRITAC™ molecule of this disclosure on expression of T cell activation markers CD25 and CD69.

The assays were set up using conditions for the redirected T cell killings assays described in the above example. T cell activation was assessed by measuring expression of CD25 and CD69 on the surface of the T cells using flow cytometry. The PSMA trispecific antigen-binding protein was added to a 10:1 mixture of purified human T cells and the prostate cancer cell line VCaP. Upon addition of increasing amounts of the PSMA trispecific antigen-binding protein, increased CD69 expression and CD25 expression was observed, as shown in FIG. 10. $EC_{50}$ value was 0.3 pM for CD69 and 0.2 pM for CD25. A trispecific protein targeting GFP was included in these assays as negative control, and little to no increase in CD69 or CD25 expression is observed with the GFP targeting trispecific protein, also shown in FIG. 10.

Example 13: Stimulation of T Cell Proliferation by an Exemplary PSMA Trispecific Antigen-Binding Protein (PSMA Targeting TRITAC™ Molecule) in the Presence of PSMA Expressing Target Cells This study was used as an additional method to demonstrate that the exemplary PSMA trispecific antigen-binding protein was able to activate T cells when it redirects them to kill target cells.

Figure 11:
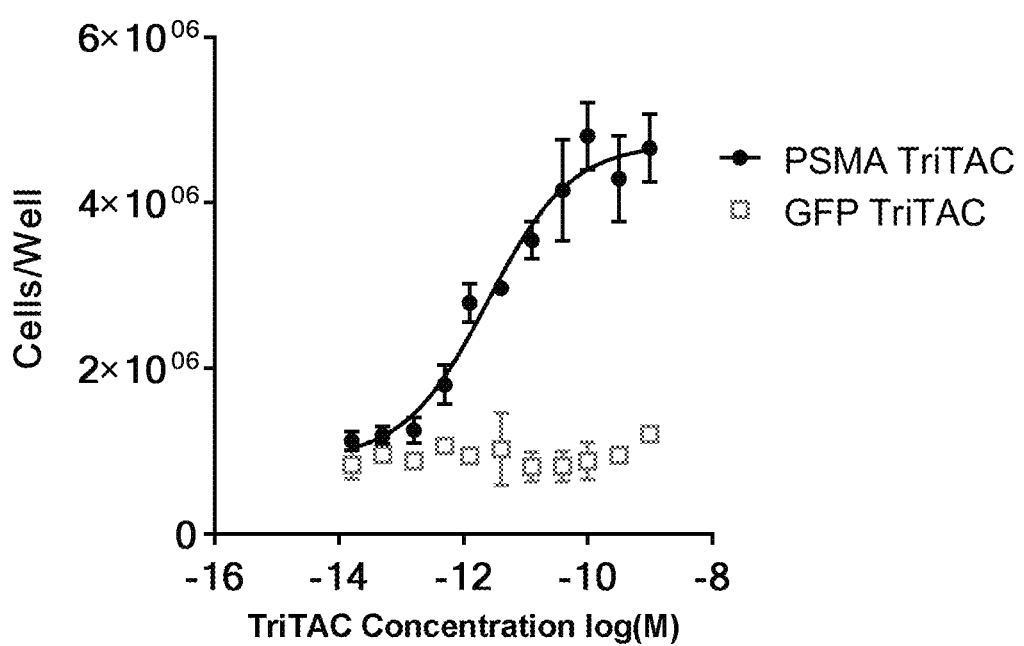
FIG. 11 depicts the ability of a PSMA targeting TRITAC™ molecule of this disclosure to stimulate T cell proliferation in the presence of PSMA expressing target cells.

T cell proliferation assays were set up using the conditions of the T cell redirected killing assay using LNCaP target cells, as described above, and measuring the number of T cells present at 72 hours. The exemplary PSMA trispecific antigen-binding protein stimulated proliferation with an $EC_{50}$ value of 0.5 pM. As negative control, a trispecific protein targeting GFP was included in the assay, and no increased proliferation was observed with this protein. The results for the T cell proliferation assay are illustrated in FIG. 11.

Example 14: Redirected T Cell Killing of LNCaP Cells by Three Exemplary PSMA Trispecific Antigen-Binding Proteins (PSMA Targeting TRITAC™ Molecules PH1T, PH, and Z2)

This study was carried out to test the ability of three exemplary PSMA trispecific antigen-binding proteins, having the sequences as set forth in SEQ ID Nos: 150, 151, and 152, to redirect T cells to kill the LNCaP cell line.

Figure 12A:
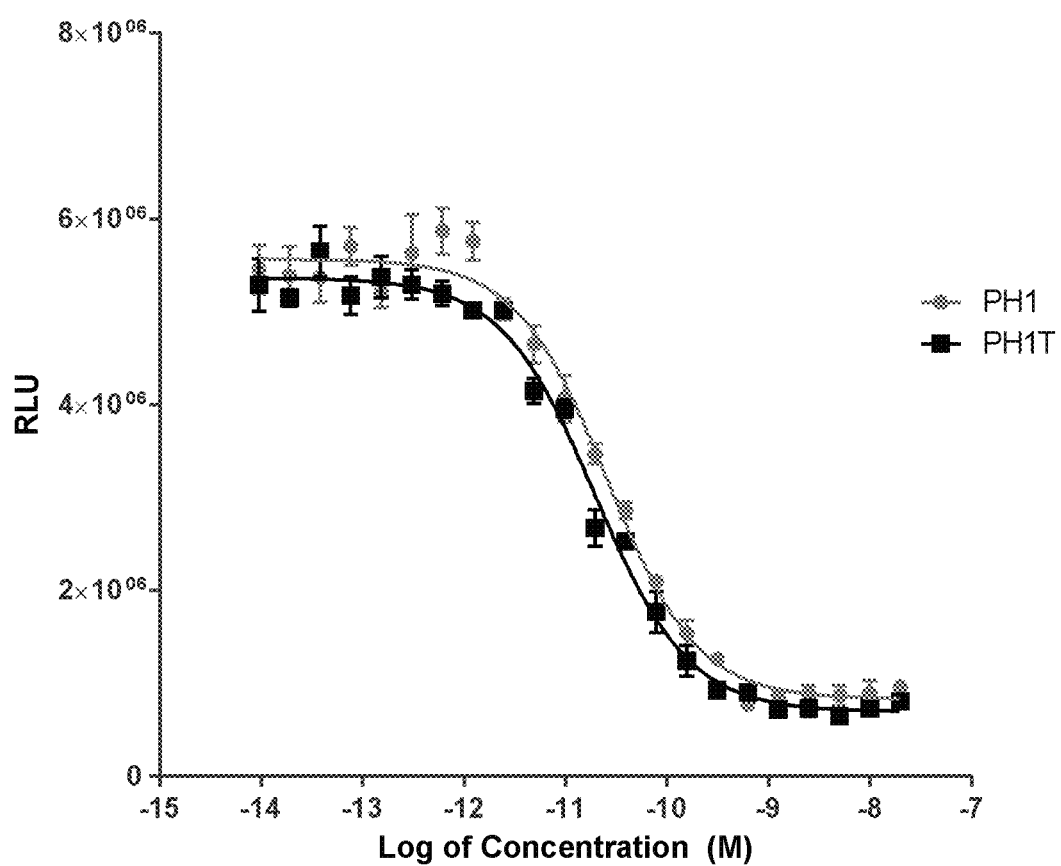
FIGS. 12A-B depict redirected T cell killing of LnCaP cells by PSMA targeting TRITAC™ molecules.
Figure 12B:
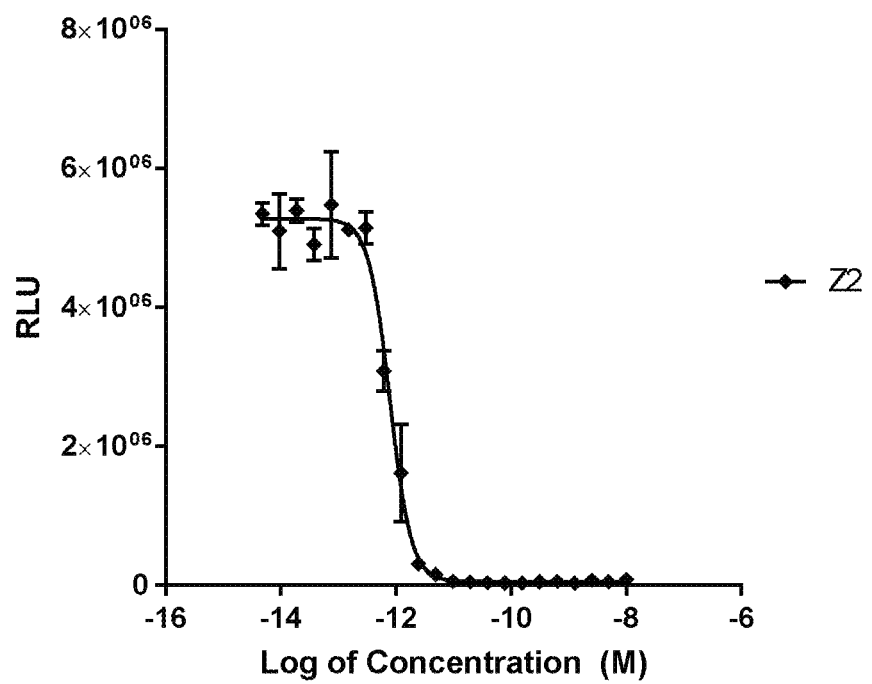

In TDCC assays, set up as described in above examples, the PSMA PH1T TRITAC™ (SEQ ID No: 150) and PSMA PH1 TRITAC™ (SEQ ID NO: 151) proteins directed killing with $EC_{50}$ values of 25 and 20 pM, respectively, as shown in FIG. 12A; and the PSMA Z2 TRITAC™ (SEQ ID NO: 152) protein directed killing with an $EC_{50}$ value of 0.8 pM, as shown in FIG. 12B.

TABLE 7

CD3 Binding Domain Sequences

| SEQ ID NO: | Description | AA Sequence |
|---|---|---|
| 1 | nti-CD3, clone 2B2 | EVQLVESGGGLVQPGGSLKLSCAASGFTFNKYAINWVRQAPGKGL EWVARIRSKYNNYATYYADQVKDRFTISRDDSKNTAYLQMNNLKT EDTAVYYCVRHANFGNSYISYWAYWGQGTLVTVSSGGGGSGGGG SGGGGSQTVVTQEPSLTVSPGGTVTLTCASSTGAVTSGNYPNWVQQ KPGQAPRGLIGGTKFLVPGTPARFSGSLLGKAALTLSGVQPEDEAE YYCTLWYSNRWVFGGGTKLTVL |
| 2 | Anti-CD3, clone 9F2 | EVQLVESGGGLVQPGGSLKLSCAASGFEFNKYAMNWVRQAPGKG LEWVARIRSKYNKYATYYADSVKDRFTISRDDSKNTAYLQMNNLK TEDTAVYYCVRHGNFGNSYISYWAYWGQGTLVTVSSGGGGSGGG GSGGGGSQTVVTQEPSLTVSPGGTVTLTCGSSFGAVTSGNYPNWV QQKPGQAPRGLIGGTKFLAPGTPARFSGSLLGKAALTLSGVQPEDE AEYYCVLWYDNRWVFGGGTKLTVL |
| 3 | Anti-CD3, clone 5A2 | EVQLVESGGGLVQPGGSLKLSCAASGFTFNKYAMNWVRQAPGKG LEWVARIRSKYNNYATYYADSVKDRFTISRDDSKNTAYLQMNNLK TEDTAVYYCVRHGNFGNSHISYWAYWGQGTLVTVSSGGGGSGGG GSGGGGSQTVVTQEPSLTVSPGGTVTLTCGSSTGYVTSGNYPNWVQ QKPGQAPRGLIGGTSFLAPGTPARFSGSLLGKAALTLSGVQPEDA EYYCVLWYSNRWIFGGGTKLTVL |
| 4 | Anti-CD3, clone 6A2 | EVQLVESGGGLVQPGGSLKLSCAASGFMFNKYAMNWVRQAPGKG LEWVARIRSKSNNYATYYADSVKDRFTISRDDSKNTAYLQMNNLK TEDTAVYYCVRHGNFGNSYISYWATWGQGTLVTVSSGGGGSGGG GSGGGGSQTVVTQEPSLTVSPGGTVTLTCGSSFGAVTSGNYPNWVQ QKPGQAPRGLIGGTKLLAPGTPARFSGSLLGKAALTLSGVQPEDE AEYYCVLWYSNSWVFGGGTKLTVL |
| 5 | Anti-CD3, clone 2D2 | EVQLVESGGGLVQPGGSLKLSCAASGFTFNTYAMNWVRQAPGKGL EWVARIRSKYNNYATYYKDSVKDRFTISRDDSKNTAYLQMNNLKT EDTAVYYCVRHGNFGNSPISYWAYWGQGTLVTVSSGGGGSGGGG SGGGGSQTVVTQEPSLTVSPGGTVTLTCGSSTGAVVSGNYPNWVQ QKPGQAPRGLIGGTEFLAPGTPARFSGSLLGKAALTLSGVQPEDA EYYCVLWYSNRWVFGGGTKLTVL |
| 6 | Anti-CD3, clone 3F2 | EVQLVESGGGLVQPGGSLKLSCAASGFTYNKYAMNWVRQAPGKG LEWVARIRSKYNNYATYYADEVKDRFTISRDDSKNTAYLQMNNLK TEDTAVYYCVRHGNFGNSPISYWAYWGQGTLVTVSSGGGGSGGG GSGGGGSQTVVTQEPSLTVSPGGTVTLTCGSSKGAVTSGNYPNWV QQKPGQAPRGLIGGTKELAPGTPARFSGSLLGKAALTLSGVQPED EAEYYCTLWYSNRWVFGGGTKLTVL |
| 7 | Anti-CD3, clone 1A2 | EVQLVESGGGLVQPGGSLKLSCAASGNTFNKYAMNWVRQAPGKG LEWVARIRSKYNNYETYYADSVKDRFTISRDDSKNTAYLQMNNLK TEDTAVYYCVRHTNFGNSYISYWAYWGQGTLVTVSSGGGGSGGG GSGGGGSQTVVTQEPSLTVSPGGTVTLTCGSSTGAVTSGYYPNWVQ QKPGQAPRGLIGGTYFLAPGTPARFSGSLLGKAALTLSGVQPEDE AEYYCVLWYSNRWVFGGGTKLTVL |
| 8 | Anti-CD3, clone 1C2 | EVQLVESGGGLVQPGGSLKLSCAASGFTFNNYAMNWVRQAPGKG LEWVARIRSKYNNYATYYADAVKDRFTISRDDSKNTAYLQMNNLK TEDTAVYYCVRHGNFGNSQISYWAYWGQGTLVTVSSGGGGSGGG GSGGGGSQTVVTQEPSLTVSPGGTVTLTCGSSTGAVTDGNYPNWV QQKPGQAPRGLIGGIKFLAPGTPARFSGSLLGKAALTLSGVQPEDE AEYYCVLWYSNRWVFGGGTKLTVL |
| 9 | Anti-CD3, clone 2E4 | EVQLVESGGGLVQPGGSLKLSCAASGFTFNKYAVNWVRQAPGKGL EWVARIRSKYNNYATYYADSVKDRFTISRDDSKNTAYLQMNNLKT EDTAVYYCVRHGNFGNSYISYWAYWGQGTLVTVSSGGGGSGGGG SGGGGSQTVVTQEPSLTVSPGGTVTLTCGESTGAVTSGNYPNWVQ QKPGQAPRGLIGGTKILAPGTPARFSGSLLGKAALTLSGVQPEDA EYYCVLWYSNRWVFGGGTKLTVL |
| 10 | Anti-CD3, clone 10E4 | EVQLVESGGGLVQPGGSLKLSCAASGFTFNKYPMNWVRQAPGKGL EWVARIRSKYNNYATYYADSVKDRFTISRDDSKNTAYLQMNNLKN EDTAVYYCVRHGNFNNSYISYWAYWGQGTLVTVSSGGGGSGGGG SGGGGSQTVVTQEPSLTVSPGGTVTLTCGSSTGAVTKGNYPNWVQ QKPGQAPRGLIGGTKMLAPGTPARFSGSLLGKAALTLSGVQPEDE AEYYCALWYSNRWVFGGGTKLTVL |
| 11 | Anti-CD3, clone 2H2 | EVQLVESGGGLVQPGGSLKLSCAASGFTFNGYAMNWVRQAPGKG LEWVARIRSKYNNYATYYADEVKDRFTISRDDSKNTAYLQMNNLK TEDTAVYYCVRHGNFGNSPISYWAYWGQGTLVTVSSGGGGSGGG GSGGGGSQTVVTQEPSLTVSPGGTVTLTCGSSTGAVVSGNYPNWV |

TABLE 7-continued

CD3 Binding Domain Sequences

| SEQ ID NO: | Description | AA Sequence |
|---|---|---|
| | | QQKPGQAPRGLIGGTEFLAPGTPARFSGSLLGGKAALTLSGVQPEDE AEYYCVLWYSNRWVFGGGTKLTVL |
| 12 | Anti-CD3, clone 2A4 | EVQLVESGGGLVQPGGSLKLSCAASGNTFNKYAMNWVRQAPGKG LEWVARIRSKYNNYATYYADSVKDRFTISRDDSKNTAYLQMNNLK TEDTAVYYCVRHGNFGDSYISYWAYWGQGTLVTVSSGGGGSGGG GSGGGGSQTVVTQEPSLTVSPGGTVTLTCGSSTGAVTHGNYPNWV QQKPGQAPRGLIGGTKVLAPGTPARFSGSLLGGKAALTLSGVQPED EAEYYCVLWYSNRWVFGGGTKLTVL |
| 13 | Anti-CD3, clone 10B2 | EVQLVESGGGLVQPGGSLKLSCAASGFTFNNYAMNWVRQAPGKG LEWVARIRSGYNNYATYYADSVKDRFTISRDDSKNTAYLQMNNLK TEDTAVYYCVRHGNFGNSYISYWAYWGQGTLVTVSSGGGGSGGG GSGGGGSQTVVTQEPSLTVSPGGTVTLTCGSYTGAVTSGNYPNWV QQKPGQAPRGLIGGTKFNAPGTPARFSGSLLGGKAALTLSGVQPED EAEYYCVLWYANRWVFGGGTKLTVL |
| 14 | Anti-CD3, clone 1G4 | EVQLVESGGGLVQPGGSLKLSCAASGFEFNKYAMNWVRQAPGKG LEWVARIRSKYNNYETYYADSVKDRFTISRDDSKNTAYLQMNNLK TEDTAVYYCVRHGNFGNSLISYWAYWGQGTLVTVSSGGGGSGGG GSGGGGSQTVVTQEPSLTVSPGGTVTLTCGSSSGAVTSGNYPNWVQ QKPGQAPRGLIGGTKFGAPGTPARFSGSLLGGKAALTLSGVQPEDE AEYYCVLWYSNRWVFGGGTKLTVL |
| 15 | wt anti-CD3 | EVQLVESGGGLVQPGGSLKLSCAASGFTFNKYAMNWVRQAPGKG LEWVARIRSKYNNYATYYADSVKDRFTISRDDSKNTAYLQMNNLK TEDTAVYYCVRHGNFGNSYISYWAYWGQGTLVTVSSGGGGSGGG GSGGGGSQTVVTQEPSLTVSPGGTVTLTCGSSTGAVTSGNYPNWVQ QKPGQAPRGLIGGTKFLAPGTPARFSGSLLGGKAALTLSGVQPEDE AEYYCVLWYSNRWVFGGGTKLTVL |
| 16 | wt anti-CD3 HC CDR1 | GFTFNKYAMN |
| 17 | wt anti-CD3 HC CDR2 | RIRSKYNNYATYYADSVK |
| 18 | wt anti-CD3 HC CDR3 | HGNFGNSYISYWAY |
| 19 | wt anti-CD3 LC CDR1 | GSSTGAVTSGNYPN |
| 20 | wt anti-CD3 LC CDR2 | GTKFLAP |
| 21 | wt anti-CD3 LC CDR3 | VLWYSNRWV |
| 22 | HC CDR1 variant 1 | GNTFNKYAMN |
| 23 | HC CDR1 variant 2 | GFEFNKYAMN |
| 24 | HC CDR1 variant 3 | GFMFNKYAMN |
| 25 | HC CDR1 variant 4 | GFTYNKYAMN |
| 26 | HC CDR1 variant 5 | GFTFNNYAMN |
| 27 | HC CDR1 variant 6 | GFTFNGYAMN |
| 28 | HC CDR1 variant 7 | GFTFNTYAMN |
| 29 | HC CDR1 variant 8 | GFTFNEYAMN |
| 30 | HC CDR1 variant 9 | GFTFNKYPMN |
| 31 | HC CDR1 variant 10 | GFTFNKYAVN |
| 32 | HC CDR1 variant 11 | GFTFNKYAIN |
| 33 | HC CDR1 variant 12 | GFTFNKYALN |
| 34 | HC CDR2 variant 1 | RIRSGYNNYATYYADSVK |
| 35 | HC CDR2 variant 2 | RIRSKSNNYATYYADSVK |
| 36 | HC CDR2 variant 3 | RIRSKYNKYATYYADSVK |
| 37 | HC CDR2 variant 4 | RIRSKYNNYETYYADSVK |

TABLE 7-continued

CD3 Binding Domain Sequences

| SEQ ID NO: | Description | AA Sequence |
|---|---|---|
| 38 | HC CDR2 variant 5 | RIRSKYNNYATEYADSVK |
| 39 | HC CDR2 variant 6 | RIRSKYNNYATYYKDSVK |
| 40 | HC CDR2 variant 7 | RIRSKYNNYATYYADEVK |
| 41 | HC CDR2 variant 8 | RIRSKYNNYATYYADAVK |
| 42 | HC CDR2 variant 9 | RIRSKYNNYATYYADQVK |
| 43 | HC CDR2 variant 10 | RIRSKYNNYATYYADDVK |
| 44 | HC CDR3 variant 1 | HANFGNSYISYWAY |
| 45 | HC CDR3 variant 2 | HTNFGNSYISYWAY |
| 46 | HC CDR3 variant 3 | HGNFNNSYISYWAY |
| 47 | HC CDR3 variant 4 | HGNFGDSYISYWAY |
| 48 | HC CDR3 variant 5 | HGNFGNSHISYWAY |
| 49 | HC CDR3 variant 6 | HGNFGNSPISYWAY |
| 50 | HC CDR3 variant 7 | HGNFGNSQISYWAY |
| 51 | HC CDR3 variant 8 | HGNFGNSLISYWAY |
| 52 | HC CDR3 variant 9 | HGNFGNSGISYWAY |
| 53 | HC CDR3 variant 10 | HGNFGNSYISYWAT |
| 54 | LC CDR1 variant 1 | ASSTGAVTSGNYPN |
| 55 | LC CDR1 variant 2 | GESTGAVTSGNYPN |
| 56 | LC CDR1 variant 3 | GSYTGAVTSGNYPN |
| 57 | LC CDR1 variant 4 | GSSFGAVTSGNYPN |
| 58 | LC CDR1 variant 5 | GSSKGAVTSGNYPN |
| 59 | LC CDR1 variant 6 | GSSSGAVTSGNYPN |
| 60 | LC CDR1 variant 7 | GSSTGYVTSGNYPN |
| 61 | LC CDR1 variant 8 | GSSTGAVVSGNYPN |
| 62 | LC CDR1 variant 9 | GSSTGAVTDGNYPN |
| 63 | LC CDR1 variant 10 | GSSTGAVTKGNYPN |
| 64 | LC CDR1 variant 11 | GSSTGAVTHGNYPN |
| 65 | LC CDR1 variant 12 | GSSTGAVTVGNYPN |
| 66 | LC CDR1 variant 13 | GSSTGAVTSGYYPN |
| 67 | LC CDR2 variant 1 | GIKFLAP |
| 68 | LC CDR2 variant 2 | GTEFLAP |
| 69 | LC CDR2 variant 3 | GTYFLAP |
| 70 | LC CDR2 variant 4 | GTSFLAP |
| 71 | LC CDR2 variant 5 | GTNFLAP |
| 72 | LC CDR2 variant 6 | GTKLLAP |
| 73 | LC CDR2 variant 7 | GTKELAP |
| 74 | LC CDR2 variant 8 | GTKILAP |

TABLE 7-continued

CD3 Binding Domain Sequences

| SEQ ID NO: | Description | AA Sequence |
|---|---|---|
| 75 | LC CDR2 variant 9 | GTKMLAP |
| 76 | LC CDR2 variant 10 | GTKVLAP |
| 77 | LC CDR2 variant 11 | GTKFNAP |
| 78 | LC CDR2 variant 12 | GTKFGAP |
| 79 | LC CDR2 variant 13 | GTKFLVP |
| 80 | LC CDR3 variant 1 | TLWYSNRWV |
| 81 | LC CDR3 variant 2 | ALWYSNRWV |
| 82 | LC CDR3 variant 3 | VLWYDNRWV |
| 83 | LC CDR3 variant 4 | VLWYANRWV |
| 84 | LC CDR3 variant 5 | VLWYSNSWV |
| 85 | LC CDR3 variant 6 | VLWYSNRWI |
| 86 | LC CDR3 variant 7 | VLWYSNRWA |
| 87 | Anti-CD3, clone 2G5 | EVQLVESGGGLVQPGGSLKLSCAASGFTFNKYALNWVRQAPGKGL EWVARIRSKYNNYATEYADSVKDRFTISRDDSKNTAYLQMNNLKT EDTAVYYCVRHGNFGNSPISYWAYWGQGTLVTVSSGGGGSGGGG SGGGGSQTVVTQEPSLTVSPGGTVTLTCGSSTGAVTSGNYPNWVQQ KPGQAPRGLIGGTNFLAPGTPERFSGSLLGGKAALTLSGVQPEDEAE YYCVLWYSNRWAFGGGTKLTVL |
| 88 | Anti-CD3, clone 8A5 | EVQLVESGGGLVQPGGSLKLSCAASGFTFNEYAMNWVRQAPGKGL EWVARIRSKYNNYATYYADDVKDRFTISRDDSKNTAYLQMNNLKT EDTAVYYCVRHGNFGNSGISYWAYWGQGTLVTVSSGGGGSGGGG SGGGGSQTVVTQEPSLTVSPGGTVTLTCGSSTGAVTVGNYPNWVQ QKPGQAPRGLIGGTEFLAPGTPARFSGSLLGGKAALTLSGVQPEDEA EYYCVLWYSNRWVFGGGTKLTVL |

TABLE 8

HSA Binding Domain Sequences

| SEQ ID NO: | Description | AA Sequence |
|---|---|---|
| 89 | Anti-HSA sdAb clone 6C | EVQLVESGGGLVQPGNSLRLSCAASGFTFSRFGMSWVRQAPGKGL EWVSSISGSGSDTLYADSVKGRFTISRDNAKTTLYLQMNSLRPEDTA VYYCTIGGSLSRSSQGTLVTVSS |
| 90 | Anti-HSA sdAb clone 7A | EVQLVESGGGLVQPGNSLRLSCAASGFTFSKFGMSWVRQAPGKGL EWVSSISGSGADTLYADSLKGRFTISRDNAKTTLYLQMNSLRPEDT AVYYCTIGGSLSKSSQGTLVTVSS |
| 91 | Anti-HSA sdAb clone 7G | EVQLVESGGGLVQPGNSLRLSCAASGFTYSSFGMSWVRQAPGKGL EWVSSISGSGSDTLYADSVKGRFTISRDNAKTTLYLQMNSLRPEDTA VYYCTIGGSLSKSSQGTLVTVSS |
| 92 | Anti-HSA sdAb clone 8H | EVQLVESGGGLVQPGNSLRLSCAASGFTFSKFGMSWVRQAPGKGL EWVSSISGSGTDTLYADSVKGRFTISRDNAKTTLYLQMNSLRPEDT AVYYCTIGGSLSRSSQGTLVTVSS |
| 93 | Anti-HSA sdAb clone 9A | EVQLVESGGGLVQPGNSLRLSCAASGFTFSRFGMSWVRQAPGKGL EWVSSISGSGSDTLYADSVKGRFTISRDNAKTTLYLQMNSLRPEDTA VYYCTIGGSLSKSSQGTLVTVSS |
| 94 | Anti-HSA sdAb clone 10G | EVQLVESGGGLVQPGNSLRLSCAASGFTFSKFGMSWVRQAPGKGL EWVSSISGSGRDTLYADSVKGRFTISRDNAKTTLYLQMNSLRPEDT AVYYCTIGGSLSVSSQGTLVTVSS |

TABLE 8-continued

HSA Binding Domain Sequences

| SEQ ID NO: | Description | AA Sequence |
|---|---|---|
| 95 | wt anti-HSA | EVQLVESGGGLVQPGNSLRLSCAASGFTFSSFGMSWVRQAPGKGLE WVSSISGSGSDTLYADSVKGRFTISRDNAKTTLYLQMNSLRPEDTA VYYCTIGGSLSRSSQGTLVTVSS |
| 96 | wt anti-HSA CDR1 | GFTFSSFGMS |
| 97 | wt anti-HSA CDR2 | SISGSGSDTLYADSVK |
| 98 | wt anti-HSACDR3 | GGSLSR |
| 99 | CDR1 variant 1 | GFTFSRFGMS |
| 100 | CDR1 variant 2 | GFTFSKFGMS |
| 101 | CDR1 variant 3 | GFTYSSFGMS |
| 102 | CDR2 variant 1 | SISGSGADTLYADSLK |
| 103 | CDR2 variant 2 | SISGSGTDTLYADSVK |
| 104 | CDR2 variant 3 | SISGSGRDTLYADSVK |
| 105 | CDR2 variant 4 | SISGSGSDTLYAESVK |
| 106 | CDR2 variant 5 | SISGSGTDTLYAESVK |
| 107 | CDR2 variant 6 | SISGSGRDTLYAESVK |
| 108 | CDR3 variant 1 | GGSLSK |
| 109 | CDR3 variant 2 | GGSLSV |
| 110 | Anti-HSA sdAb clone 6CE | EVQLVESGGGLVQPGNSLRLSCAASGFTFSRFGMSWVRQAPGKGL EWVSSISGSGSDTLYAESVKGRFTISRDNAKTTLYLQMNSLRPEDTA VYYCTIGGSLSRSSQGTLVTVSS |
| 111 | Anti-HSA sdAb clone 8HE | EVQLVESGGGLVQPGNSLRLSCAASGFTFSKFGMSWVRQAPGKGL EWVSSISGSGTDTLYAESVKGRFTISRDNAKTTLYLQMNSLRPEDTA VYYCTIGGSLSRSSQGTLVTVSS |
| 112 | Anti-HSA sdAb clone 10GE | EVQLVESGGGLVQPGNSLRLSCAASGFTFSKFGMSWVRQAPGKGL EWVSSISGSGRDTLYAESVKGRFTISRDNAKTTLYLQMNSLRPEDTA VYYCTIGGSLSVSSQGTLVTVSS |

TABLE 9

PSMA Binding Domain Sequences

| SEQ ID NO: | Description | AA Sequence |
|---|---|---|
| 113 | wt anti-PSMA | EVQLVESGGGLVQPGGSLTLSCAASRFMISEYSMHWVRQAPGKGL EWVSTINPAGTTDYAESVKGRFTISRDNAKNTLYLQMNSLKPEDTA VYYCDGYGYRGQGTQVTVSS |
| 114 | CDR1 variant 1 | RFMISEYHMH |
| 115 | CDR1 variant 2 | RFMISPYSMH |
| 116 | CDR1 variant 3 | RFMISPYHMH |
| 117 | CDR2 variant 1 | DINPAGTTDYAESVKG |
| 118 | CDR2 variant 2 | TINPAKTTDYAESVKG |
| 119 | CDR2 variant 3 | TINPAGQTDYAESVKG |
| 120 | CDR2 variant 4 | TINPAGTTDYAEYVKG |
| 121 | CDR2 variant 5 | DINPAKTTDYAESVKG |

TABLE 9-continued

PSMA Binding Domain Sequences

| SEQ ID NO: | Description | AA Sequence |
|---|---|---|
| 122 | CDR2 variant 6 | DINPAGQTDYAESVKG |
| 123 | CDR2 variant 7 | DINPAGTTDYAEYVKG |
| 124 | CDR3 variant 1 | DSYGY |
| 125 | CDR1 variant 4 | RFMISEYSMH |
| 126 | CDR2 variant 8 | TINPAGTTDYAESVKG |
| 127 | CDR3 variant 2 | DGYGY |
| 128 | Anti-PSMA clone 1 | EVQLVESGGGLVQPGGSLRLSCAASRFMISEYSMHWVRQAPGKGL EWVSTINPAGTTDYAESVKGRFTISRDNAKNTLYLQMNSLRAEDTA VYYCDGYGYRGQGTLVTVSS |
| 129 | Anti-PSMA clone 2 | EVQLVESGGGLVQPGGSLRLSCAASRFMISEYHMHWVRQAPGKGL EWVSDINPAGTTDYAESVKGRFTISRDNAKNTLYLQMNSLRAEDTA VYYCDSYGYRGQGTLVTVSS |
| 130 | Anti-PSMA clone 3 | EVQLVESGGGLVQPGGSLRLSCAASRFMISEYHMHWVRQAPGKGL EWVSTINPAGTTDYAESVKGRFTISRDNAKNTLYLQMNSLRAEDTA VYYCDSYGYRGQGTLVTVSS |
| 131 | Anti-PSMA clone 4 | EVQLVESGGGLVQPGGSLRLSCAASRFMISEYSMHWVRQAPGKGL EWVSTINPAKTTDYAESVKGRFTISRDNAKNTLYLQMNSLRAEDTA VYYCDSYGYRGQGTLVTVSS |
| 132 | Anti-PSMA clone 5 | EVQLVESGGGLVQPGGSLRLSCAASRFMISPYSMHWVRQAPGKGL EWVSTINPAGTTDYAESVKGRFTISRDNAKNTLYLQMNSLRAEDTA VYYCDGYGYRGQGTLVTVSS |
| 133 | Anti-PSMA clone 6 | EVQLVESGGGLVQPGGSLRLSCAASRFMISEYSMHWVRQAPGKGL EWVSTINPAGQTDYAESVKGRFTISRDNAKNTLYLQMNSLRAEDTA VYYCDGYGYRGQGTLVTVSS |
| 134 | Anti-PSMA clone 7 | EVQLVESGGGLVQPGGSLRLSCAASRFMISEYSMHWVRQAPGKGL EWVSTINPAGTTDYAEYVKGRFTISRDNAKNTLYLQMNSLRAEDTA VYYCDGYGYRGQGTLVTVSS |
| 135 | Anti-PSMA clone 8 | EVQLVESGGGLVQPGGSLRLSCAASRFMISEYHMHWVRQAPGKGL EWVSDINPAKTTDYAESVKGRFTISRDNAKNTLYLQMNSLRAEDTA VYYCDSYGYRGQGTLVTVSS |
| 136 | Anti-PSMA clone 9 | EVQLVESGGGLVQPGGSLRLSCAASRFMISPYHMHWVRQAPGKGL EWVSDINPAGTTDYAESVKGRFTISRDNAKNTLYLQMNSLRAEDTA VYYCDSYGYRGQGTLVTVSS |
| 137 | Anti-PSMA clone 10 | EVQLVESGGGLVQPGGSLRLSCAASRFMISEYHMHWVRQAPGKGL EWVSDINPAGQTDYAESVKGRFTISRDNAKNTLYLQMNSLRAEDT AVYYCDSYGYRGQGTLVTVSS |
| 138 | Anti-PSMA clone 11 | EVQLVESGGGLVQPGGSLRLSCAASRFMISEYHMHWVRQAPGKGL EWVSDINPAGTTDYAEYVKGRFTISRDNAKNTLYLQMNSLRAEDT AVYYCDSYGYRGQGTLVTVSS |
| 139 | Anti-PSMA clone 12 | EVQLVESGGGLVQPGGSLTLSCAASRFMISEYHMHWVRQAPGKGL EWVSDINPAGTTDYAESVKGRFTISRDNAKNTLYLQMNSLKPEDTA VYYCDSYGYRGQGTQVTVSS |
| 140 | Anti-PSMA clone 13 | EVQLVESGGGLVQPGGSLTLSCAASRFMISEYHMHWVRQAPGKGL EWVSTINPAGTTDYAESVKGRFTISRDNAKNTLYLQMNSLKPEDTA VYYCDSYGYRGQGTQVTVSS |

TABLE 10

PSMA Targeting Trispecific Protein Sequences

| SEQ ID NO: | C-Number | Construct | Sequence |
|---|---|---|---|
| 141 | C00324 | PSMA TRITAC™ CD3 high aff. | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFTFNKYAINWVRQAPGKGLEWVARIRSKYNNYAT YYADQVKDRFTISRDDSKNTAYLQMNNLKTEDTAVYYCVRHA NFGNSYISYWAYWGQGTLVTVSSGGGGSGGGGSGGGGSQTVV TQEPSLTVSPGGTVTLTCASSTGAVTSGNYPNWVQQKPGQAPRG LIGGTKFLVPGTPARFSGSLLGGKAALTLSGVQPEDEAEYYCTL WYSNRWVFGGGTKLTVLHHHHHH |
| 142 | C00339 | PSMA TRITAC™ CD3 med. aff. | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFTFNNYAMNWVRQAPGKGLEWVARIRSGYNNYA TYYADSVKDRFTISRDDSKNTAYLQMNNLKTEDTAVYYCVRHG NFGNSYISYWAYWGQGTLVTVSSGGGGSGGGGSGGGGSQTVV TQEPSLTVSPGGTVTLTCGSYTGAVTSGNYPNWVQQKPGQAPR GLIGGTKFNAPGTPARFSGSLLGGKAALTLSGVQPEDEAEYYCV LWYANRWVFGGGTKLTVLHHHHHH |
| 143 | C00325 | PSMA TRITAC™ CD3 low aff. | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFEFNKYAMNWVRQAPGKGLEWVARIRSKYNNYE TYYADSVKDRFTISRDDSKNTAYLQMNNLKTEDTAVYYCVRHG NFGNSLISYWAYWGQGTLVTVSSGGGGSGGGGSGGGGSQTVVT QEPSLTVSPGGTVTLTCGSSSGAVTSGNYPNWVQQKPGQAPRGL IGGTKFGAPGTPARFSGSLLGGKAALTLSGVQPEDEAEYYCVLW YSNRWVFGGGTKLTVLHHHHHH |
| 144 | C00236 | Tool PSMA TRITAC™ | EVQLVESGGGLVQPGGSLTLSCAASRFMISEYSMHWVRQAPGK GLEWVSTINPAGTTDYAESVKGRFTISRDNAKNTLYLQMNSLKP EDTAVYYCDGYGYRGQGTQVTVSSGGGGSGGGGSEVQLVESGG GLVQPGNSLRLSCAASGFTFSSFGMSWVRQAPGKGLEWVSSISG SGSDTLYADSVKGRFTISRDNAKTTLYLQMNSLRPEDTAVYYCT IGGSLSRSSQGTLVTVSSGGGGSGGGGSEVQLVESGGGLVQPGGS LKLSCAASGFTFNKYAMNWVRQAPGKGLEWVARIRSKYNNYA TYYADSVKDRFTISRDDSKNTAYLQMNNLKTEDTAVYYCVRHG NFGNSYISYWAYWGQGTLVTVSSGGGGSGGGGSGGGGSQTVV TQEPSLTVSPGGTVTLTCGSSTGAVTSGNYPNWVQQKPGQAPRG LIGGTKFLAPGTPARFSGSLLGGKAALTLSGVQPEDEAEYYCVL WYSNRWVFGGGTKLTVLHHHHHH |
| 145 | C00362 | PSMA p8 TRITAC™ | EVQLVESGGGLVQPGGSLRLSCAASRFMISEYSMHWVRQAPGK GLEWVSTINPAGTTDYAESVKGRFTISRDNAKNTLYLQMNSLRA EDTAVYYCDGYGYRGQGTLVTVSSGGGGSGGGGSEVQLVESGG GLVQPGNSLRLSCAASGFTFSKFGMSWVRQAPGKGLEWVSSISG SGRDTLYADSVKGRFTISRDNAKTTLYLQMNSLRPEDTAVYYCT IGGSLSVSSQGTLVTVSSGGGGSGGGGSEVQLVESGGGLVQPGGS LKLSCAASGFTFNKYAINWVRQAPGKGLEWVARIRSKYNNYAT YYADQVKDRFTISRDDSKNTAYLQMNNLKTEDTAVYYCVRHA NFGNSYISYWAYWGQGTLVTVSSGGGGSGGGGSGGGGSQTVV TQEPSLTVSPGGTVTLTCASSTGAVTSGNYPNWVQQKPGQAPRG LIGGTKFLVPGTPARFSGSLLGGKAALTLSGVQPEDEAEYYCTL WYSNRWVFGGGTKLTVLHHHHHH |
| 146 | C00363 | PSMA HDS TRITAC™ C363 | EVQLVESGGGLVQPGGSLTLSCAASRFMISEYHMHWVRQAPGK GLEWVSDINPAGTTDYAESVKGRFTISRDNAKNTLYLQMNSLKP EDTAVYYCDSYGYRGQGTQVTVSSGGGGSGGGGSEVQLVESGGG LVQPGNSLRLSCAASGFTFSKFGMSWVRQAPGKGLEWVSSISGS GRDTLYADSVKGRFTISRDNAKTTLYLQMNSLRPEDTAVYYCTI GGSLSVSSQGTLVTVSSGGGGSGGGGSEVQLVESGGGLVQPGGSL KLSCAASGFTFNKYAINWVRQAPGKGLEWVARIRSKYNNYATY YADQVKDRFTISRDDSKNTAYLQMNNLKTEDTAVYYCVRHANF GNSYISYWAYWGQGTLVTVSSGGGGSGGGGSGGGGSQTVVTQ EPSLTVSPGGTVTLTCASSTGAVTSGNYPNWVQQKPGQAPRGLI |

TABLE 10-continued

PSMA Targeting Trispecific Protein Sequences

| SEQ ID NO: | C-Number | Construct | Sequence |
|---|---|---|---|
| | | | GGTKFLVPGTPARFSGSLLGGKAALTLSGVQPEDEAEYYCTLWY SNRWVFGGGTKLTVLHHHHHH |
| 147 | C00364 | PSMA HTS TRITAC™ C364 | EVQLVESGGGLVQPGGSLTLSCAASRFMISEYHMHWVRQAPGK GLEWVSTINPAGTTDYAESVKGRFTISRDNAKNTLYLQMNSLKP EDTAVYYCDSYGYRGQGTQVTVSSGGGGSGGGSEVQLVESGGG LVQPGNSLRLSCAASGFTFSKFGMSWVRQAPGKGLEWVSSISGS GRDTLYADSVKGRFTISRDNAKTTLYLQMNSLRPEDTAVYYCTI GGSLSVSSQGTLVTVSSGGGGSGGGSEVQLVESGGGLVQPGGSL KLSCAASGFTFNKYAINWVRQAPGKGLEWVARIRSKYNNYATY YADQVKDRFTISRDDSKNTAYLQMNNLKTEDTAVYYCVRHANF GNSYISYWAYWGQGTLVTVSSGGGGSGGGGSGGGGSQTVVTQ EPSLTVSPGGTVTLTCASSTGAVTSGNYPNWVQQKPGQAPRGLI GGTKFLVPGTPARFSGSLLGGKAALTLSGVQPEDEAEYYCTLWY SNRWVFGGGTKLTVLHHHHHH |
| 148 | C00298 | PSMA BiTE | QVQLVESGGGLVKPGESLRLSCAASGFTFSDYYMYWVRQAPGK GLEWVAIISDGGYYTYYSDIIKGRFTISRDNAKNSLYLQMNSLKA EDTAVYYCARGFPLLRHGAMDYWGQGTLVTVSSGGGGSGGGG SGGGGSDIQMTQSPSSLSASVGDRVTITCKASQNVDTNVAWYQ QKPGQAPKSLIYSASYRYSDVPSRFSGSASGTDFTLTISSVQSEDF ATYYCQQYDSYPYTFGGGTKLEIKSGGGGSEVQLVESGGGLVQP GGSLKLSCAASGFTFNKYAMNWVRQAPGKGLEWVARIRSKYN NYATYYADSVKDRFTISRDDSKNTAYLQMNNLKTEDTAVYYCV RHGNFGNSYISYWAYWGQGTLVTVSSGGGGSGGGGSGGGGSQ TVVTQEPSLTVSPGGTVTLTCGSSTGAVTSGNYPNWVQQKPGQ APRGLIGGTKFLAPGTPARFSGSLLGGKAALTLSGVQPEDEAEYY CVLWYSNRWVFGGGTKLTVLHHHHHH |
| 149 | C00131 | EGFR TRITAC™ | QVKLEESGGGSVQTGGSLRLTCAASGRTSRSYGMGWFRQAPGK EREFVSGISWRGDSTGYADSVKGRFTISRDNAKNTVDLQMNSLK PEDTAIYYCAAAAGSAWYGTLYEYDYWGQGTQVTVSSGGGGS GGGGSEVQLVESGGGLVQPGNSLRLSCAASGFTFSSFGMSWVRQ APGKGLEWVSSISGSGSDTLYADSVKGRFTISRDNAKTTLYLQM NSLRPEDTAVYYCTIGGSLSRSSQGTLVTVSSGGGGSGGGSEVQL VESGGGLVQPGGSLKLSCAASGFTFNKYAMNWVRQAPGKGLE WVARIRSKYNNYATYYADSVKDRFTISRDDSKNTAYLQMNNLK TEDTAVYYCVRHGNFGNSYISYWAYWGQGTLVTVSSGGGGSG GGGSGGGGSQTVVTQEPSLTVSPGGTVTLTCGSSTGAVTSGNYP NWVQQKPGQAPRGLIGGTKFLAPGTPARFSGSLLGGKAALTLSG VQPEDEAEYYCVLWYSNRWVFGGGTKLTVLHHHHHH |
| 150 | C00457 | PSMA PH1T TRITAC™ | QVQLVESGGGVVQAGRSLTLSCAYSGVTVNVYRMGWFRQAPG KEREFVANINWSGNNRDYADSVRGRFTISRDNSKNTLYLQMNSL RAEDTAVYYCASEKPGRLGEYDYGSQGTLVTVSSGGGGSGGGS EVQLVESGGGLVQPGNSLRLSCAASGFTFSKFGMSWVRQAPGK GLEWVSSISGSGRDTLYADSVKGRFTISRDNAKTTLYLQMNSLR PEDTAVYYCTIGGSLSVSSQGTLVTVSSGGGGSGGGSEVQLVES GGGLVQPGGSLKLSCAASGFTFNKYAINWVRQAPGKGLEWVAR IRSKYNNYATYYADQVKDRFTISRDDSKNTAYLQMNNLKTEDT AVYYCVRHANFGNSYISYWAYWGQGTLVTVSSGGGGSGGGGS GGGGSQTVVTQEPSLTVSPGGTVTLTCASSTGAVTSGNYPNWV QQKPGQAPRGLIGGTKFLVPGTPARFSGSLLGGKAALTLSGVQP EDEAEYYCTLWYSNRWVFGGGTKLTVLHHHHHH |
| 151 | C00404 | PSMA PH1 TRITAC™ | QVQLVESGGGVVQAGRSLRLSCAYSGVTVNVYRMGWFRQAPG KEREFVANINWSGNNRDYADSVRGRFTISRDNSKNTLYLQMNSL RAEDTAVYYCASEKPGRLGEYDYGSQGTLVTVSSGGGGSGGGS EVQLVESGGGLVQPGNSLRLSCAASGFTFSKFGMSWVRQAPGK GLEWVSSISGSGRDTLYADSVKGRFTISRDNAKTTLYLQMNSLR PEDTAVYYCTIGGSLSVSSQGTLVTVSSGGGGSGGGSEVQLVES GGGLVQPGGSLKLSCAASGFTFNKYAINWVRQAPGKGLEWVAR IRSKYNNYATYYADQVKDRFTISRDDSKNTAYLQMNNLKTEDT AVYYCVRHANFGNSYISYWAYWGQGTLVTVSSGGGGSGGGGS GGGGSQTVVTQEPSLTVSPGGTVTLTCASSTGAVTSGNYPNWV QQKPGQAPRGLIGGTKFLVPGTPARFSGSLLGGKAALTLSGVQP EDEAEYYCTLWYSNRWVFGGGTKLTVLHHHHHH |
| 152 | C00410 | PSMA Z2 TRITAC™ | EVQLVESGGGLVQPGGSLTLSCAASRFMISEYHMHWVRQAPGK GLEWVSTINPAGTTDYAESVKGRFTISRDNAKNTLYLQMNSLRA EDTAVYYCDSYGYRGQGTLVTVSSGGGGSGGGSEVQLVESGGG LVQPGNSLRLSCAASGFTFSKFGMSWVRQAPGKGLEWVSSISGS GRDTLYADSVKGRFTISRDNAKTTLYLQMNSLRPEDTAVYYCTI GGSLSVSSQGTLVTVSSGGGGSGGGSEVQLVESGGGLVQPGGSL KLSCAASGFTFNKYAINWVRQAPGKGLEWVARIRSKYNNYATY |

TABLE 10-continued

PSMA Targeting Trispecific Protein Sequences

| SEQ ID NO: | C-Number | Construct | Sequence |
|---|---|---|---|
| | | | YADQVKDRFTISRDDSKNTAYLQMNNLKTEDTAVYYCVRHANF GNSYISYWAYWGQGTLVTVSSGGGGSGGGGSGGGGSQTVVTQ EPSLTVSPGGTVTLTCASSTGAVTSGNYPNWVQQKPGQAPRGLI GGTKFLVPGTPARFSGSLLGGKAALTLSGVQPEDEAEYYCTLWY SNRWVFGGGTKLTVLHHHHHH |

TABLE 11

PSMA Binding Domain CDR sequences

| SEQ ID Nos. | Sequence |
|---|---|
| SEQ ID No. 162 | RFMISX$_1$YX$_2$MH |
| SEQ ID No. 163 | X$_3$INPAX$_4$X$_5$TDYAEX$_6$VKG |
| SEQ ID No. 164 | DX$_7$YGY |

TABLE 12

Exemplary Framework Sequences

| SEQ ID NO: | Description | Sequence |
|---|---|---|
| 165 | Framework (f1) | EVQLVESGGGLVQPGGSLTLSCAAS |
| 166 | Framework (f2) | WVRQAPGKGLEWVS |

TABLE 12-continued

Exemplary Framework Sequences

| SEQ ID NO: | Description | Sequence |
|---|---|---|
| 167 | Framework (f3) | RFTISRDNAKNTLYLQMNSLRAEDTAVYYC |
| 168 | Framework (f4) | DGYGYRGQGTLVTVSS |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A trispecific protein targeting an epitope within a human prostate specific membrane antigen (PSMA), wherein said protein comprises
   (a) a first domain (A) which is a single chain variable fragment (scFv) comprising the amino acid sequence SEQ ID NO: 1, that specifically binds to a human CD3;
   (b) a second domain (B) which is a single domain antibody (sdAb) comprising the amino acid sequence of SEQ ID NO: 94, that specifically binds to a human serum albumin protein; and
   (c) a third domain (C) which is a sdAb that specifically binds to the human PSMA, comprising a complementarity determining region 1 (CDR1), a CDR2, and a CDR3, wherein the CDR1 comprises the amino acid sequence of SEQ ID NO: 114; the CDR2 comprises the amino acid sequence of SEQ ID NO: 126; and the CDR3 comprises the amino acid sequence of SEQ ID NO: 124;
   wherein the domains are linked in an order of H$_2$N-(C)-(B)-(A)-COOH, or by linkers L1 and L2 in an order of H$_2$N-(C)-L1-(B)-L2-(A)-COOH, and wherein the human PSMA is a 100 kD Type II membrane glycoprotein expressed in prostate tissue.

2. The trispecific protein of claim 1, wherein linkers L1 and L2 each independently comprises a sequence selected from the group consisting of (GS)$_n$ (SEQ ID NO: 153), (GGS)$_n$ (SEQ ID NO: 154), (GGGS)$_n$ (SEQ ID NO: 155), (GGSG)$_n$ (SEQ ID NO: 156), (GGSGG)$_n$ (SEQ ID NO: 157), and (GGGGS)$_n$ (SEQ ID NO: 158); wherein n is 1, 2, 3, 4, 5, 6, 7, 8, 9, or 10.

3. The trispecific protein of claim 1, wherein the protein is less than about 80 kDa.

4. The trispecific protein of claim 1, wherein the protein is from about 50 kDa to about 75 kDa.

5. The trispecific protein of claim 1, wherein the protein is less than about 60 kDa.

6. The trispecific protein of claim 1, wherein the protein has an elimination half-time of at least 50 hours following administration to a subject.

7. The trispecific protein of claim 1, wherein the protein has an elimination half-time of at least 100 hours following administration to a subject.

8. A pharmaceutical composition comprising (i) the trispecific protein according to claim 1, and (ii) a pharmaceutically acceptable carrier.

9. The trispecific protein of claim 1, wherein the third domain (C) comprises the amino acid sequence of SEQ ID NO: 140.

10. A method of treating prostate cancer expressing a human prostate specific membrane antigen (PSMA), the method comprising the administration of an effective amount of the trispecific protein of claim 1 to a subject having said prostate cancer, wherein said human PSMA is a 100 kD type II membrane glycoprotein expressed in prostate tissue.

11. A trispecific protein targeting an epitope within a human prostate specific membrane antigen (PSMA) comprising the amino acid sequence of SEQ ID NO: 147, wherein the human PSMA is a 100 kD Type II membrane glycoprotein expressed in prostate tissue.

* * * * *